US008604217B2

(12) United States Patent
Brzózka et al.

(10) Patent No.: US 8,604,217 B2
(45) Date of Patent: Dec. 10, 2013

(54) COMPOUND, A PROCESS FOR ITS PREPARATION, A PHARMACEUTICAL COMPOSITION, USE OF A COMPOUND, A METHOD FOR MODULATING OR REGULATING SERINE/THREONINE KINASES AND A SERINE/THREONINE KINASES MODULATING AGENT

(75) Inventors: Krzysztof Brzózka, Sieradz (PL); Wojciech Czardybon, Mikolów (PL); Aleksandra Sabiniarz, Brzeg Dolny (PL); Mariusz Millik, Kraków (PL); Renata Windak, Kraków (PL); Adrian Zarebski, Busko-Zdrój (PL); Nicolas Beuzen, Kraków (PL)

(73) Assignee: Selvita S.A., Krakow (PL)

( * ) Notice: Subject to any disclaimer, the term of this patent is extended or adjusted under 35 U.S.C. 154(b) by 0 days.

(21) Appl. No.: 13/339,104

(22) Filed: Dec. 28, 2011

(65) Prior Publication Data

US 2012/0184535 A1    Jul. 19, 2012

Related U.S. Application Data

(63) Continuation-in-part of application No. 12/617,067, filed on Nov. 12, 2009, now abandoned, and a continuation of application No. PCT/EP2010/067385, filed on Nov. 12, 2010.

(30) Foreign Application Priority Data

Nov. 12, 2009   (EP) ..................................... 09460048

(51) Int. Cl.
*A61K 31/5377* (2006.01)
*A61K 31/496* (2006.01)
*A61K 31/454* (2006.01)
*C07D 401/04* (2006.01)
*C07D 403/04* (2006.01)
*C07D 413/04* (2006.01)

(52) U.S. Cl.
USPC ..................... 548/306.1; 548/310.1; 544/139; 544/370; 546/199; 514/234.5; 514/254.06; 514/322; 514/394

(58) Field of Classification Search
USPC ............................................. 548/306.1, 310.1
See application file for complete search history.

(56) References Cited

U.S. PATENT DOCUMENTS 3,705,944 A * 12/1972 Frick et al. ..................... 514/394
3,935,314 A *  1/1976 Watts ............................ 514/388
5,326,502 A *  7/1994 Bird et al. ..................... 252/589
6,958,357 B2  10/2005 Hofmeister et al.
7,049,333 B2 *  5/2006 Lang et al. .................... 514/388

2004/0006119 A1  1/2004 Lang et al.
2009/0197866 A1  8/2009 Cherrier et al.
2009/0197889 A1  8/2009 Winfield

FOREIGN PATENT DOCUMENTS

| GB | 1 286 603 | 8/1972 |
|---|---|---|
| WO | WO 02/46169 A1 | 6/2002 |
| WO | WO 03/030902 A1 | 4/2003 |
| WO | WO 2005/004864 A1 | 1/2005 |
| WO | WO 2005/092866 A1 | 10/2005 |
| WO | WO 2007/062342 A1 | 5/2007 |
| WO | WO 2007/100646 A1 | 9/2007 |
| WO | WO 2008/003857 A1 | 1/2008 |
| WO | WO 2011/058139 A1 | 5/2011 |

OTHER PUBLICATIONS

Koronkiewicz et al., Polish Pharmaceutical Society, (Nov.-Dec. 2010), 67(6), pp. 635-641.*
Golub et al., Science, vol. 286, Oct. 15, 1999, pp. 531-537.*
Doan et al., Journal of Clinical Pharmacology, 2005, 45, pp. 751-762.*
Front cover page of the journal Acta Poloniae Pharmaceutica, v 67, No. 6 (Nov.-Dec. 2010).*
Koronkiewicz, M. "Synthesis and proapoptotic properties of new casein kinase II inhibitors.", Embase, Elsevier, Nov. 15, 2010, web date May 10, 2013, (Embase Accession No. 2010598222).*
Andrzejewska, M., et al., "Polyhalogenobenzimidazoles: Synthesis and Their Inhibitory Activity against Casein Kinases," *Bioorg. Med Chem.* 11:3997-4002, Elsevier Ltd., United States (2003).
Battistutta, R., et al., "Inspecting the Structure-Activity Relationship of Protein Kinase CK2 Inhibitors Derived from Tetrabromo-Benzimidazole," *Chem. Biol.* 12:1211-1219, Elsevier Ltd., United States (2005).
Bortolato, A. and Moro, S., "In Silico Binding Free Energy Predictability by Using the Linear Interaction Energy (LIE) Method: Bromobenzimidazole CK2 Inhibitors as a Case Study," *J. Chem. Inf. Model.* 47:572-582, Amercian Chemical Society, United States (2007).
Coats, E.A., et al., "Correlation analysis of pyrimidine folic antagonists as antibacterial agents .1." *Eur. J. Med. Chem.* 14(3):261-270, Editions Scientifiques Elsevier, France (1979).

(Continued)

*Primary Examiner* — Laura L. Stockton
(74) *Attorney, Agent, or Firm* — Sterne, Kessler, Goldstein & Fox P.L.L.C.

(57) ABSTRACT

A compound, a process for its preparation, a pharmaceutical composition, use of a compound, a method for modulating or regulating serine/threonine and tyrosine kinases and a serine/threonine and tyrosine kinases modulating agent. Novel small-molecule compounds with kinase inhibitory activity, having superior properties as pharmaceutical agents, production method thereof and uses thereof. In particular, new derivatives of tetrahalogenated benzimidazole with serine/threonine and tyrosine kinases inhibitory properties, preferably selected from the group of PIM, HIPK, DYRK, CLK, CDK, FLT, PKG, Haspin, MER, TAO, MNK, TRK kinases which exhibit superior pharmacological actions, and can be useful for the treatment of disease conditions, especially cancers depending on serine/threonine and tyrosine kinases, such as but not limited to leukemias and solid tumors.

23 Claims, 2 Drawing Sheets

(56) References Cited

OTHER PUBLICATIONS

Gianoncelli, A., et al., "Tetraidobenzimidazoles are potent inhibitors of protein kinase CK2," *Bioorg. Med. Chem.* 17(27):7281-8289, Elsevier Ltd., United States (2009).

Inukai, Y., et al., "*ortho*-Distributed *F*-Benzenes. I. Preparation of (*F*-Benzo)heterocyclic Compounds from *F*-Aniline and the Reactions of Some Intermediate (*F*-Phenyl)amino Compounds," *Bull. Chem. Soc. Jpn.* 52(2):516-520, Nippon Kagakukai, Japan (1979).

Kolesnikova, I.V., et al., "Reactions of N-Polyfluorophenylcarbonimodoyl Dichlomides with Primary Secondary Amines, Kinetics and Mechanism. Sythesis of Polyfluoronated Cabodimides, Chloroformadines, Guanidines, Benzimidazoles," *J. Fluor. Chem.* 40(1):217-246, Elsevier Sequoia, Netherlands (1988).

Kolesnikova, I.V., et al., "Reaction of N-Polyfluorophenylcarbonimodoyl Dichlomide with Primary Amines," *J. Org. Chem. USSR* 25(8):1523-1529, Plenum Publishing Corporation, England (1990).

Murata, H., et al., "2-(4,5,6,7-Tetrafluorobenzimidazol-2-yl)-4,4,5,5-tetramethyl-4,5-dihydro-1-*H*-imidazole-3-oxide-1-oxyl, A Hydrogen-Bonded Organic Quasi-1D Ferromagnet," *J. Am. Chem. Soc.* 130:186-194, American Chemical Society, United States (2008).

Pagano, M.A., et al., "2-Dimethylamino-4,5,6,7-tetrabromo-1*H*-benzimidazole: a Novel Powerful and Selective Inhibitor of Protein Kinase CK2," *Biochem. Biophys. Res. Commun.* 320:1040-1044, Elsevier Inc., England (2004).

Pagano, M.A., et al., "The Selectivity of inhibitors of protein kinase CK2: an update," *Biochem. J.* 415:353-365, the Authors Journal compilation and Biochemical Society, England (2008).

Röchling, H., et al., "Synthesen von Benzimidazolonen und Polychlorierten Benzimidazolonen," *Zeitschrift fur Naturforscung, TeilAnorganische Chemie, Organische Chemis* 25(1):954-960, Verlag der Zeitschrift fur Naturfoschung, Germany (1970).

Werbel, L.M., et al., "Synthesis and Anitmalarial Effects of 5,6-Dichloro-2-[(4-[(diethylamino)-1-methylbutyl]amino]-6-methyl-2-pyrimidinyl)amino]benzimidazole and Related Benzimidazoles and 1*H*-Imidazo[4,5-*b*] pyridines (1,2)," *J. Heterocyl. Chem.* 1973:363-382, Wiley-Blackwell Publishing, Inc., United States (1973).

IUPAC ED—McNaught, A.D. and Wilkinson, A. "alkyl groups," Compendium of Chemical Terminology: IUPAC Recommendations; IUPAC Data Series, Blackwell Science, England, retrieved from www.iupac.org/goldbook/A00228.pdf, retrieved on Jan. 1, 1997.

Database Registry, Accession No. 791780-63-7, 1H-Bezimidazol-2-amine, 4,5,6,7-tetrafluoro-N-(4-methyl-3-thienyl)-, entered Dec. 3, 2004, Chemical Abstracts Service, United States.

Database Registry, Accession No. 791584-58-263-7, 1H-Bezimidazol-2-amine, N-(2-chloro-4-methyl-3-thienyl)-4,5,6,7-tetrafluoro-, entered Dec. 2, 2004, Chemical Abstracts Service, United States.

International Search Report with Written Opinion for International Application No. PCT/EP2010/067385, European Patent Office, Netherlands, mailed Mar. 3, 2011.

English language translation of Russian Office Action issued Apr. 19, 2013 for Russian Patent Application No. 2012120784/04(031353).

\* cited by examiner

COMPOUND, A PROCESS FOR ITS PREPARATION, A PHARMACEUTICAL COMPOSITION, USE OF A COMPOUND, A METHOD FOR MODULATING OR REGULATING SERINE/THREONINE KINASES AND A SERINE/THREONINE KINASES MODULATING AGENT

CROSS-REFERENCE TO RELATED APPLICATIONS

This is a continuation-in-part of U.S. application Ser. No. 12/617,067, filed Nov. 12, 2009, now abandoned, and a continuation of International Patent Application No. PCT/EP2010/067835, with an international filing date of Nov. 12, 2010, now pending, designating the United States, which is based on European Patent Application No. EP 09460048.3, filed Nov. 12, 2009 and U.S. application Ser. No. 12/617,067, filed Nov. 12, 2009. The contents of all of the aforementioned specifications including any intervening amendments thereto are specifically incorporated herein by reference.

BACKGROUND OF THE INVENTION

1. Field of the Invention

The present invention is inter alia concerned with a compound, a process for its preparation, a pharmaceutical composition, use of a compound, a method for modulating or regulating serine/threonine and tyrosine kinases and a serine/threonine and tyrosine kinases modulating agent. The present invention thus inter alia relates to novel small-molecule compounds with kinase inhibitory activity, having superior properties as pharmaceutical agents, production method thereof and uses thereof. In particular, this invention relates to new derivatives of tetrahalogenated benzimidazoles with serine/threonine and tyrosine kinases inhibitory properties, wherein the kinases are preferably selected from the group of PIM, HIPK, DYRK, CLK, CDK, FLT, PKG, Haspin, MER, TAO, MNK, TRK kinases, and wherein the derivatives exhibit inter alia superior pharmacological actions, and can be useful for the treatment of disease conditions, especially cancers depending on serine/threonine kinases, such as e.g. leukemias, lymphomas and solid tumors.

2. Description of the Related Art

Kinases are enzymes that modify other proteins by chemically adding phosphate groups to them (a process called phosphorylation). Phosphorylation of the targeted proteins results in a functional change of their activity but also can modify association with other proteins, trafficking and subcellular localization. It is estimated that up to 30% of all proteins can be modified by kinases. For this reason kinases are key regulators of majority of cellular pathways, especially those involved in signal transduction. Kinases are currently one of the most interesting and most extensively investigated drug targets. Among the new kinase targets for therapeutic inhibition pursued currently, PIM kinases are definitely one of the most interesting emerging molecular targets. The PIM family of serine-threonine kinases is composed of three highly homologous proteins PIM-1, -2 and -3 which play an important role in intracellular signaling and contribute to pathways involved in cell survival, inflammation, cell movement and stress response.

Around 15 years ago, the PIM-1 gene was identified as a proviral insertion site of the Moloney Murine Leukemia Virus (MoMuLV) in experiments designed to find new genes, which are involved in tumorogenesis. These findings established PIM-1 as a proto-oncogene and important player in the process of malignant transformation (Nagarajan et al., 1986). In humans, the PIM-1 gene is located on chromosome 6p21.1-p21.31 (Zakut-Houri et al., 1987). The PIM-1 gene comprises approximately 5 kb, contains six exons and five introns. Its cDNA contains an open reading frame of 313 codons with 94% homology to the mouse counterpart. The RNA transcript is 2.9 kilobases (kb) long (Saris et al., 1991). Shortly after discovery of the gene, PIM-1 protein was identified to be a serine/threonine kinase, belonging to CAMK kinases (group of calcium/calmodulin-regulated kinases). (Saris et al., 1991; Reeves et al., 1990). It contains ATP-anchor, kinase domain and an active site. There are two forms of PIM-1 in human and mouse, associated with alternative initiation codon (44 kDa and 33 kDa). Both forms have relatively short half-life, however the 44 kDa isoform seems to be more stable. Activity of PIM-1 kinase is found in the cytoplasm, nuclear fraction and the membrane of the cells. Two isoforms have different subcellular localization—44 kDa is present mainly on the plasma membrane; 33 kDa in nucleus and cytoplasm. The crystal structure of PIM-1 obtained in 2005 revealed that it is a constitutively active kinase and that in contrast to many other kinases, like Akt or MAPK kinases, PIM-1 does not require additional phosphorylation for its kinase activity, however phosphorylation of this protein may contribute to its stability (Qian et al., 2005a; Qian et al., 2005b). Obtained crystal structure allowed also discovering unusual structural features of the PIM-1 kinase domain. Most notably, the hinge region presents two features of particular interest: an insertion residue as well as a proline residue (Pro123), which combine to form an ATP- and inhibitor-binding region quite distinct from other protein kinases. A substrate recognition sequence of the PIM-1 kinase was identified by selective peptide mapping ((K/R)3-X-S/T-X or R/K-R/K-R-R/K-X-S/T-X, where X is an amino acid (aa) residue with a small side chain but neither basic nor acidic) (Peng et al., 2007).

With regard to molecular mechanisms of PIM-1 involvement in oncogenic transformation and cancer development, one can point out several processes that are regulated by the PIM-1 kinase like stimulation of cell cycle progression, co-activation of mTOR pathway, inhibition of apoptosis, transcriptional coactivation of c-Myc, promotion of drug resistance and cell migration and metastasis PIM kinases overexpression has been reported in a variety of cancer types, ranging from hematopoietic malignancies such as diffuse B cell lymphoma, chronic lymphocytic leukemia and acute myelogenous leukemia to solid tumors such as prostate and pancreatic cancer. Acquisition of mutations in the PIM-1 gene can be one of the molecular mechanisms involved in histological transformation of follicular lymphoma (FL) and B-chronic lymphocytic leukemia (B-CLL) to diffuse large B-cell lymphoma (DLBCL)(Rossi et al., 2006). Mutations of the PIM-1 gene have also been detected in cases of AIDS-associated non-Hodgkin lymphoma (Gaidano et al., 2003), HCV-infected B-cell NHL patients (Libra et al., 2005), primary central nervous system lymphomas (PCNSLs) (Montesinos-Rongen et al., 2004), extranodal DLBCL cases and primary cutaneous marginal zone B-cell lymphoma (PC-MZL) (Deutsch et al., 2009; Deutsch et al., 2007), primary mediastinal large B-cell lymphoma (PMLBCL)(Martelli et al., 2008). PIM-1 kinase is upregulated in Epstein Barr virus infected B-cells where it enhances transcriptional activity of EBNA2 protein, essential for the growth transformation and immortalization of infected B-cells. This mechanism of action of PIM-1 kinases may predispose immortalized B-cell to undergo malignant transformation (Rainio et al., 2005). Initial study performed by Amson in 1989 showed that the 33 kDa isoform of PIM-1 kinase was overexpressed in approximately 30% of the analyzed samples (out of 70 hematopoietic malignancies analyzed—51 patients and 19 cell lines), pointing toward the role of this kinase in development of myeloid and lymphoid acute leukemias (Amson et al., 1989). This finding was further confirmed in a variety of other studies showing elevated levels of PIM-1 kinase in various human clinical leukemias and myeloid and lymphocytic cell lines (Meeker et al., 1990). For example, PIM-1 kinase was implicated in leukemogenesis and aberrant expression levels of this kinase can be involved neoplastic transformation by phosphorylation and activation of Runx transcription factors (Aho et al., 2006; Kim et al., 2008). Chromosome translocations and point mutations are well-documented and frequent genetic alterations in RUNX leukemias (Penther et al., 2002; Osato and Ito, 2005). PIM-1 seems to play also a crucial role in development of acute myeloid leukemias (AML). Several reports pointed out a role of PIM-1 kinase in downstream signaling by FLT3 (Fms-like tyrosine kinase 3) kinase. Constitutively activating internal tandem duplication (ITD) mutations of the receptor tyrosine kinase FLT3 play an important role in leukemogenesis, and their presence is associated with poor prognosis in AML. Constitutive FLT3 signaling upregulates PIM-1 levels in leukemia cells and the juxtamembrane domain of FLT3 is a critical domain required for this upregulation (Kim et al., 2005; Vu et al., 2009). Interestingly, this downstream signaling seems to be independent of STAT5, Akt and MAPK signaling. Up-regulation of PIM-1 kinase contributes to the proliferative and antiapoptotic pathways induced by FLT3 signaling, and the major antiapoptotic mechanism of action is PIM-1 dependent Bad phosphorylation (Kim et al., 2006). Similarly to FLT3, PIM-1 kinase is also upregulated by the Bcr-Abl fusion protein, a major cause of the chronic myelogenous leukemia. A SH3/SH2 mediated interaction of Bcr/Abl kinase with Hck kinase (hematopoietic cell kinase) lead to activation of Hck and phosphorylation of STAT5B on the critical Tyr699 residue. Activated STAT5B stimulates expression of downstream effectors like PIM-1 kinase and the A1 protein, key factors essential for in vitro transformation and in vivo leukemogenesis mediated by Bcr/Abl. (Klejman et al., 2002; Nieborowska-Skorska et al., 2002). Whereas inhibition of PIM-1 seems not to be sufficient to overcome Bcr/Abl mediated transformation in cancer cells, an elegant study by Adam et al., showed that PIM-1 and PIM-2 play here redundant roles and simultaneous targeting of the two kinases may be an exciting therapeutic alternative to overcome resistance against small-molecule tyrosine kinase inhibitors (Nosaka and Kitamura, 2002; Adam et al., 2006). Involvement of PIM-1 kinase in development of prostate cancer has been extensively studied over the past years and provided several examples of clinical importance and rationale for therapeutic indication. Already in 2001 in a microarrays screen PIM-1 expression was shown to correlate with clinical outcome of the disease and was suggested to be a better marker than the standard diagnostic test for PSA levels in serum (Dhanasekaran et al., 2001). This was further confirmed in studies performed by other groups (Cibull et al., 2006; Xu et al., 2005; Thompson et al., 2003; Valdman et al., 2004). Overexpression of PIM-1 in human prostate cancer cells induces genomic instability by subverting the mitotic spindle checkpoint, centrosome amplification, chromosome misaggregation and polyploidy. When the PIM-1 kinase is overexpressed in immortalized, non-tumorigenic human cells, these cells became tumorigenic (Roh et al., 2008; Roh et al., 2003). A very interesting finding by Zemskova and colleagues support additionally use of PIM-1 kinase inhibitors in prostate cancer treatment. Surprisingly, treatment of prostate cancer cells with docetaxel, a standard of care induces STAT3 phosphorylation and transcriptional upregulation of the PIM-1 gene. Expression of PIM-1 kinase was crucial for survival of these cells after docetaxel treatment, as shown by knock down and inhibitor experiments. This data supports further testing of novel, small molecule kinase inhibitors in combination therapies with patients with docetaxel resistance (Zemskova et al., 2008). In an extensive study by Beier et al., immunohistochemistry experiment performed on cells compared to non-neoplastic tissue showed overexpression of the PIM-1 protein in 98% (41/42) of invasive head and neck squamous cell carcinomas (HNSCC). This study was repeated using primary tumors and metastasis biopsies showing nearly significant correlation of PIM-1 expression with histological tumor, underlining role of PIM-1 in HNSCC developments (Beier et al., 2007). In line with this finding, moderate or high expression of PIM-1 and nuclear localization was also linked to prediction of radiation response in squamocellular cancers of head and neck (Peltola et al., 2009).

PIM-2 is a second member of the PIM kinase family. Functionally, it has been noticed that PIM-2 overlaps with the Akt/mTOR pathway, but is regulated independently. Both PIM-2 and Akt1 kinase regulate NFκB-dependent transcription by phosphorylation of the Cot kinase (Kane et al., 2002; Hammerman et al., 2004). It has been indicated that PIM-2 expression maintains high levels of NF-κB activity and NF-κB activation by PIM-2 is required for its antiapoptotic function. Moreover, the data has suggested that Cot-dependent activation of NFκB can occur via the transcriptional induction of PIM-2 rather than as a direct result of a receptor-initiated kinase cascade. Several reports showed that PIM-2 can to some extent substitute or cooperate with PIM-1 in driving tumorigenesis. As both kinases share some of the targets, like the Bad protein, they act both as prosurvival kinases preventing induction of apoptosis (Yan et al., 2003; Aho et al., 2004). As both PIM-1 and 2 are transcriptionally induced by upstream signaling (like FLT3 or Bcr-Abl signaling), they can cooperate and are essential in neoplastic transformation of B-cells by v-Abl oncogene (Chen et al., 2008). Similarly to PIM-1, coexpression of PIM-2 and c-Myc transgene induces malignant transformation (Allen et al., 1997). Also the effect on the cell cycle inhibition for both PIM-1 and PIM-2 seem to synergize in accelerating cell proliferation and cell cycle progression as shown in the literature, although the molecular mechanism of cell cycle regulation are described in detail only for PIM-1 kinase (Dai et al., 2005; Chen et al., 2005) There seem however also to be differences between the two kinases. Whereas recent publications on hypoxia point out its emerging role in solid tumor formation and chemoresistance, no similar reports are known for PIM-2 kinase and this role needs to be explored. On the other hand, in the recent publication by Tamburini, a special emphasis was put on the role of PIM-2 in phosphorylation of crucial 4EBP1 transcription factor (on serine S65)(Tamburini et al., 2009). As shown in this publication, expression of PIM-1 in clinical samples did not correlate with the above finding, providing a proof for non-overlapping role of PIM-1 and PIM-2 in regulation of 4EBP1 phosphorylation, regulation of protein synthesis and promotion of neoplastic transformation. Similar finding were already reported in by Fox and colleagues, stressing out a crucial role of PIM-2 kinase in controlling translation independently from the Akt/mTOR pathway and pointing towards inhibition of PIM-1 kinase as an attractive option for development of new therapies, especially in acute myelogenous leukemia (Fox et al., 2003).

Similarly to PIM-1, overexpression of PIM-2 has been documented in several human tumors types. One of the distinguishing reports is involvement of PIM-2 in tumorigenesis of hepatocellular carcinoma (HCC) (Gong et al., 2008). PIM-2 gene expression and its protein levels were investigated in human liver cancer tissues and HepG2 cells (human hepatocellular liver carcinoma cell line). In both cases the expression of PIM-2 gene and protein was higher than in immortalized liver cell line L02, indicating its role as a tumor biomarker. Further experiments indicated that PIM-2 expression and its kinase activity are IL-3 dependent; however its apoptotic inhibition role is IL-3-inedependent. It was also found that protection against apoptosis by PIM-2 is glucose-dependent, so liver cells growing in vivo, surrounded by high glucose and growth factors concentration have favorable conditions to express PIM-2, however PIM-2 was unable to prevent apoptosis upon glucose deprivation. So once overexpressed in hepatic cells PIM-2 can be an important factor in tumorigenesis.

PIM-3 (also known as Kid-1—kinase induced by depolarization) is the third member of the PIM kinase family. Similarly to PIM-2 and PIM-1, PIM-3 acts in a prosurvival way preventing apoptosis by phosphorylation of Bad. However, in contrast to PIM-1/2, PIM-3 seems to be less specific to Ser112 residue, preferably phosphorylating Ser136, Ser155 and Ser170 (Macdonald et al., 2006). PIM-3 was the most effective kinase in phosphorylating Ser136 residue, which seems to be crucial for subsequent phosphorylation steps and interaction with the anti-apoptotic Bcl-XL protein. PIM phosphorylation of Bad was therefore found to promote the 14-3-3 binding and inhibition of Bcl-XL binding. Similarly to PIM-1, PIM-3 seems to be also involved in promoting vessel formation and angiogenesis (Zippo et al., 2004; Zhang et al., 2009b). Angiogenesis is a physiological process involving the growth of new blood vessels from pre-existing vessels. This feature play significant role in tumorigenesis because angiogenesis usually precede metastasis. Although angiogenesis is a normal process in growth and development it is also a fundamental step in the transition of tumors from a dormant state to a malignant one. It was found that PIM-3 is highly expressed both at mRNA and protein levels in endothelial cells and the protein is co-localized at the cellular lamelliopodia focal kinase (FAK), a kinase involved in cellular adhesion and spreading processes. FAK is typically located at structures known as focal adhesions; these are multi-protein structures that link the extracellular matrix to the cytoplasmic cytoskeleton. It is recruited as a participant in focal adhesion dynamics between cells and has a role in motility and cell survival. FAK have also tyrosine kinase activity and originally identified as a substrate for the oncogene protein. After treatment with cytochalasin D which disrupts actin microfilaments, PIM-3 was dispersed from lamelliopodia suggesting strong interaction of PIM-3 with cytoskeleton. Furthermore knockdown of PIM-3 by siRNA had significant effects on endothelial cells migration, proliferation and formation of sprouts. In light of this finding PIM-3 kinase seems to be a new and promising target for novel inhibitors of angiogenesis.

PIM-3 overexpression has been observed in several human cancers, mainly solid tumors like gastrointestinal, colon or liver cancers where expression of PIM-3 seems to be also a poor prognostic marker, however its role in development of pancreatic adenocarcinoma has been studies in more detail (Popivanova et al., 2007; Zheng et al., 2008). PIM-3 was found to be expressed in malignant lesions of the pancreas but not in normal pancreatic tissue (Li et al., 2006). In line with this finding, PIM-3 mRNA and protein were constitutively expressed in all examined human pancreatic cancer cell lines. Knock down of the PIM-1 mRNA levels resulted in apoptosis of the cells, proving essential role of PIM-3 in inhibition of apoptosis in pancreatic cancer cell lines. Further experiments showed that expression of PIM-3 in pancreatic cell lines is controlled by binding of the Ets-1 protein to the 5'-flanking region of human PIM-3 gene between −249 and −183 bp (Li et al., 2009). Overexpression of Ets-1 transcription factor was able to stimulate transcription and translation of the PIM-3 kinase. These observations indicate that the transcription factor Ets-1 can induce aberrant PIM-3 expression and subsequently prevent apoptosis in human pancreatic cancer cells. Despite the fact that PIM-3 is a kinase of emerging role in cancer development, presented above results implicate how important and diversified roles PIM-3 may play in tumorigenesis and provide rationale for further development of PIM-3 inhibitors for cancer treatment.

CLK kinases belong to Lammer dual specificity kinase subfamily and phosphorylate serines, threonines and tyrosines. The family consists of 4 members (Clk1/Sty and Clk2-4). CLKs are dual-specificity kinases, which have the ability to autophosphorylate themselves at tyrosine residues but phosphorylate their substrates exclusively on serine/threonine residues. These kinases phosphorylate serine- and arginine-rich (SR) proteins of the spliceosomal complex like ASF/SF2, SRp40 and SRp55, critical components of splicesosomes (Soret and Tazi, 2003; Stojdl and Bell, 1999). Alternative splicing is a crucial mechanism for generating protein diversity. Different splice variants of a given protein can display different and even antagonistic biological functions. Therefore, appropriate control of their synthesis is required to assure the complex orchestration of cellular processes within multicellular organisms. Mechanisms that alter the accuracy of either constitutive or alternative splicing could have a profound impact on human pathogenesis, in particular in tumor development and progression (Hagiwara, 2005).

Clk kinases were so far shown to be implicated in regulation of alternative splicing of only few genes like tissue factor, VEGF receptor and PKCbeta II kinase. Apart from VEGF splicing, where Clk seem to have rather beneficial role and act in a anti-angiogenic way leading to formation of anti-angiogenic form of VEGF-b, there is no direct evidence in literature on their role in cancer development. There are however indirect reports showing that they might play a role in such cancers like erythroleukemia. In a study by Garcia-Sacristan from 2005 it was shown that Clk/STY, as well as other members of the family (clk2, clk3 and clk4), are up-regulated during HMBA-induced erythroleukemia cell differentiation (Garcia-Sacristan et al., 2005). In a recent article by Jiang et al., it was shown that Akt2, in response to insulin, resulted in phosphorylation of Clk/Sty, which then altered SR protein phosphorylation in concert with Akt2 (Jiang et al., 2009). Apart from its importance in diabetes, the influence of Clk inhibitor on PKC beta splicing can be important in cancer treatment. There is evidence that PKCbeta can contribute in several ways to tumor formation. In addition to direct effects on tumor cells, PKCbeta is involved in tumor host mechanisms such as inflammation and angiogenesis. Elevated expression of PKCbetaII seems to be an early event in colon cancer development and transgenic overexpression of PKCbetaII in the intestine induces hyper-proliferation and an invasive phenotype in epithelial cells by activating beta-catenin/Apc signaling pathway. A study by Abrams demonstrated that overexpression of the PKCbetaII isoform is a feature of CLL (chronic lymphocytic leukemia) cells and that activity of this enzyme strongly correlates with CLL cell response to BCR engagement.

Benzimidazole derivatives substituted with halogens have been previously described as protein kinase inhibitors of IRAK, CK2, DYRK, HIPK and PIM kinases (WO03/030902 A1; WO2005/092866; Gianoncelli et al., 2009; Pagano et al., 2008 and 2004; Andrzejewska et al., 2003). In an article by Pagano, et. al the art described therein teaches about a class of tetrabromobenzimidazole compounds that are substituted with a group of atoms forming an open chain. Embodiments of the present invention, represented by Formulas A and B, adds the novelty of cyclic substituents that are selected from a group of carbocycles and heterocycles which may be saturated, unsaturated, or aromatic, not taught by the Pagano et al., 2004 (see Scheme 1 and Table 1 from Pagano, et. al. 2004). The present invention described herein, represented inter alia by Formulas A and B, is further distinguished from findings of Pagano, et. al 2008, by notable differences observed in the structure activity relationship. Pagano, et. al, teaches that when the substituent on N-1 is other than hydrogen PIM1 receptor binding activity is relatively weaker as can be deduced from comparison of pairs of compounds like K10 with K15 and K25 with K40 (Pagano et al 2008, see Table S2). Whereas, the inventors of the present invention have inter alia demonstrated that when R1 is, for example, ethyl or isopropyl (compounds A and B) PIM1 activity is equally good or better, and such compounds can inhibit or reverse the growth of cancer cells in-vitro and in vivo. Articles by Battistutta, et. al 2005 and Bortolato, et. al 2007 refer to the same class of tetrabromobenzimidazole compounds as described by Pagano, et. al (2004 and 2008) and do not teach anything new. The single exception is a tetrabromobenzimidazole CK2 inhibitor by Bortolato, et. al, which contains a sulfur linked nitrobenzene substituent, and is not described within the scope of this invention (Battistutta et al 2005; Bortolato et al 2007).

BRIEF SUMMARY OF THE INVENTION

The major goal of the present invention is to provide novel derivatives of tetrahalogenated benzimidazoles with more potent anticancer activity in comparison to the previously published compounds and improved potency and specificity towards serine/threonine kinases. The invention also reports on other groups of kinases as new kinase targets of tetrahalogenated benzimidazoles, which were not reported previously and which belong to groups of CDK, FLT, HIPK, CLK, PKG, Haspin, MER, TAO, MNK and TRK kinases. These kinases are new targets of tetrahalogenated benzimidazoles that were to the knowledge of the inventors so far not described in the literature. Thus, examples provided by the prior art (like Pagano et al., 2008, Biochem. J) teach that DMAT and TBB when tested at 1 µM do not inhibit CDK2/cyclin A activity (Table 1 in above publication). In contrast, the inventors of the present invention were inter alia able to show that compounds according to the present invention exert more potent activity in inhibiting kinases exemplified but not limited to CDK kinases (as shown in Table 5 of the present application). Inhibition of these novel targets of tetrahalogenated benzimidazoles may contribute to unexpected and improved anticancer activity of these compounds. Moreover, compounds of the present invention exert improved solubility, bioavailability and metabolic stability and are thus very promising for pharmaceutical development and treatment of diseases like cancer and immunological disorders.

It has inter alia been surprisingly found that compounds of this invention and pharmaceutically acceptable compositions thereof are effective inhibitors of the PIM kinase family, but also other kinases like the CDK, FLT, HIPK, CLK, PKG, Haspin, MER, TAO, MNK and TRK kinases. These compounds exert also improved cytotoxic activity in vitro when tested on a panel of neoplastic cell lines. In contrast to tetrabromobenzimidazole derivatives published in the prior art, which in general did not reach the $ED_{50}$ values below 10 µM for more than 2 or 3 neoplastic cell lines, compounds presented in the application show better cytotoxicity defined as $ED_{50}$ values below 10 µM in at least five different neoplastic cell lines of both hematological and solid tumor origin. This feature will inter alia allow broader therapeutic indication of the compounds from the current application to treat e.g. various cancer types. In addition, one of the technical features that renders further pharmaceutical development and medical use of the tetrabromobenzimidazoles is their very low solubility in physiological solutions and pH above 7, and this feature could also be improved for compounds according to the present invention.

Subject of the present invention are inter alia compounds of formula (A) and (B):

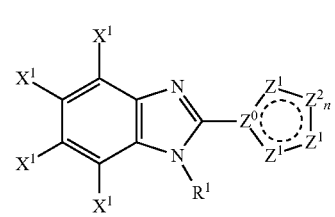

Formula (A)

wherein:
$X^1$ is independently selected at each occurrence from halogen; said halogen group is defined to be F, Cl, or Br;
$Z^0$ is selected from C, CH, and N;
$Z^1$ is independently selected at each occurrence from $CR^2$, $CHR^3$, N, $NR^4$, O, and S;
$Z^2_n$ is independently selected at each occurrence from $CR^2$, $CHR^3$, N, $NR^4$, O, and S;
n is 1, 2, 3, or 4 to form a 5-, 6-, 7-, or 8-membered carbocycle or heterocycle, which may be saturated or unsaturated or aromatic;
$Z^1$ and $Z^2$ may be taken together independently to form fused rings that are 4-, 5-, 6-, or 7-membered carbocycle or heterocycle, which may be saturated or unsaturated or aromatic and which may be substituted with one or more substituents selected from H, halogen, amino, hydroxyl, aminoalkyl, alkoxy, carboxylic acid, carboxyester, carboxamide, carbamate, sulfonic acid, sulfonamide, trifluoromethyl; said 4- to 7-membered heterocyclic groups contain one or more heteroatom(s) selected from N, O, and S;
$R^1$ is selected from the group consisting of H, methyl, oxo, carboxyester, carboxamide, sulfonamide, $—(C_{2-6}alkyl)R_A$, and 5- to 8-membered carbocyclic and heterocyclic groups, which are saturated, unsaturated, or aromatic which may be substituted with one or more substitutents selected from H, halogen, amino, hydroxyl, aminoalkyl, alkoxy, carboxylic acid, carboxyester, carboxamide, carbamate, sulfonic acid, sulfonamide, trifluoromethyl; said 5- to 8-membered heterocyclic groups contain one or more heteroatom(s) selected from N, O, and S, with point of attachment being carbon; said $—(C_{2-6}alkyl)R_A$ may be branched and further substituted with one or more substituent(s) selected from oxo, hydroxyl, and amino;

R$^2$ is independently selected at each occurrence from the group consisting of H, halogen, amino, hydroxyl, oxo, aminoalkyl, alkoxy, carbonyl, carboxylic acid, carboxyester, carboxamide, carbamate, sulfonic acid, sulfonamide, —Y$^1$(C$_{1-6}$alkyl)R$_A$, and Y$^1$R$_B$; said —Y$^1$(C$_{1-6}$alkyl)R$_A$ may be branched and further substituted with one or more substituent(s) selected from oxo, hydroxyl, and amino;

R$^3$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, —Y$^1$(C$_{1-6}$alkyl)R$_A$, and Y$^1$R$_B$; said —Y$^1$(C$_{1-6}$alkyl)R$_A$ may be branched and further substituted with one or more substituent(s) selected from oxo, hydroxyl, and amino;

R$^4$ is independently selected at each occurrence from the group consisting of H, oxo, carboxyester, carboxamide, carbamate, sulfonamide, amidine, —Y$^1$(C$_{1-6}$alkyl)R$_A$, and R$_B$ with the proviso that the point of attachment on R$_B$ is carbon; said —Y$^1$(C$_{1-6}$alkyl)R$_A$ may be branched and further substituted with one or more substituent(s) selected from oxo, hydroxyl, nitrile and amino;

R$_A$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, 5- to 9-membered mono- or bicyclic carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfonamide, trifluoromethyl, substituted or unsubstituted aryl and heteroaryl; said 5- to 9-membered heterocyclic groups contain one or more heteroatom(s) selected from N, O, and S, with point of attachment being carbon or nitrogen;

R$_B$ is independently selected at each occurrence from the group consisting of 5- to 8-membered carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfone, sulfonamide, trifluoromethyl, aryl, heteroaryl; said 5- to 8-membered heterocyclic groups contain one or more heteroatom(s) selected from N, O, and S, with point of attachment being carbon or nitrogen;

Y$^1$ is absent, or independently selected at each occurrence from the group consisting of —C(O)—, —C(O)NH—, —S(O)$_2$—, —S(O)$_2$NH—, —C(O)O—, —C(NH)NH—;

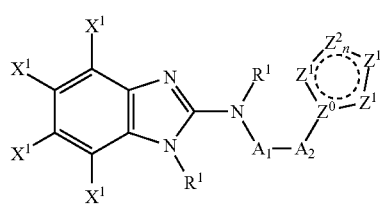

Formula (B)

wherein:

A$_1$ is absent, methylene, carbonyl, thiocarbonyl, or sulfonyl;

A$_2$ is absent, —(C$_{1-6}$alkyl)N(C$_{1-6}$alkyl)- or —(C$_{1-6}$alkyl)R$^0$— which may be branched and further substituted with one or more substituent(s) selected from oxo, hydroxyl, amino, —(C$_{1-6}$alkyl)aminoalkyl, cycloalkyl, aryl, and heteroaryl;

X$^1$ is independently selected at each occurrence from halogen; said halogen group is defined to be F, Cl, or Br;

Z$^0$ is selected from C, CH, and N, with the proviso that when A$_1$ and A$_2$ are both absent Z$^0$ is C or CH;

Z$^1$ is independently selected at each occurrence from CR$^2$, CHR$^3$, N, NR$^4$, O, and S;

Z$^2_n$ is independently selected at each occurrence from CR$^2$, CHR$^3$, N, NR$^4$, O, and S;

n is 1, 2, 3, or 4 to form 5-, 6-, 7-, or 8-membered carbocycle or heterocycle, which may be saturated or unsaturated or aromatic;

Z$^1$ and Z$^2$ may be taken together independently to form fused rings that are 4-, 5-, 6-, or 7-membered carbocycles or heterocycles, which may be saturated or unsaturated or aromatic and which may be substituted with one or more substituents selected from H, halogen, amino, hydroxyl, aminoalkyl, alkoxy, carboxylic acid, carboxyester, carboxamide, carbamate, sulfonic acid, sulfonamide, trifluoromethyl; said 4- to 7-membered heterocyclic groups contain one or more heteroatom(s) selected from N, O, and S;

R$^0$ is absent; or H, amino, hydroxyl, aminoalkyl, aminoalkylamine, alkoxy, aminoalkylamine, carboxylic acid, carboxyester, carboxamide, carbamate, sulfonic acid, sulfonamide, trifluoromethyl with the proviso that Z$^0$ and Z$^1$ and Z$^2_n$ are absent;

R$^1$ is independently selected at each occurrence from the group consisting of H, methyl, oxo, carboxyester, carboxamide, sulfonamide, —(C$_{2-6}$alkyl)R$_A$, and 5- to 8-membered carbocyclic and heterocyclic groups, which are saturated, unsaturated, or aromatic which may be substituted with one or more substitutents selected from H, halogen, amino, hydroxyl, aminoalkyl, alkoxy, carboxylic acid, carboxyester, carboxamide, carbamate, sulfonic acid, sulfonamide, trifluoromethyl; said 5- to 8-membered heterocyclic groups contain one or more heteroatom(s) selected from N, O, and S, with point of attachment being carbon; Said —(C$_{2-6}$alkyl)R$_A$ may be branched and further substituted with one or more substituent(s) selected from oxo, hydroxyl, and amino;

R$^2$ is independently selected at each occurrence from the group consisting of H, halogen, amino, hydroxyl, oxo, aminoalkyl, alkoxy, carbonyl, carboxylic acid, carboxyester, carboxamide, carbamate, sulfonic acid, sulfonamide, —Y$^1$(C$_{1-6}$alkyl)R$_A$, and Y$^1$R$_B$; said —Y$^1$(C$_{1-6}$alkyl)R$_A$ may be branched and further substituted with one or more substituent(s) selected from oxo, hydroxyl, and amino;

R$^3$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, —Y$^1$(C$_{1-6}$alkyl)R$_A$, and Y$^1$R$_B$; said —Y$^1$(C$_{1-6}$alkyl)R$_A$ may be branched and further substituted with one or more substituent(s) selected from oxo, hydroxyl, and amino;

R$^4$ is independently selected at each occurrence from the group consisting of H, oxo, carboxyester, carboxamide, carbamate, sulfonamide, amidine, —Y$^1$(C$_{1-6}$alkyl)R$_A$, and R$_B$ with the proviso that the point of attachment on R$_B$ is carbon; Said —Y$^1$(C$_{1-6}$alkyl)R$_A$ may be branched and further substituted with one or more substituent(s) selected from oxo, hydroxyl, nitrile and amino;

R$_A$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, 5- to 9-membered mono- or bicyclic carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfonamide, trifluoromethyl, substituted or unsubstituted aryl and heteroaryl; said 5- to 9-membered heterocyclic groups contain one or more heteroatom(s) selected from N, O, and S, with point of attachment being carbon or nitrogen;

R$_B$ is independently selected at each occurrence from the group consisting of 5- to 8-membered carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfone, sulfonamide, trifluoromethyl, aryl, heteroaryl; said 5- to 8-membered heterocyclic groups contain one or more heteroatom(s) selected from N, O, and S, with point of attachment being carbon or nitrogen;

Y$^1$ is absent, or independently selected at each occurrence from the group consisting of —C(O)—, —C(O)NH—, —S(O)$_2$—, —S(O)$_2$NH—, —C(O)O—, —C(NH)NH—;

wherein the following structures are excluded from Formula (A) and (B):

2-amino-4,5,6,7-tetrabromo-1H-benzimidazole;
2-methylamino-4,5,6,7-tetrabromo-1H-benzimidazole;
2-dimethylamino-4,5,6,7-tetrabromo-1H-benzimidazole;
2-ethanolamino-4,5,6,7-tetrabromo-1H-benzimidazole;
2-isopropylamino-4,5,6,7-tetrabromo-1H-benzimidazole;
2-(2-hydroxypropylamino)-4,5,6,7-tetrabromo-1H-benzimidazole;
2-(3-hydroxypropylamino)-4,5,6,7-tetrabromo-1H-benzimidazole;
2-(2-dimethylaminoethylamino)-4,5,6,7-tetrabromo-1H-benzimidazole;
2-dimethylamino-4,5,6,7-tetrabromo-1-methyl-benzimidazole;
2-isopropylamino-4,5,6,7-tetrabromo-1-methyl-benzimidazole;
2-(methyl(4,5,6,7-tetrabromo-1-methyl-1H-benzo[d]imidazol-2-yl)amino)ethanol;
(2-dimethylamino-4,5,6,7-tetrabromobenzoimidazol-1-yl)-acetic acid ethyl ester;
(2-dimethylamino-4,5,6,7-tetrabromobenzoimidazol-1-yl)-acetic acid.

In a preferred embodiment, n is 1 to form a 5-membered carbocycle or heterocycle. In another preferred embodiment, n is 2 to form a 6-membered carbocycle or heterocycle. In still another preferred embodiment, n is selected from 1, 2, or 3 to form a 5-, 6-, or 7-membered carbocycle or heterocycle.

In another preferred embodiment, Z$^1$ and Z$^2$ may be taken together independently to form fused rings that are 5-, 6-, or 7-membered carbocycles or heterocycles, which may be saturated or unsaturated or aromatic and which may be substituted as set out above. In still another preferred embodiment, Z$^1$ and Z$^2$ may be taken together to form a second fused ring that is a 5-, 6-, or 7-membered carbocycle or heterocycle, which may be saturated or unsaturated or aromatic and which may be substituted as set out above.

In another preferred embodiment, R$_A$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl and preferably monocyclic 5- to 8-membered carbocyclic and heterocyclic groups, which are saturated, unsaturated, or aromatic and which may be substituted as set out above.

In another preferred embodiment, A$_2$ is absent, or —(C$_{1-6}$alkyl)R$^0$—, which may be branched and further substituted with one or more substituent(s) selected from oxo, hydroxyl, amino, cycloalkyl, aryl, and heteroaryl. In still another preferred embodiment, A$_2$ is absent or —(C$_{1-6}$alkyl)-, which may be branched and substituted as set out above.

In the following, preferred embodiments of the present invention referring to particularly preferred compounds of formula (A) as shown above are listed.

Thus, in a preferred embodiment, the present invention refers to compounds of formula (A) wherein Z$^0$, Z$^1$, Z$^2$ and n are selected such that a substituted or unsubstituted 6-membered carbocycle or heterocycle is formed, which may be saturated or unsaturated or aromatic. Preferably, said substituted or unsubstituted carbocycle or heterocycle is saturated.

In a further preferred embodiment, the present invention refers to compounds of formula (A) wherein Z$^0$, Z$^1$, Z$^2$ and n are selected such that a substituted or unsubstituted 6-membered heterocycle is formed, which may be saturated or unsaturated or aromatic. Preferably, said substituted or unsubstituted heterocycle is saturated. More preferably, said heterocycle comprises two N-heteroatoms. Even more preferably, said heterocycle is unsubstituted or substituted by a single substituent only, which preferably corresponds to R$^4$.

In a further preferred embodiment, the present invention refers to compounds of formula (A) wherein Z$^0$, Z$^1$, Z$^2$ and n are selected such that a substituted or unsubstituted 6-membered heterocycle corresponding to substituted or unsubstituted piperazine is formed. Thus, in such an embodiment, Z$^0$ is N, Z$^1$ is CHR$^3$, n is 2, Z$^2$(1) is CHR$^3$ and Z$^2$(2) is NR$^4$.

In all the above mentioned embodiments it can be preferred that R$^3$ is at each occurrence H or at least one occurrence —Y$^1$(C$_{1-6}$alkyl)R$_A$. If R$^3$ is in said embodiments at least one occurrence —Y$^1$(C$_{1-6}$alkyl)R$_A$, it can be preferred that —Y$^1$ is absent and that R$_A$ is a 6-membered substituted or unsubstituted carbocyclic or heterocyclic group, preferably a substituted or unsubstituted piperazine. It can further be preferred that R$^4$ is H or —Y$^1$(C$_{1-6}$alkyl)R$_A$. If R$^4$ is in said embodiments —Y$^1$(C$_{1-6}$alkyl)R$_A$, it can be preferred that —Y$^1$ is absent and that R$_A$ is a 6-membered substituted or unsubstituted carbocyclic or heterocyclic group, preferably a substituted or unsubstituted piperazine, more preferably an unsubstituted piperazine.

Especially preferred embodiments of the above mentioned embodiments refer to compounds, wherein both R$^3$ and R$^4$ are H at all occurrences.

It can further be preferred in all the above embodiments that X$^1$ is at all occurrences selected from either F, Cl or Br, wherein Br is especially preferred.

It can also be preferred in all the above embodiments that R$^1$ is selected from H, methyl, (C$_{2-6}$alkyl)R$_A$, and saturated 5- to 6-membered carbocyclic groups. H can be particularly preferred. If R$^1$ is in said embodiments (C$_{2-6}$alkyl)R$_A$, it can be particularly preferred that R$_A$ is H and that said alkyl is selected from a substituted or unsubstituted ethyl, propyl, isopropyl and butyl, wherein said alkyl is preferably unsubstituted and most preferably unsubstituted ethyl or isopropyl.

Further objects of the present invention inter alia refer to pharmaceutical compositions comprising compounds (A) and/or (B). Said further objects will be referred to in the detailed description below.

Preferred embodiments of the present invention relate to:
1. A compound of formula (I):

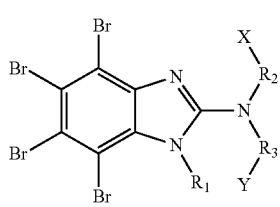

or an enantiomer thereof or a mixture of its enantiomers or its pharmaceutically acceptable salt, or pharmaceutically acceptable prodrugs or pharmaceutically active metabolites, wherein:

$R_1$ is selected from a group consisting of: hydrogen atom, substituted or unsubstituted alkyl or cycloalkyl, substituted or unsubstituted alkenyl or alkynyl, substituted or unsubstituted aryl, substituted or unsubstituted heteroalkyl or heteroaryl;

$R_2$ and $R_3$ are independently selected from a group consisting of: hydrogen atom, substituted or unsubstituted hydrocarbon chain, substituted or unsubstituted cycloalkyl, substituted or unsubstituted aryl, substituted or unsubstituted heteroaryl, substituted or unsubstituted heterocycloalkyl;

X and Y are independently selected from a hydrogen atom, substituted or unsubstituted heteroaryl, guanidinyl, —$NH_2$, —NHR0 or N(R0)$_2$, where R0 represents a substituted or unsubstituted alkyl, aryl or heteroaryl and/or wherein X and Y can also represent a substituted or unsubstituted heterocyclic moiety having 3-10 atoms wherein at least one of the ring atoms is nitrogen or $R_2$ and $R_3$ are connected to form a substituted or unsubstituted heterocycloalkyl, wherein the following structures are excluded:
2-amino-4,5,6,7-tetrabromo-1H-benzimidazole;
2-methylamino-4,5,6,7-tetrabromo-1H-benzimidazole;
2-dimethylamino-4,5,6,7-tetrabromo-1H-benzimidazole;
2-ethanolamino-4,5,6,7-tetrabromo-1H-benzimidazole;
2-isopropylamino-4,5,6,7-tetrabromo-1H-benzimidazole;
2-(2-hydroxypropylamino)-4,5,6,7-tetrabromo-1H-benzimidazole;
2-(3-hydroxypropylamino)-4,5,6,7-tetrabromo-1H-benzimidazole;
2-(2-dimethylaminoethylamino)-4,5,6,7-tetrabromo-1H-benzimidazole;
2-dimethylamino-4,5,6,7-tetrabromo-1-methyl-benzimidazole;
2-isopropylamino-4,5,6,7-tetrabromo-1-methyl-benzimidazole;
2-(methyl(4,5,6,7-tetrabromo-1-methyl-1H-benzo[d]imidazol-2-yl)amino)ethanol;
(2-dimethylamino-4,5,6,7-tetrabromobenzoimidazol-1-yl)-acetic acid ethyl ester;
(2-dimethylamino-4,5,6,7-tetrabromobenzoimidazol-1-yl)-acetic acid.

2. The compound according to 1, characterised in that
$R_1$ is selected among hydrogen atom, substituted or unsubstituted alkyl, cycloalkyl, alkenyl or alkynyl;

$R_2$ is H, and $R_3$ is a $C_2$-$C_5$ alkyl substituted with Y selected from: —$NH_2$, —NH(C=NH)—$NH_2$, —NHR0, —N(R0)$_2$, wherein R0 represents a substituted or unsubstituted alkyl, aryl or heteroaryl.

3. The compound according to 1, characterised in that the compound is preferably selected from:
N1-(4,5,6,7-tetrabromo-1-methyl-1H-benzo[d]imidazol-2-yl)ethane-1,2-diamine;
N1-(4,5,6,7-tetrabromo-1H-benzo[d]imidazol-2-yl)propane-1,3-diamine;
N1-(4,5,6,7-tetrabromo-1-methyl-1H-benzo[d]imidazol-2-yl)propane-1,3-diamine;
N1-(4,5,6,7-tetrabromo-1-isopropyl-1H-benzo[d]imidazol-2-yl)propane-1,3-diamine;
1-(2-(4,5,6,7-tetrabromo-1H-benzo[d]imidazol-2-ylamino)ethyl)guanidine;
1-(3-(4,5,6,7-tetrabromo-1H-benzo[d]imidazol-2-ylamino)propyl)guanidine;
N1,N1-dimethyl-N3-(4,5,6,7-tetrabromo-1H-benzo[d]imidazol-2-yl)propane-1,3-diamine;
N1,N1-dimethyl-N3-(4,5,6,7-tetrabromo-1-methyl-1H-benzo[d]imidazol-2-yl)propane-1,3-diamine;
N1-(4,5,6,7-tetrabromo-1H-benzo[d]imidazol-2-yl)butane-1,4-diamine;
N1-(4,5,6,7-tetrabromo-1-methyl-1H-benzo[d]imidazol-2-yl)butane-1,4-diamine;
N1-(4,5,6,7-tetrabromo-1-isopropyl-1H-benzo[d]imidazol-2-yl)butane-1,4-diamine.

4. The compound according to 1, characterised in that $R_1$ is selected among hydrogen atom, substituted or unsubstituted alkyl, cycloalkyl, alkenyl or alkynyl;

$R_2$ is H, and $R_3$ is a $C_2$-$C_5$ alkyl substituted with Y selected from a substituted or unsubstituted heterocyclic moiety having 3-10 atoms, preferentially the following:

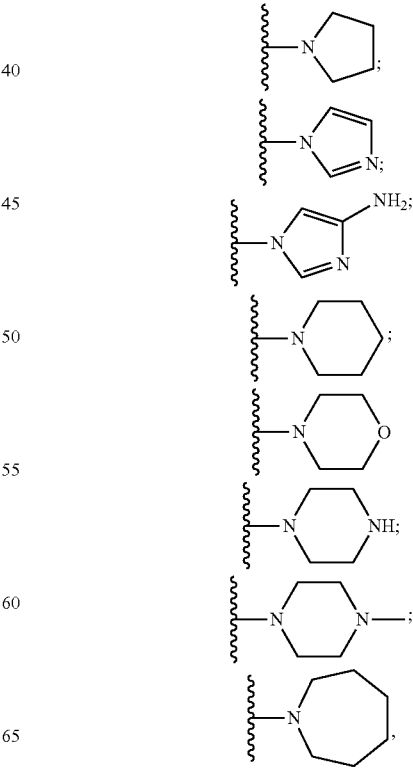

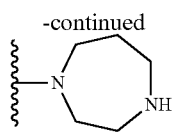

5. The compound according to 4, characterised in that the compound is preferably selected from:
4,5,6,7-tetrabromo-N-(2-(pyrrolidin-1-yl)ethyl)-1H-benzo[d]imidazol-2-amine;
N-(2-(1H-imidazol-1-yl)ethyl)-4,5,6,7-tetrabromo-1H-benzo[d]imidazol-2-amine;
4,5,6,7-tetrabromo-N-(2-(piperidin-1-yl)ethyl)-1H-benzo[d]imidazol-2-amine;
4,5,6,7-tetrabromo-N-(2-morpholinoethyl)-1H-benzo[d]imidazol-2-amine;
4,5,6,7-tetrabromo-N-(2-(piperazin-1-yl)ethyl)-1H-benzo[d]imidazol-2-amine;
N-(2-(azepan-1-yl)ethyl)-4,5,6,7-tetrabromo-1H-benzo[d]imidazol-2-amine;
N-(2-(azepan-1-yl)ethyl)-4,5,6,7-tetrabromo-1-methyl-1H-benzo[d]imidazol-2-amine;
N-(2-(1,4-diazepan-1-yl)ethyl)-4,5,6,7-tetrabromo-1H-benzo[d]imidazol-2-amine;
N-(2-(1,4-diazepan-1-yl)ethyl)-4,5,6,7-tetrabromo-1-methyl-1H-benzo[d]imidazol-2-amine;
N-(2-(1,4-diazepan-1-yl)ethyl)-4,5,6,7-tetrabromo-1-isopropyl-1H-benzo[d]imidazol-2-amine.

6. The compound according to 1, characterised in that
$R_1$ is selected from hydrogen atom, substituted or unsubstituted alkyl, cycloalkyl, alkenyl or alkynyl;
$R_2$ and $R_3$ are independently selected from $C_{2-5}$ alkyl optionally substituted with X and/or Y selected from: $-NH_2$, $-NH(C=NH)-NH_2$, $-NHR0$, $-N(R0)_2$, where R0 represents a substituted or unsubstituted alkyl, aryl or heteroaryl, and wherein the compound is preferably selected from:
N1-ethyl-N1-(4,5,6,7-tetrabromo-1H-benzo[d]imidazol-2-yl)ethane-1,2-diamine;
N1-(2-aminoethyl)-N1-(4,5,6,7-tetrabromo-1H-benzo[d]imidazol-2-yl)ethane-1,2-diamine;
N1-(2-aminoethyl)-N1-(4,5,6,7-tetrabromo-1-methyl-1H-benzo[d]imidazol-2-yl)ethane-1,2-diamine;
N1-ethyl-N1-(4,5,6,7-tetrabromo-1H-benzo[d]imidazol-2-yl)propane-1,3-diamine;
N1-(3-aminopropyl)-N1-(4,5,6,7-tetrabromo-1H-benzo[d]imidazol-2-yl)propane-1,3-diamine;
N1-(3-aminopropyl)-N3,N3-dimethyl-N1-(4,5,6,7-tetrabromo-1H-benzo[d]imidazol-2-yl)propane-1,3-diamine;
N1-(3-aminopropyl)-N3,N3-dimethyl-N1-(4,5,6,7-tetrabromo-1-methyl-1H-benzo[d]imidazol-2-yl)propane-1,3-diamine;
1-(3-((3-(dimethylamino)propyl)(4,5,6,7-tetrabromo-1H-benzo[d]imidazol-2-yl)amino)propyl)guanidine;
1-(3-((3-(dimethylamino)propyl)(4,5,6,7-tetrabromo-1-methyl-1H-benzo[d]imidazol-2-yl)amino)propyl)guanidine.

7. The compound according to 1, characterised in that
$R_1$ is selected from hydrogen atom, substituted or unsubstituted alkyl, cycloalkyl, alkenyl or alkynyl;
$R_2$ is H, and $R_3$ is selected from substituted or unsubstituted aryl or substituted or unsubstituted heteroaryl, and wherein the compound is preferably selected from:
4,5,6,7-tetrabromo-N-phenyl-1H-benzo[d]imidazol-2-amine;
4,5,6,7-tetrabromo-1-methyl-N-phenyl-1H-benzo[d]imidazol-2-amine;
N1-(4,5,6,7-tetrabromo-1H-benzo[d]imidazol-2-yl)benzene-1,4-diamine;
N1-(4,5,6,7-tetrabromo-1-methyl-1H-benzo[d]imidazol-2-yl)benzene-1,4-diamine;
N1,N1-dimethyl-N4-(4,5,6,7-tetrabromo-1H-benzo[d]imidazol-2-yl)benzene-1,4-diamine;
N1,N1-dimethyl-N4-(4,5,6,7-tetrabromo-1-methyl-1H-benzo[d]imidazol-2-yl)benzene-1,4-diamine.

8. The compound according to 1, characterised in that $R_1$ is selected among hydrogen atom, substituted or unsubstituted alkyl, cycloalkyl, alkenyl or alkynyl, and $R_2$ and $R_3$ are connected to a substituted or unsubstituted heterocycloalkyl, and wherein the compound is preferably selected from:
4,5,6,7-tetrabromo-2-(pyrrolidin-1-yl)-1H-benzo[d]imidazole;
4,5,6,7-tetrabromo-2-(piperidin-1-yl)-1H-benzo[d]imidazole;
4-(4,5,6,7-tetrabromo-1H-benzo[d]imidazol-2-yl)morpholine;
4,5,6,7-tetrabromo-2-(piperazin-1-yl)-1H-benzo[d]imidazole;
4,5,6,7-tetrabromo-2-(4-methylpiperazin-1-yl)-1H-benzo[d]imidazole;
4,5,6,7-tetrabromo-1-methyl-2-(4-methylpiperazin-1-yl)-1H-benzo[d]imidazole;
4,5,6,7-tetrabromo-1-isopropyl-2-(4-methylpiperazin-1-yl)-1H-benzo[d]imidazole.

9. A compound according to any of [0176] to 8, characterized in that pharmaceutically acceptable salt is selected preferably from the group consisting of hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate and the like.

10. A pharmaceutical composition, comprising a therapeutically effective amount of at least one compound selected from the group consisting of compounds as mentioned in any one of [0176] to 9 and optionally comprising a therapeutic agent selected from a chemotherapeutic or anti-proliferative agent, an immunomodulatory or immunosuppressive agent, or an anti-inflammatory agent.

11. A pharmaceutical composition, according to 10, characterized in that the therapeutically effective amount provided in the treatment is administered in an amount of about 0.01 to 1,000 mg/kg at least once a day for the duration of the treatment.

12. A pharmaceutical composition, according to 10, characterized in that the said composition optionally comprises a therapeutic agent selected from a chemotherapeutic or anti-proliferative agent, an immunomodulatory or immunosuppressive agent, or an anti-inflammatory agent.

13. A pharmaceutical composition, according to 10 or 11, characterized in that said composition is administered parenterally, vaginally, rectally, transdermally, orally or through the otolaryngologal sphere.

14. A pharmaceutical composition, according to 10 or 11, characterized in that it further comprises a pharmaceutically acceptable carrier selected from the group consisting of flavoring agents, sweetener, lubricants, solubilizers, suspending agents, fillers, glidants, compression aides, binders, tablet-disintegrating agents, effervescing agent, wetting agent encapsulating materials, dyestuff, and mixtures thereof wherein carrier is chosen from solid or liquid carriers, whether sterile or not.

15. A pharmaceutical composition, according to 10 or 11, characterized in that said composition is a sterile solution or suspension suitable for parenteral administration, including but not limited to intramuscular, intraperitoneal, intravenous, intrathecal or subcutaneous injection or perfusion.

16. A pharmaceutical composition, according to 10 or 11, characterized in that suitable for oral administration either liquid or solid composition form, including pills, tablets, capsules, sachets, dragees, powders, granules, lozenges, powders for reconstitution, orally disintegrating tablet, films, osmotic controlled release capsule, elixir, emulsion, syrup, suspension, tincture, solutions or powder for inhalation and nebulization, or sublingual administration.

17. A pharmaceutical composition, according to 10 or 15, characterized in that said composition is a formulation for transdermal, rectal, vaginal administration, including ointments, creams, lotions, liniments, gels, paste, films, suppositories, enemas and pessaries.

18. A pharmaceutical composition, according to 10 or 11, characterized in that said composition is a formulation for administration through the eyes, ears and nose.

19. A pharmaceutical composition, according to 10 or 11, characterized in that the composition is an immediate, extended or slow-release formulation.

20. A pharmaceutical composition, according to 10 or 11, characterized in that the therapeutically effective amount is provided in the treatment of a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

21. A pharmaceutical composition according to 10 or 11 for the prevention or treatment of neoplastic conditions, especially related with the modulation or regulation of serine/threonine kinases, preferably selected from the group of Pim, HIPK, DYRK and CLK kinases.

22. Use of the compound of Formula I for the preparation of a pharmaceutical composition comprising a therapeutically effective amount of at least one compound selected from the group consisting of compounds as mentioned in any one of [0176] to 9 and optionally comprising a therapeutic agent selected from a chemotherapeutic or anti-proliferative agent, an immunomodulatory or immunosuppressive agent, or an anti-inflammatory agent.

23. Use according to 22 for the prevention or treatment of neoplastic or immune conditions, especially related with the modulation or regulation of serine/threonine kinases, preferably selected from the group of Pim, HIPK, DYRK and CLK.

24. Use according to 22 or 23 for preventing or treating neoplastic conditions selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

25. A method for modulating or regulating serine/threonine kinases, preferably selected from the group of Pim, HIPK, DYRK and CLK kinases, wherein serine/threonine kinases are exposed to an effective amount of at least one compound of Formula I, an enantiomer thereof or a mixture of its enantiomers or pharmaceutically acceptable salts of compounds of Formula I or pharmaceutically acceptable prodrugs of compounds of Formula I, or pharmaceutically active metabolites of compounds of Formula I as mentioned in any one of [0176] to 9.

26. A method according to 25, characterized in that serine/threonine kinases, preferably kinases selected from the group of Pim, HIPK, DYRK and CLK kinases is in a subject with a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

27. A serine/threonine kinases modulating agent as mentioned in any one of [0176] to 9, characterized in that serine/threonine kinases are preferably selected from the group of Pim, HIPK, DYRK and CLK kinases wherein serine/threonine kinases are exposed to an effective amount of at least one compound of Formula I, an enantiomer thereof or a mixture of its enantiomers or pharmaceutically acceptable salts of compounds of Formula I or pharmaceutically acceptable prodrugs of compounds of Formula I, or pharmaceutically active metabolites of compounds of Formula I as mentioned in any one of [0176] to 9.

28. An agent according to 27, characterized in that serine/threonine or tyrosine kinases are preferably kinases selected from the group of Pim, HIPK, DYRK and CLK and their isoforms is in a subject with a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

29. Process for the preparation of a compound according to any one of 1 to 9 characterised in that the process comprise: reacting of a corresponding, unsubstituted or substituted 2,4,5,6,7-pentabromo-benzimidazole with a suitable amine at elevated temperature, wherein the reactive substituents X and/or Y are optionally protected with suitable protecting groups and wherein the resulting product is subjected to purification by crystallization or chromatography according to the reaction

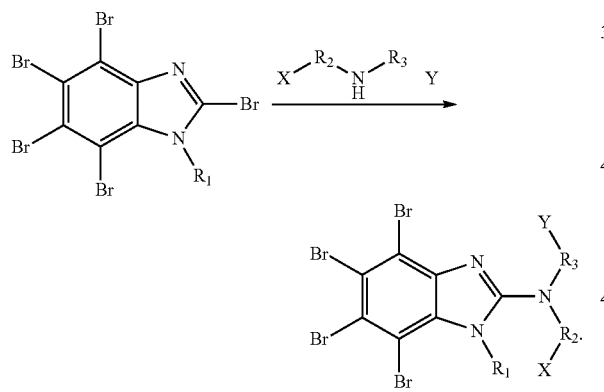

Still further preferred embodiments of the present invention relate to:

1. A compound of formula (A) and (B):

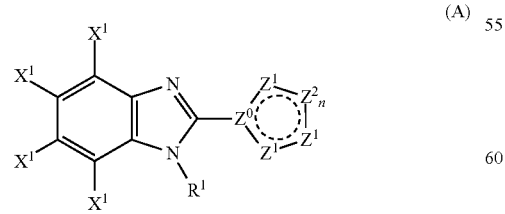

wherein:
$X^1$ is independently selected at each occurrence from halogen. Said halogen group is defined to be F, Cl, or Br;
$Z^0$ is selected from C, CH, and N;
$Z^1$ is independently selected at each occurrence from $CR^2$, $CHR^3$, N, $NR^4$, O, and S;
$Z^2_n$ is independently selected at each occurrence from $CR^2$, $CHR^3$, N, $NR^4$, O, and S;
n is 1, 2, 3, or 4 to form 5-, 6-, 7-, or 8-membered carbocycle or heterocycle, which may be saturated or unsaturated or aromatic;
$Z^1$ and $Z^2$ may be taken together independently to form a fused rings that are 5-, 6-, or 7-membered carbocycles or heterocycles, which may be saturated or unsaturated or aromatic and which may be substituted with one or more substituents selected from H, halogen, amino, hydroxyl, aminoalkyl, alkoxy, carboxylic acid, carboxyester, carboxamide, carbamate, sulfonic acid, sulfonamide, trifluoromethyl; said 5- to 7-membered heterocyclic groups contain one or more heteroatom(s) selected from N, O, and S;
$R^1$ is selected from the group consisting of H, methyl, oxo, carboxyester, carboxamide, sulfonamide, —($C_{2-6}$alkyl)$R_A$, and 5- to 8-membered carbocyclic and heterocyclic groups, which are saturated, unsaturated, or aromatic which may be substituted with one or more substitutents selected from H, halogen, amino, hydroxyl, aminoalkyl, alkoxy, carboxylic acid, carboxyester, carboxamide, carbamate, sulfonic acid, sulfonamide, trifluoromethyl; said 5- to 8-membered heterocyclic groups contain one or more heteroatom(s) selected from N, O, and S, with point of attachment being carbon; said —($C_{2-6}$alkyl)$R_A$ may be branched and further substituted with one or more substituent(s) selected from oxo, hydroxyl, and amino;
$R^2$ is independently selected at each occurrence from the group consisting of H, halogen, amino, hydroxyl, oxo, aminoalkyl, alkoxy, carbonyl, carboxylic acid, carboxyester, carboxamide, carbamate, sulfonic acid, sulfonamide, —$Y^1$($C_{1-6}$alkyl)$R_A$, and $Y^1R_B$; said —$Y^1$($C_{1-6}$alkyl)$R_A$ may be branched and further substituted with one or more substituent(s) selected from oxo, hydroxyl, and amino;
$R^3$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, —$Y^1$($C_{1-6}$alkyl)$R_A$, and $Y^1R_B$; said —$Y^1$($C_{1-6}$alkyl)$R_A$ may be branched and further substituted with one or more substituent(s) selected from oxo, hydroxyl, and amino;
$R^4$ is independently selected at each occurrence from the group consisting of H, oxo, carboxyester, carboxamide, carbamate, sulfonamide, amidine, —$Y^1$($C_{1-6}$alkyl)$R_A$, and $R_B$ with the proviso that the point of attachment on $R_B$ is carbon; said —$Y^1$($C_{1-6}$alkyl)$R_A$ may be branched and further substituted with one or more substituent(s) selected from oxo, hydroxyl, nitrile and amino;
$R_A$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, 5- to 8-membered carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfonamide, trifluoromethyl, aryl, heteroaryl; said 5- to 8-membered heterocyclic groups contain one or more heteroatom(s) selected from N, O, and S, with point of attachment being carbon or nitrogen;

$R_B$ is independently selected at each occurrence from the group consisting of 5- to 8-membered carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfonamide, trifluoromethyl, aryl, heteroaryl; said 5- to 8-membered heterocyclic groups contain one or more heteroatom(s) selected from N, O, and S, with point of attachment being carbon or nitrogen;

$Y^1$ is absent, or independently selected at each occurrence from the group consisting of —C(O)—, —C(O)NH—, —S(O)$_2$—, —S(O)$_2$NH—, —C(O)O—, —C(NH)NH—;

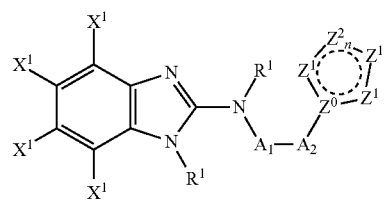

(B)

wherein:

$A_1$ is absent, methylene, carbonyl, thiocarbonyl, or sulfonyl;

$A_2$ is absent, or —(C$_{1-6}$alkyl)R$^0$— which may be branched and further substituted with one or more substituent(s) selected from oxo, hydroxyl, amino, cycloalkyl, aryl, and heteroaryl;

$X^1$ is independently selected at each occurrence from halogen; said halogen group is defined to be F, Cl, or Br;

$Z^0$ is selected from C, CH, and N, with the proviso that when $A_1$ and $A_2$ are both absent $Z^0$ is C or CH;

$Z^1$ is independently selected at each occurrence from CR$^2$, CHR$^3$, N, NR$^4$, O, and S;

$Z^2_n$ is independently selected at each occurrence from CR$^2$, CHR$^3$, N, NR$^4$, O, and S;

n is 1, 2, 3, or 4 to form 5-, 6-, 7-, or 8-membered carbocycle or heterocycle, which may be saturated or unsaturated or aromatic;

$Z^1$ and $Z^2$ may be taken together to independently form a fused second and optionally third ring which can be a 5-, 6-, or 7-membered carbocycle or heterocycle, which may be saturated or unsaturated or aromatic and which may be substituted with one or more substituents selected from H, halogen, amino, hydroxyl, aminoalkyl, alkoxy, carboxylic acid, carboxyester, carboxamide, carbamate, sulfonic acid, sulfonamide, trifluoromethyl; said 5- to 7-membered heterocyclic groups contain one or more heteroatom(s) selected from N, O, and S;

$R^0$ is absent; or H, amino, hydroxyl, aminoalkyl, aminoalkylamine, alkoxy, aminoalkylamine, carboxylic acid, carboxyester, carboxamide, carbamate, sulfonic acid, sulfonamide, trifluoromethyl with the proviso that $Z^0$ and $Z^1$ and $Z^2_n$ are absent;

$R^1$ is independently selected at each occurrence from the group consisting of H, methyl, oxo, carboxyester, carboxamide, sulfonamide, —(C$_{2-6}$alkyl)R$_A$, and 5- to 8-membered carbocyclic and heterocyclic groups, which are saturated, unsaturated, or aromatic which may be substituted with one or more substitutents selected from H, halogen, amino, hydroxyl, aminoalkyl, alkoxy, carboxylic acid, carboxyester, carboxamide, carbamate, sulfonic acid, sulfonamide, trifluoromethyl; said 5- to 8-membered heterocyclic groups contain one or more heteroatom(s) selected from N, O, and S, with point of attachment being carbon; Said —(C$_{2-6}$alkyl)R$_A$ may be branched and further substituted with one or more substituent(s) selected from oxo, hydroxyl, and amino;

$R^2$ is independently selected at each occurrence from the group consisting of H, halogen, amino, hydroxyl, oxo, aminoalkyl, alkoxy, carbonyl, carboxylic acid, carboxyester, carboxamide, carbamate, sulfonic acid, sulfonamide, —Y$^1$(C$_{1-6}$alkyl)R$_A$, and Y$^1$R$_B$; said —Y$^1$(C$_{1-6}$alkyl)R$_A$ may be branched and further substituted with one or more substituent(s) selected from oxo, hydroxyl, and amino;

$R^3$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, —Y$^1$(C$_{1-6}$alkyl)R$_A$, and Y$^1$R$_B$; said —Y$^1$(C$_{1-6}$alkyl)R$_A$ may be branched and further substituted with one or more substituent(s) selected from oxo, hydroxyl, and amino;

$R^4$ is independently selected at each occurrence from the group consisting of H, oxo, carboxyester, carboxamide, carbamate, sulfonamide, amidine, —Y$^1$(C$_{1-6}$alkyl)R$_A$, and R$_B$ with the proviso that the point of attachment on R$_B$ is carbon; Said —Y$^1$(C$_{1-6}$alkyl)R$_A$ may be branched and further substituted with one or more substituent(s) selected from oxo, hydroxyl, nitrile and amino;

$R_A$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, 5- to 8-membered carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfonamide, trifluoromethyl, aryl, heteroaryl; said 5- to 8-membered heterocyclic groups contain one or more heteroatom(s) selected from N, O, and S, with point of attachment being carbon or nitrogen;

$R_B$ is independently selected at each occurrence from the group consisting of 5- to 8-membered carbocyclic and heterocyclic groups, which are saturated, unsaturated, or aromatic which may be substituted with one or more substitutents selected from H, halogen, amino, hydroxyl, alkyl, aminoalkyl, alkoxy, carboxylic acid, carboxyester, carboxamide, carbamate, sulfonic acid, sulfonamide, trifluoromethyl, aryl, heteroaryl; said 5- to 8-membered heterocyclic groups contain one or more heteroatom(s) selected from N, O, and S, with point of attachment being carbon or nitrogen;

$Y^1$ is absent, or independently selected at each occurrence from the group consisting of —C(O)—, —C(O)NH—, —S(O)$_2$—, —S(O)$_2$NH—, —C(O)O—, —C(NH)NH—;

or an enantiomer thereof or a mixture of its enantiomers or its pharmaceutically acceptable salt, or pharmaceutically acceptable prodrugs or pharmaceutically active metabolites wherein the following structures are excluded:

2-amino-4,5,6,7-tetrabromo-1H-benzimidazole;

2-methylamino-4,5,6,7-tetrabromo-1H-benzimidazole;

2-dimethylamino-4,5,6,7-tetrabromo-1H-benzimidazole;
2-ethanolamino-4,5,6,7-tetrabromo-1H-benzimidazole;
2-isopropylamino-4,5,6,7-tetrabromo-1H-benzimidazole;
2-(2-hydroxypropylamino)-4,5,6,7-tetrabromo-1H-benzimidazole;
2-(3-hydroxypropylamino)-4,5,6,7-tetrabromo-1H-benzimidazole;
2-(2-dimethylaminoethylamino)-4,5,6,7-tetrabromo-1H-benzimidazole;
2-dimethylamino-4,5,6,7-tetrabromo-1-methyl-benzimidazole;
2-isopropylamino-4,5,6,7-tetrabromo-1-methyl-benzimidazole;
2-(methyl(4,5,6,7-tetrabromo-1-methyl-1H-benzo[d]imidazol-2-yl)amino)ethanol;
(2-dimethylamino-4,5,6,7-tetrabromobenzoimidazol-1-yl)-acetic acid ethyl ester;
(2-dimethylamino-4,5,6,7-tetrabromobenzoimidazol-1-yl)-acetic acid.

2. A compound according to [0176], characterized in that pharmaceutically acceptable salt is selected preferably from the group consisting of hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate and the like.

3. A pharmaceutical composition, comprising a therapeutically effective amount of at least one compound selected from the group consisting of compounds as mentioned in any one of [0176] to 2 and optionally comprising a therapeutic agent selected from a chemotherapeutic or anti-proliferative agent, an immunomodulatory or immunosuppressive agent, or an anti-inflammatory agent.

4. A pharmaceutical composition, according to 3, characterized in that the therapeutically effective amount provided in the treatment is administered in an amount of about 0.01 to 1.000 mg/kg at least once a day for the duration of the treatment.

5. A pharmaceutical composition, according to 3, characterized in that the said composition optionally comprises a therapeutic agent selected from a chemotherapeutic or anti-proliferative agent, an immunomodulatory or immunosuppressive agent, or an anti-inflammatory agent.

6. A pharmaceutical composition, according to 3, characterized in that said composition is administered parenterally, vaginally, rectally, transdermally, orally or through the otolaryngologal sphere.

7. A pharmaceutical composition, according to 3, characterized in that it further comprises a pharmaceutically acceptable carrier selected from the group consisting of flavoring agents, sweetener, lubricants, solubilizers, suspending agents, fillers, glidants, compression aides, binders, tablet-disintegrating agents, effervescing agent, wetting agent encapsulating materials, dyestuff, and mixtures thereof wherein carrier is chosen from solid or liquid carriers, whether sterile or not.

8. A pharmaceutical composition, according to 3, characterized in that said composition is a sterile solution or suspension suitable for parenteral administration, including but not limited to intramuscular, intraperitoneal, intravenous, intrathecal or subcutaneous injection or perfusion.

9. A pharmaceutical composition, according to 3, characterized in that suitable for oral administration either liquid or solid composition form, including pills, tablets, capsules, sachets, dragees, powders, granules, lozenges, powders for reconstitution, orally disintegrating tablet, films, osmotic controlled release capsule, elixir, emulsion, syrup, suspension, tincture, solutions or powder for inhalation and nebulization, or sublingual administration.

10. A pharmaceutical composition, according to 3 or 9, characterized in that said composition is a formulation for transdermal, rectal, vaginal administration, including ointments, creams, lotions, liniments, gels, paste, films, suppositories, enemas and pessaries.

11. A pharmaceutical composition, according to 3 or 4, characterized in that said composition is a formulation for administration through the eyes, ears and nose.

12. A pharmaceutical composition, according to 3 or 4, characterized in that the composition is an immediate, extended or slow-release formulation.

13. A pharmaceutical composition, according to 3 or 4, characterized in that the therapeutically effective amount is provided in the treatment of a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

14. A pharmaceutical composition according to 3 or 4 for the prevention or treatment of neoplastic conditions, especially related with the modulation or regulation of serine/threonine or tyrosine kinases, preferably selected from the group of PIM, HIPK, DYRK, CLK, CDK, FLT, PKG, Haspin, MER, TAO, MNK, TRK kinases.

15. Use of the compound of Formula A and B for the preparation of a pharmaceutical composition comprising a therapeutically effective amount of at least one compound selected from the group consisting of compounds as mentioned in any one of 1 to 2 and optionally comprising a therapeutic agent selected from a chemotherapeutic or antiproliferative agent, an immunomodulatory or immunosuppressive agent, or an anti-inflammatory agent.

16. Use according to 15 for the prevention or treatment of neoplastic or immune conditions, especially related with the modulation or regulation of serine/threonine or tyrosine kinases, preferably selected from the group of PIM, HIPK, DYRK, CLK, FLT, PKG, Haspin, MER, TAO, MNK, TRK kinases.

17. Use according to 15 or 16 for preventing or treating neoplastic conditions selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, adenocarcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

18. A method for modulating or regulating serine/threonine or tyrosine kinases, preferably selected from the group of PIM, HIPK, DYRK, CLK, CDK, FLT, PKG, Haspin, MER, TAO, MNK, TRK kinases, wherein serine/threonine kinases are exposed to an effective amount of at least one compound of Formula A and B, an enantiomer thereof or a mixture of its enantiomers or pharmaceutically acceptable salts of compounds of Formula A and B or pharmaceutically acceptable prodrugs of compounds of Formula A and B, or pharmaceutically active metabolites of compounds of Formula A and B as mentioned in any one of [0176] to 2.

19. A method according to 18, characterized in that serine/threonine or tyrosine kinases, preferably kinases selected from the group of PIM, HIPK, DYRK, CLK, CDK, FLT, PKG, Haspin, MER, TAO, MNK, TRK kinases is in a subject with a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

20. A serine/threonine or tyrosine kinases modulating agent as mentioned in any one of [0176] to 2, characterized in that serine/threonine or tyrosine kinases are preferably selected from the group of PIM, HIPK, DYRK, CLK, CDK, FLT, PKG, Haspin, MER, TAO, MNK, TRK kinases wherein serine/threonine or tyrosine kinases are exposed to an effective amount of at least one compound of Formula A and B, an enantiomer thereof or a mixture of its enantiomers or pharmaceutically acceptable salts of compounds of Formula A and B or pharmaceutically acceptable prodrugs of compounds of Formula A and B, or pharmaceutically active metabolites of compounds of Formula A and B as mentioned in any one of [0176] to 2.

21. An agent according to 20, characterized in that serine/threonine or tyrosine kinases are preferably kinases selected from the group of PIM, HIPK, DYRK, CLK, CDK, FLT, PKG, Haspin, MER, TAO, MNK, TRK kinases and their isoforms is in a subject with a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

22. Process for the preparation of a compound according to any one of 1 to 2 characterised in that the process comprise: reacting of a corresponding, unsubstituted or substituted 2,4,5,6,7-pentahalogenobenzimidazole with a suitable amine at elevated temperature, wherein the reactive substituents are optionally protected with suitable protecting groups and wherein the resulting product is subjected to purification by crystallization or chromatography according to the reaction.

DETAILED DESCRIPTION OF THE INVENTION

Figure 1:
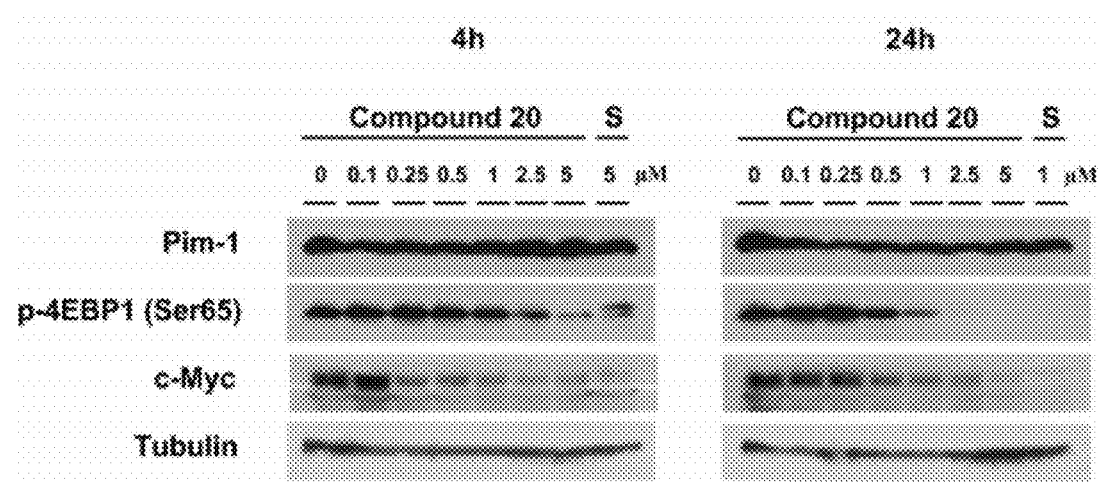
FIG. 1 shows the inhibition of biomarkers as indicated on the left side (Pim1 as expression control, p-4EBP1, c-myc and as negative control tubulin) in MV411 cells after 4 h and 24 h treatment with compound 20 in the concentrations as indicated above each lane of the Western blot, S corresponds to Sunitinib. Standard antibodies against the indicated biomarkers were used in the Western blots.

The following is a list of definitions for terms used herein.
"Alkyl" is a saturated hydrocarbon chain having 1 to 15 carbon atoms, preferably 1 to 10, more preferably 1 to 4 carbon atoms. It is, however, clear to the skilled person that an indication of the number of carbon atoms in connection with the term "alkyl" refers to a hydrocarbon chain having the indicated number of carbon atoms; thus, e.g. "C$_{1-6}$alkyl" means that said hydrocarbon chain has 1 to 6 carbon atoms. "Alkenyl" is a hydrocarbon chain having at least one (preferably only one) carbon-carbon double bond and having 2 to 15 carbon atoms, preferably 2 to 10, more preferably 2 to 4 carbon atoms. "Alkynyl" is a hydrocarbon chain having at least one (preferably only one) carbon-carbon triple bond and having 2 to 15 carbon atoms, preferably 2 to 10, more preferably 2 to 4 carbon atoms. Alkyl, alkenyl and alkynyl chains (referred to collectively as "hydrocarbon chains") may be straight or branched and may be unsubstituted or substituted. Preferred branched alkyl, alkenyl and alkynyl chains have one or two branches, preferably one branch. Preferred chains are alkyl. Alkyl, alkenyl and alkynyl hydrocarbon chains each may be unsubstituted or substituted with from 1 to 4 substituents; when substituted, preferred chains are mono-, di-, or tri-substituted. Alkyl, alkenyl and alkynyl hydrocarbon chains each may be substituted with halo, hydroxy, aryloxy (e.g. phenoxy), heteroaryloxy, acyloxy (e.g. acetoxy), carboxy, aryl (e.g. phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, and butenyl.

Also, as referred to herein, a "lower" alkyl, alkenyl or alkynyl moiety (e.g. "lower alkyl") is a chain comprised of 1 to 6, preferably from 1 to 4, carbon atoms in the case of alkyl and 2 to 6, preferably 2 to 4, carbon atoms in the case of alkenyl and alkynyl.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloalkyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e. —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member 60 atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxyl, carboxy, amino, acylamino, alkyl, heteroalkyl, phenyl, alkoxy, aryloxy, heteroaryloxy, or any combination thereof.

Preferred heteroaryl rings include, but are not limited to, the following:

Furan

Thiophene

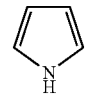

Pyrrole

Pyrazole

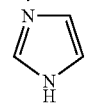

Imidazole

Oxazole

Isoxazole

Isothiazole

Thiazole

1,2,3-Triazole

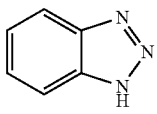
Benzotriazole

Pyridine

Pyridazine

Pyrimidine

Pyrazine

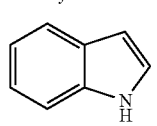
Indole

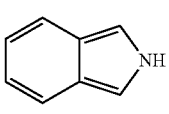
Isoindole

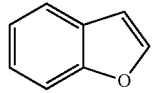
Benzofuran

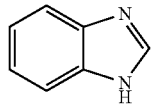
Benzimidazole

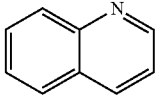
Quinoline

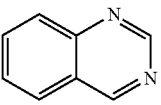
Quinazoline

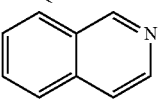
Isoquinoline

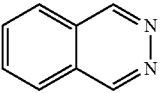
Pthtalazine

"$C_{1-6}$alkyl" is straight, branched, or cyclic and is saturated or unsaturated.

"Halogen" is fluorine, chlorine, or bromine.

"Aminoalkyl" is —NH($C_{1-6}$alkyl), or —N($C_{1-6}$alkyl)$_2$ or a quaternized amine, i.e. —N($C_{1-6}$alkyl)$_3$.

"Alkoxy" is —O($C_{1-6}$alkyl).

"Carboxylic acid" is —C(O)OH.

"Carboxy" is —C(O)O—.

"Carboxyester" is —C(O)O($C_{1-6}$alkyl).

"Carboxamide" is —C(O)NH—, —C(O)N($C_{1-6}$alkyl)-.

"Carbamate" is —OC(O)NH—, —OC(O)N($C_{1-6}$alkyl)-.

"Sulfonic acid" is —S(O)$_2$OH.

"Sulfonamide" is —S(O)$_2$NH—, or —S(O)$_2$N($C_{1-6}$alkyl)-.

"Oxo" is —O—.

"Carbonyl" is —C(O)—.

"Aminoalkylamine" is —NH($C_{1-6}$alkyl)NH($C_{1-6}$alkyl), or —NH($C_{1-6}$alkyl)N($C_{1-6}$alkyl)$_2$.

"Aminoalkylalkoxy" is —NH($C_{1-6}$alkyl)O($C_{1-6}$alkyl), —O($C_{1-6}$alkyl)NH($C_{1-6}$alkyl), —O($C_{1-6}$alkyl)N($C_{1-6}$alkyl)$_2$.

"Amidine" is —C(NH)NH$_2$.

"Nitrile" is —CN.

"Sulfone" is an optionally cyclic structure of —($C_{1-6}$alkyl)S(O)$_2$($C_{1-6}$alkyl).

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, Spiro, or bridged ring systems. Preferred bicyclic heterocycloalkyl rings comprise 5-, 6- or 7-membered rings fused to 5-, 6-, or 7-membered rings.

Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

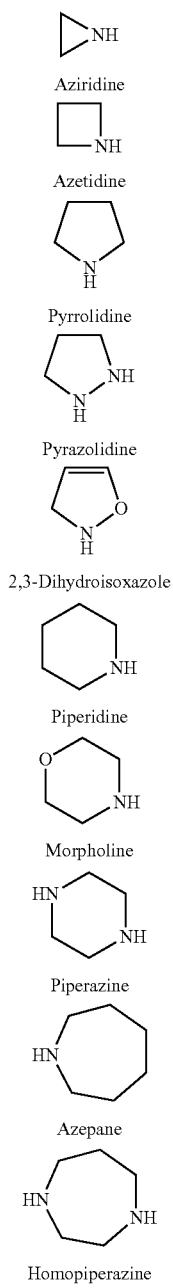

Aziridine

Azetidine

Pyrrolidine

Pyrazolidine 2,3-Dihydroisoxazole

Piperidine

Morpholine

Piperazine

Azepane

Homopiperazine

While alkyl, heteroalkyl, cycloalkyl, and heterocycloalkyl groups may be substituted with hydroxy, amino, and amido groups as stated above, the following are not envisioned in the invention:

Enols (OH attached to a carbon bearing a double bond).

Amino groups attached to a carbon bearing a double bond (except for vinylogous amides).

More than one hydroxy, amino, or amido attached to a single carbon (except where two nitrogen atoms are attached to a single carbon atom and all three atoms are member atoms within a heterocycloalkyl ring).

Hydroxy, amino, or amido attached to a carbon that also has a heteroatom attached to it.

Hydroxy, amino, or amido attached to a carbon that also has a halogen attached to it.

Some of the compounds disclosed herein may contain one or more asymmetric centers and may thus lead to enantiomers, diastereomers, and other stereoisomeric forms.

The present invention is also meant to encompass all such possible forms as well as their racemic and resolved forms and mixtures thereof, unless specified otherwise. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers). The term "chiral center" refers to a carbon atom to which four different groups are attached. The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction. The term "racemic" refers to a mixture of equal parts of enantiomers and which is optically inactive. The term "resolution" refers to the separation or concentration or depletion of one of the two enantiomeric forms of a molecule.

As used in the specification and the claims, the singular forms of "a" and "an" also include the corresponding plurals unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The invention also relates to pharmaceutically acceptable prodrugs of the compounds described herein, and methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g. a prodrug on being brought to physiological pH is converted to the compound of the present invention). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present invention also relates to the pharmaceutically active metabolites of the compounds of the invention, and uses of such metabolites in the methods of the invention. A "pharmaceutically active metabolite" means a pharmacologically active, product of metabolism in the body of a compound of the present invention or salt thereof. Prodrugs and active metabolites of a compound may be determined using routine techniques known or available in the art.

Preferably, the compound is selected from Table 1 and 2:

TABLE 1

Example list I (Formula A)

| Compound number | Name/Properties | Structure |
|---|---|---|
| 18 | 4,5,6,7-tetrabromo-2-(pyrrolidin-1-yl)-1H-benzo[d]imidazole; $C_{11}H_9Br_4N_3$ (MW 502.82) General procedure A; m/z 503.7 [M + H]$^+$; RT = 7.5 min | 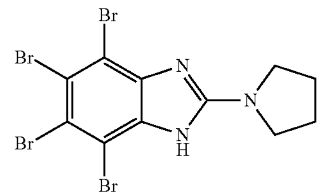 [SMILES: Brc1c(Br)c(Br)c2[nH]c(N3CCCC3)nc2c1Br] |
| 19 | 4,5,6,7-tetrabromo-2-morpholino-1H-benzo[d]imidazole; $C_{11}H_9Br_4N_3O$ (MW 518.82) General procedure A; m/z 519.7 [M + H]$^+$; RT = 12.5 min | 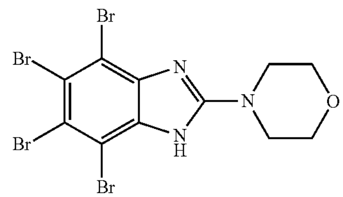 [SMILES: Brc1c(Br)c(Br)c2[nH]c(N3CCOCC3)nc2c1Br] |
| 20 | 4,5,6,7-tetrabromo-2-(piperazin-1-yl)-1H-benzo[d]imidazole; $C_{11}H_{10}Br_4N_4$ (MW 517.84) General procedure A; m/z 518.6 [M + H]$^+$; RT = 5.4 min | 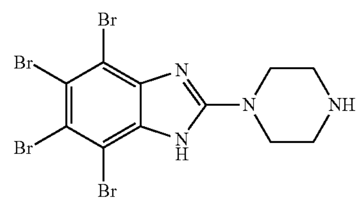 [SMILES: Brc1c(Br)c(Br)c2[nH]c(N3CCNCC3)nc2c1Br] |
| 21 | 4,5,6,7-tetrabromo-2-(4-methylpiperazin-1-yl)-1H-benzo[d]imidazole; $C_{12}H_{12}Br_4N_4$ (MW 531.87) General procedure A; m/z 532.7 [M + H]$^+$; RT = 5.5 min | 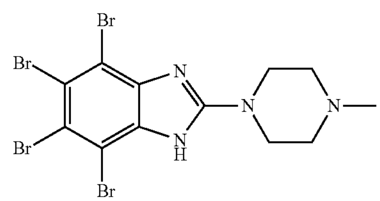 [SMILES: CN1CCN(c2nc3c(Br)c(Br)c(Br)c(Br)c3[nH]2)CC1] |
| 75 | 3-(4-(4,5,6,7-tetrabromo-1H-benzo[d]imidazol-2-yl)piperazin-1-yl)-N,N-dimethylpropan-1-amine; $C_{16}H_{21}Br_4N_5$ (MW 602.99) General procedure A; m/z 603.3 [M + H]$^+$; RT = 3.1 min | 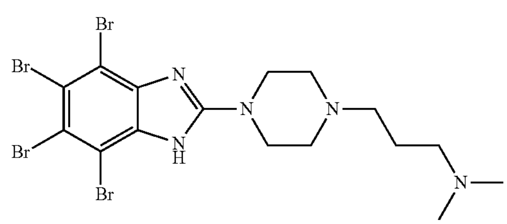 [SMILES: CN(C)CCCN1CCN(c2nc3c(Br)c(Br)c(Br)c(Br)c3[nH]2)CC1] |
| 76 | 4,5,6,7-tetrabromo-2-(4-(2-(piperidin-1-yl)ethyl)piperazin-1-yl)-1H-benzo[d]imidazole; $C_{18}H_{23}Br_4N_5$ (MW 629.02) General procedure A; m/z 629.8 [M + H]$^+$; | 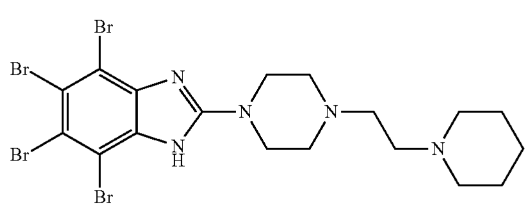 [SMILES: Brc1c(Br)c(Br)c2[nH]c(N3CCN(CCN4CCCCC4)CC3)nc2c1Br] |

TABLE 1-continued

Example list I (Formula A)

| Compound number | Name/Properties | Structure |
|---|---|---|
| 103 | 3-(4-(4,5,6,7-tetrabromo-1H-benzo[d]imidazol-2-yl)piperazin-1-yl)-N,N,N-trimethylpropan-1-ammonium bromide; $C_{17}H_{24}Br_5N_5$ (MW 697.93) General procedure B; m/z 617.9 [M − H]$^-$; RT = 2.3 min | 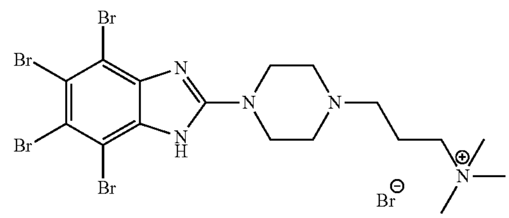 [SMILES: C[N+](C)(C)CCCN1CCN(c2nc3c(Br)c(Br)c(Br)c(Br)c3[nH]2)CC1 ; [Br-]] |
| 242 | 4,5,6,7-tetrabromo-2-(indolin-1-yl)-1H-benzo[d]imidazole; $C_{15}H_9Br_4N_3$ (MW 550.87) General procedure A; m/z 551.7 [M + H]$^+$; RT = 23.4 min | 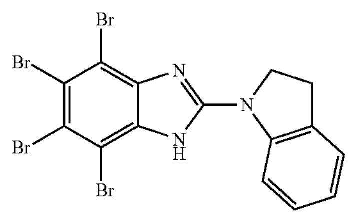 [SMILES: Brc1c(Br)c(Br)c2[nH]c(N3CCc4ccccc43)nc2c1Br] |
| 256 | 4,5,6,7-tetrabromo-2-(4-methyl-1,4-diazepan-1-yl)-1H-benzo[d]imidazole; $C_{13}H_{14}Br_4N_4$ (545.89) General procedure A; m/z 546.7 [M + H]$^+$; RT = 5.6 min | 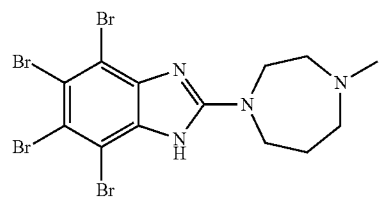 [SMILES: CN1CCCN(c2nc3c(Br)c(Br)c(Br)c(Br)c3[nH]2)CC1] |
| 260 | 4,5,6,7-tetrabromo-2-(1,4-diazepan-1-yl)-1H-benzo[d]imidazole; $C_{12}H_{12}Br_4N_4$ (531.87) General procedure A; m/z 532.7 [M + H]$^+$; RT = 5.6 min | 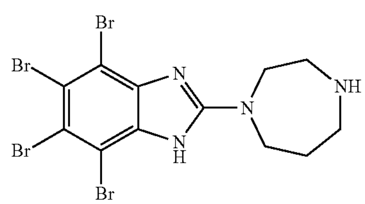 [SMILES: Brc1c(Br)c(Br)c2[nH]c(N3CCCNCC3)nc2c1Br] |
| 262 | 4,5,6,7-tetrabromo-2-(3-((2-methyl-1H-imidazol-1-yl)methyl)piperidin-1-yl)-1H-benzo[d]imidazole; $C_{17}H_{17}Br_4N_5$ (610.97) General procedure A; m/z 611.8 [M + H]$^+$; RT = 6.7 min | 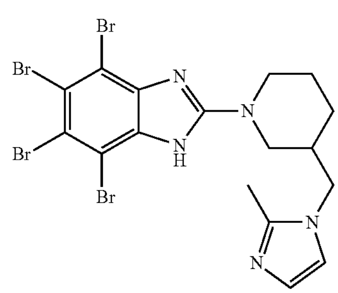 [SMILES: Cc1nccn1CC1CCCN(c2nc3c(Br)c(Br)c(Br)c(Br)c3[nH]2)C1] |
| 266 | 4,5,6,7-tetrabromo-2-(3-((4-(pyridin-2-yl)piperazin-1-yl)methyl)piperidin-1-yl)-1H-benzo[d]imidazole $C_{22}H_{24}Br_4N_6$ (692.07) General procedure A; m/z 692.9 [M + H]$^+$; RT = 6.6 min | 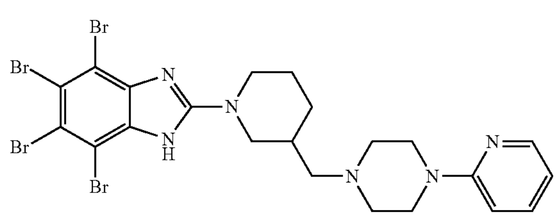 [SMILES: Brc1c(Br)c(Br)c2[nH]c(N3CCCC(CN4CCN(c5ccccn5)CC4)C3)nc2c1Br] |

TABLE 1-continued

Example list I (Formula A)

| Compound number | Name/Properties | Structure |
|---|---|---|
| 301 | 4,5,6,7-tetrabromo-2-(4-(1-[1-(1,1-dioxidotetrahydro-3-thienyl)-3,5-dimethyl-1H-pyrazol-4-yl]piperazin-1-yl-1H-benzo[d]imidazole; $C_{20}H_{22}Br_4N_6O_2S$ (730.11) General procedure A; m/z 730.8 [M + H]$^+$; RT = 17.6 min | 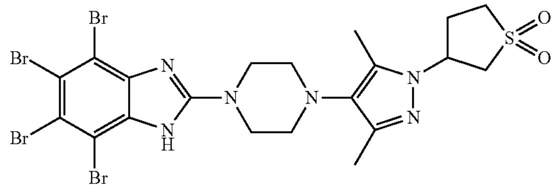 [SMILES: Cc1nn(C2CCS(=O)(=O)C2)c(C)c1N1CCN(c2nc3c(Br)c(Br)c(Br)c(Br)c3[nH]2)CC1] |
| 305 | 1-(4,5,6,7-tetrabromo-1H-benzo[d]imidazol-2-yl)-N-(5-methylthiazol-2-yl)piperidine-4-carboxamide; $C_{17}H_{15}Br_4N_5OS$ (657.02) General procedure A; m/z 657.8 [M + H]$^+$; RT = 16.3 min | 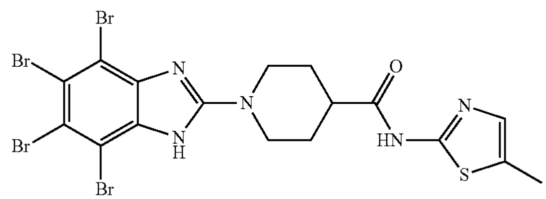 [SMILES: Cc1cnc(NC(=O)C2CCN(c3nc4c(Br)c(Br)c(Br)c(Br)c4[nH]3)CC2)s1] |
| 343 | 2-(4-(4,5,6,7-tetrabromo-1H-benzo[d]imidazol-2-yl)piperazin-1-yl)-N,N-dimethylethanamine; $C_{15}H_{19}Br_4N_5$ (588.96) General procedure A; m/z 589.9 [M + H]$^+$; RT = 5.4 min | 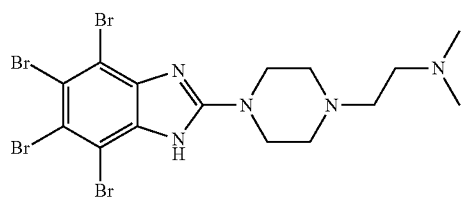 [SMILES: CN(C)CCN1CCN(c2nc3c(Br)c(Br)c(Br)c(Br)c3[nH]2)CC1] |
| 350 | 2-(4,5,6,7-tetrabromo-1H-benzo[d]imidazol-2-yl)-2,5-diaza-bicyclo[3.2.2]nonane; $C_{14}H_{14}Br_4N_4$ (557.9) General procedure A; m/z 558.9 [M + H]$^+$; RT = 6.0 min | 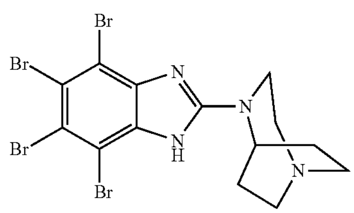 [SMILES: Brc1c(Br)c(Br)c2[nH]c(N3CCN4CCC3CC4)nc2c1Br] |
| 353 | 4,5,6,7-tetrabromo-2-((3aR,7aS)-octahydroindol-1-yl)-1H-benzo[d]imidazole; $C_{14}H_{12}Br_4N_4$ (555.89) General procedure A; m/z 577.8 [M + 23]$^+$; RT = 12.7 min | 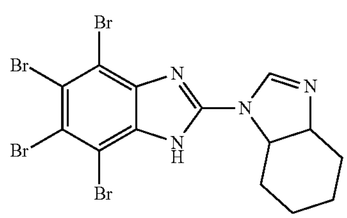 [SMILES: Brc1c(Br)c(Br)c2[nH]c(N3C=NC4CCCCC43)nc2c1Br] |
| 359 | 4,5,6,7-tetrabromo-1-isopropyl-2-(piperazin-1-yl)-1H-benzo[d]imidazole; $C_{14}H_{16}Br_4N_4$ (559.92) General procedure A; m/z 560.7 [M + H]$^+$; RT = 7.5 min | 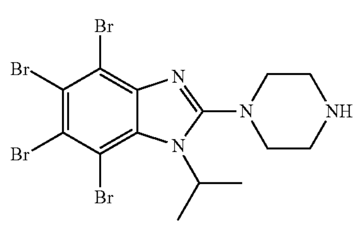 [SMILES: CC(C)n1c(N2CCNCC2)nc2c(Br)c(Br)c(Br)c(Br)c21] |
| 364 | 4,5,6,7-tetrabromo-2-((2S,5R)-2,5-dimethylpiperazin-1-yl)-1H-benzo[d]imidazole; $C_{13}H_{14}Br_4N_4$ (545.89) General procedure A; m/z 546.7 [M + H]$^+$; RT = 6.3 min | 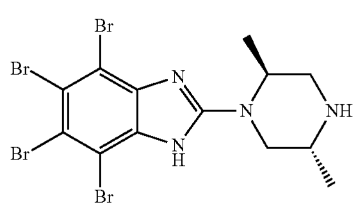 [SMILES: C[C@@H]1CN(c2nc3c(Br)c(Br)c(Br)c(Br)c3[nH]2)[C@@H](C)CN1] |

TABLE 1-continued

Example list I (Formula A)

| Compound number | Name/Properties | Structure |
|---|---|---|
| 367 | 1-(4,5,6,7-tetrabromo-1H-benzo[d]imidazol-2-yl)-1,2',3,4-tetrahydroquinoxaline; $C_{15}H_{10}Br_4N_4$ (565.88) General procedure A; m/z 566.6 [M + H]$^+$; RT = 19.5 min | 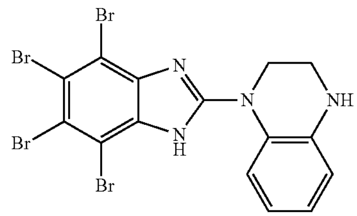 [SMILES: Brc1c(Br)c(Br)c2[nH]c(N3CCNc4ccccc43)nc2c1Br] |
| 374 | 1-benzyl-4,5,6,7-tetrabromo-2-(piperazin-1-yl)-1H-benzo[d]imidazole; $C_{18}H_{16}Br_4N_4$ (607.96) General procedure A; m/z 608.6 [M + H]$^+$; RT = 8.2 min | 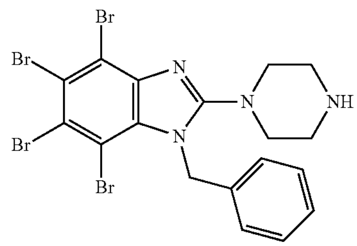 [SMILES: Brc1c(Br)c(Br)c2c(nc(N3CCNCC3)n2Cc2ccccc2)c1Br] |
| 376 | ethyl 4-(4,5,6,7-tetrabromo-1H-benzo[d]imidazol-2-yl)piperazine-1-carboxylate; $C_{15}H_{16}Br_4N_4O_2$ (603.93) General procedure C; m/z 604.7[M + H]$^+$; RT = 9.2 min | 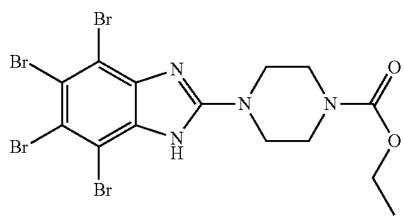 [SMILES: CCOC(=O)N1CCN(c2nc3c(Br)c(Br)c(Br)c(Br)c3[nH]2)CC1] |
| 377 | ethyl 2-(4-(ethoxycarbonyl)piperazin-1-yl)-4,5,6,7-tetrabromo-1H-benzo[d]imidazole-1-carboxylate; $C_{19}H_{22}Br_4N_4O_4$ (690.02) General procedure C; m/z 690.8 [M + H]$^+$; RT = 11.6 min | 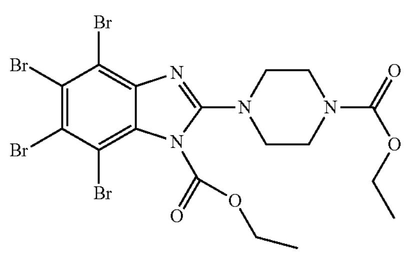 [SMILES: CCOC(=O)N1CCN(c2nc3c(Br)c(Br)c(Br)c(Br)c3n2C(=O)OCC)CC1] |
| 378 | 1-(4,5,6,7-tetrabromo-1H-benzo[d]imidazol-2-yl)-N,N-dimethylpiperidin-3-amine; $C_{14}H_{16}Br_4N_4$ (559.92) General procedure A; m/z 560.8 [M + H]$^+$; RT = 6.1 min | 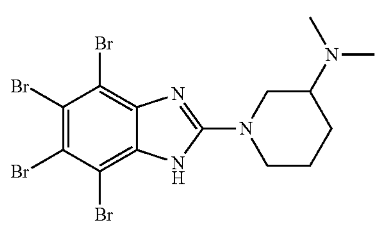 [SMILES: CN(C)C1CCCN(c2nc3c(Br)c(Br)c(Br)c(Br)c3[nH]2)C1] |
| 383 | 3-(4-(4,5,6,7-tetrabromo-1H-benzo[d]imidazol-2-yl)piperazin-1-yl)propan-1-ol; $C_{14}H_{16}Br_4N_4O_4$ (575.92) General procedure A; m/z 576.7 [M + H]$^+$; RT = 5.5 min | 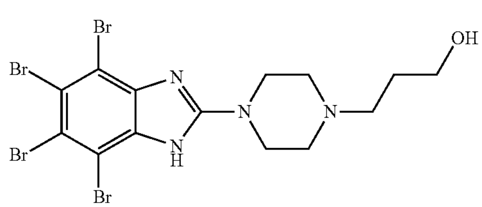 [SMILES: OCCCN1CCN(c2nc3c(Br)c(Br)c(Br)c(Br)c3[nH]2)CC1] |

TABLE 1-continued

Example list I (Formula A)

| Compound number | Name/Properties | Structure |
|---|---|---|
| 384 | 2-(4-(4,5,6,7-tetrabromo-1H-benzo[d]imidazol-2-yl)piperazin-1-yl)-3-methylbutanenitrile; $C_{16}H_{17}Br_4N_5$ (MW 598.96) General procedure A; m/z 599.8 [M + H]$^+$; RT = 20.2 min | 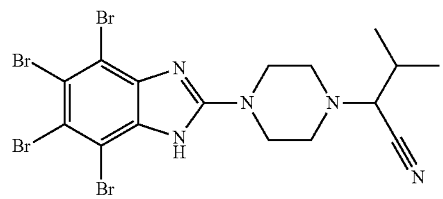 [SMILES: CC(C)C(C#N)N1CCN(c2nc3c(Br)c(Br)c(Br)c(Br)c3[nH]2)CC1] |
| 385 | 4,5,6,7-tetrabromo-2-(4-(4-methylpiperazin-1-yl)piperidin-1-yl)-1H-benzo[d]imidazole; $C_{17}H_{21}Br_4N_5$ (MW 615.0) General procedure A; m/z 615.7 [M + H]$^+$; RT = 5.3 min | 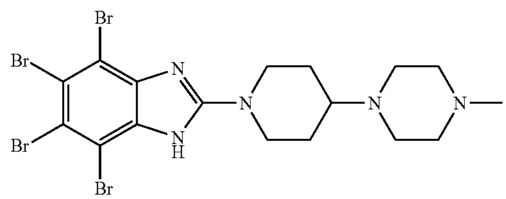 [SMILES: CN1CCN(C2CCN(c3nc4c(Br)c(Br)c(Br)c(Br)c4[nH]3)CC2)CC1] |
| 386 | 4,5,6,7-tetrabromo-2-(4-(piperidin-4-yl)piperidin-1-yl)-1H-benzo[d]imidazole; $C_{17}H_{20}Br_4N_4$ (599.98) General procedure A; m/z 600.8 [M + H]$^+$; RT = 6.9 min | 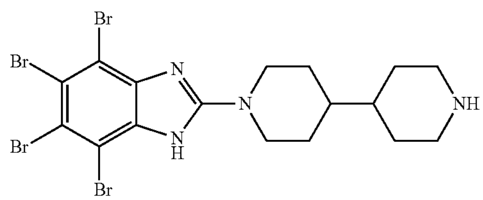 [SMILES: Brc1c(Br)c(Br)c2[nH]c(N3CCC(C4CCNCC4)CC3)nc2c1Br] |
| 387 | 2-(4-((H-imidazo[1,2-a]pyridin-2-yl)methyl)piperazin-1-yl)-4,5,6,7-tetrabromo-1H-benzo[d]imidazole; $C_{19}H_{16}Br_4N_6$ (647.99) General procedure A; m/z 650.8 [M + H]$^+$; RT = 6.2 min | 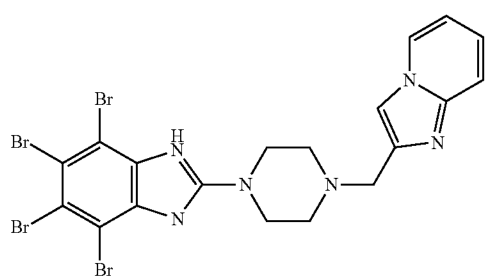 |
| 389 | 4,5,6,7-tetrabromo-2-(4-((2-(4-fluorophenyl)thiazol-4-yl)methyl)piperazin-1-yl)-1H-benzo[d]imidazole; $C_{21}H_{16}Br_4FN_5S$ (709.06) General procedure A; m/z 709.7 [M + H]$^+$; RT = 9.8 min | 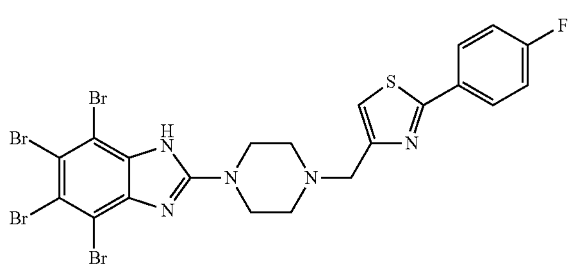 [SMILES: Fc1ccc(-c2nc(CN3CCN(c4nc5c(Br)c(Br)c(Br)c(Br)c5[nH]4)CC3)cs2)cc1] |
| 390 | 4,5,6,7-tetrabromo-2-(4-((3-p-tolyl-1,2,4-oxadiazol-5-yl)methyl)piperazin-1-yl)-1H-benzo[d]imidazole; $C_{21}H_{18}Br_4N_6O$ (690.02) General procedure; m/z 690.7 [M + H]$^+$; RT = 21.3 min | 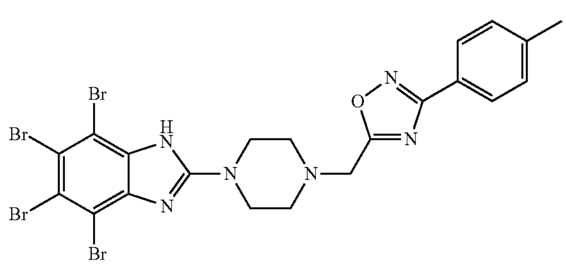 [SMILES: Cc1ccc(-c2noc(CN3CCN(c4nc5c(Br)c(Br)c(Br)c(Br)c5[nH]4)CC3)n2)cc1] |

TABLE 1-continued

Example list I (Formula A)

| Compound number | Name/Properties | Structure |
|---|---|---|
| 392 | 4-(4,5,6,7-tetrabromo-1H-benzo[d]imidazol-2-yl)piperazine-1-carboxamidine; $C_{12}H_{12}Br_4N_6$ (559.88) General procedure B; m/z 560.8 $[M + H]^+$; RT = 5.9 min | 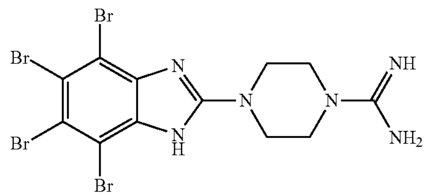 [SMILES: N=C(N)N1CCN(c2nc3c(Br)c(Br)c(Br)c(Br)c3[nH]2)CC1] |
| 393 | 2-(4-(4,5,6,7-tetrabromo-1H-benzo[d]imidazol-2-yl)piperazin-1-yl)acetic acid; $C_{13}H_{12}Br_4N_4O_2$ (575.88) General procedure C; m/z 576.8 $[M + H]^+$; RT = 8.0 min | 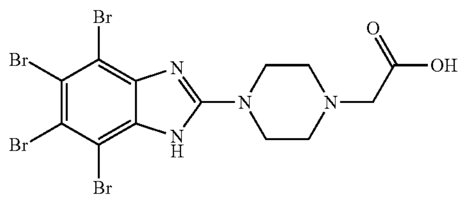 [SMILES: O=C(O)CN1CCN(c2nc3c(Br)c(Br)c(Br)c(Br)c3[nH]2)CC1] |
| 394 | 2-(4-(3-methoxybenzyl)piperazin-1-yl)-4,5,6,7-tetrabromo-1H-benzo[d]imidazole; $C_{19}H_{18}Br_4N_4O$ (637.99) General procedure A; m/z 638.8 $[M + H]^+$; RT = 8.2 min | 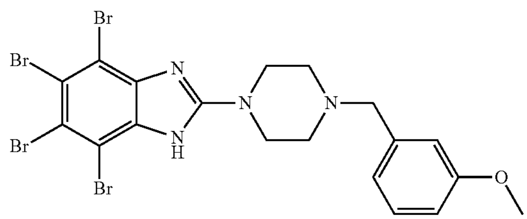 [SMILES: COc1cccc(CN2CCN(c3nc4c(Br)c(Br)c(Br)c(Br)c4[nH]3)CC2)c1] |
| 414 | 4,5,6,7-tetrabromo-2-(4-((2-methyl-1H-imidazo[1,2-a]pyridin-3-yl)methyl)piperazin-1-yl)-1H-benzo[d]imidazole; $C_{20}H_{18}Br_4N_6$ (662.01) General procedure A; m/z 662.7 $[M + H]^+$; RT = 6.7 min | 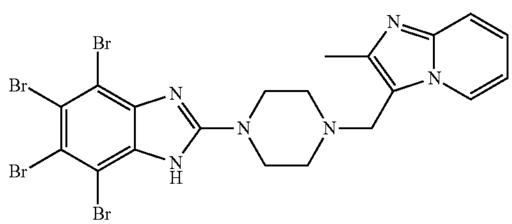 [SMILES: Cc1nc2ccccn2c1CN1CCN(c2nc3c(Br)c(Br)c(Br)c(Br)c3[nH]2)CC1] |
| 415 | 4,5,6,7-tetrabromo-1-methyl-2-(piperazin-1-yl)-1H-benzo[d] imidazole; $C_{12}H_{12}Br_4N_4$ (531.87) General procedure A; m/z 532.80 $[M + H]^+$; RT = 5.9 min | 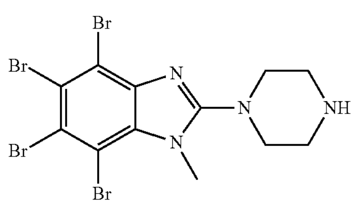 [SMILES: Cn1c(N2CCNCC2)nc2c(Br)c(Br)c(Br)c(Br)c21] |
| 416 | 4,5,6,7-tetrabromo-1-ethyl-2-(piperazin-1-yl)-1H-benzo[d]imidazole; $C_{13}H_{14}Br_4N_4$ (545.89) General procedure A; m/z 546.7 $[M + H]^+$; RT = 6.8 min | 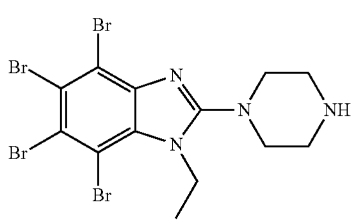 [SMILES: CCn1c(N2CCNCC2)nc2c(Br)c(Br)c(Br)c(Br)c21] |
| 417 | 4,5,6,7-tetrabromo-2-(piperazin-1-yl)-1-propyl-1H-benzo[d]imidazole; $C_{14}H_{16}Br_4N_4$ (559.92) General procedure A; m/z 560.8 $[M + H]^+$; RT = 7.7 min | 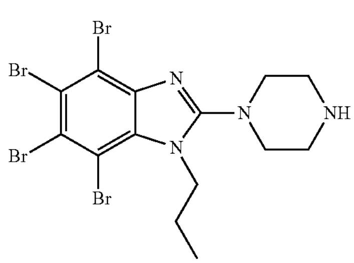 [SMILES: CCCn1c(N2CCNCC2)nc2c(Br)c(Br)c(Br)c(Br)c21] |

TABLE 1-continued

Example list I (Formula A)

| Compound number | Name/Properties | Structure |
|---|---|---|
| 421 | [4-[4,5,6,7-tetrabromo-1-(carboxymethyl)-1H-benzo[d]imidazol-2-yl]piperazin-1-yl]acetic acid<br>$C_{15}H_{14}Br_4N_4O_4$ (633.91).<br>General procedure C; m/z 634.8 [M + H]$^+$; RT = 8.1 min | 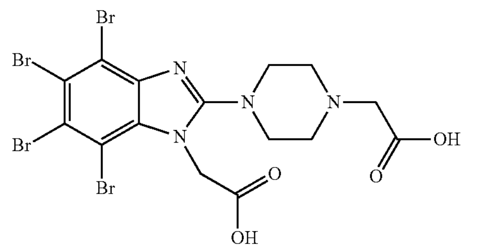 [SMILES: O=C(O)CN1CCN(c2nc3c(Br)c(Br)c(Br)c(Br)c3n2CC(=O)O)CC1] |
| 436 | 4,5,6,7-tetrabromo-2-(4-(2-(piperazin-1-yl)ethyl)piperazin-1-yl)-1H-benzo[d]imidazole;<br>$C_{17}H_{22}Br_4N_6$ (630.01)<br>General procedure A; m/z 630.9 [M + H]$^+$; RT = 3.6 min | 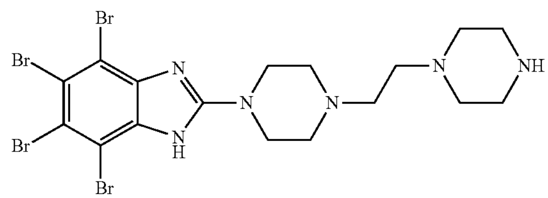 [SMILES: Brc1c(Br)c(Br)c2[nH]c(N3CCN(CCN4CCNCC4)CC3)nc2c1Br] |
| 441 | 4,5,6,7-tetrabromo-1-ethyl-2-(4-(2-(piperazin-1-yl)ethyl)piperazin-1-yl)-1H-benzo[d]imidazole;<br>$C_{19}H_{26}Br_4N_6$ (658.07)<br>General procedure A; m/z 658.9 [M + H]$^+$; RT = 4.4 min | 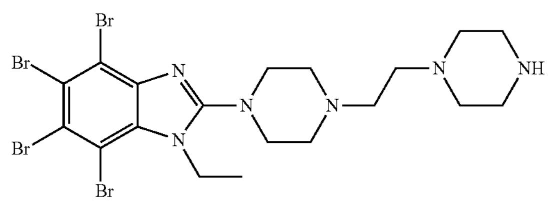 [SMILES: CCn1c(N2CCN(CCN3CCNCC3)CC2)nc2c(Br)c(Br)c(Br)c(Br)c21] |
| 450 | 4,5,6,7-tetrabromo-1-ethyl-2-(4-(3-morpholinopropyl)piper-azin-1-yl])-1H-benzo[d]imidazole;<br>$C_{20}H_{27}Br_4N_5O$ (673.08)<br>General procedure A; m/z 673.9 [M + H]$^+$; RT = 4.0 min | 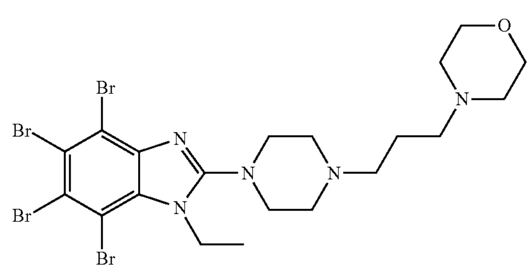 [SMILES: CCn1c(N2CCN(CCCN3CCOCC3)CC2)nc2c(Br)c(Br)c(Br)c(Br)c21] |
| 451 | 4,5,6,7-tetrabromo-2-(4-(3-(piperazin-1-yl)propyl)piperazin-1-yl)-1H-benzo[d]imidazole;<br>$C_{18}H_{24}Br_4N_6$ (644.04)<br>General procedure A; m/z 644.9 [M + H]$^+$; RT = 2.9 min | 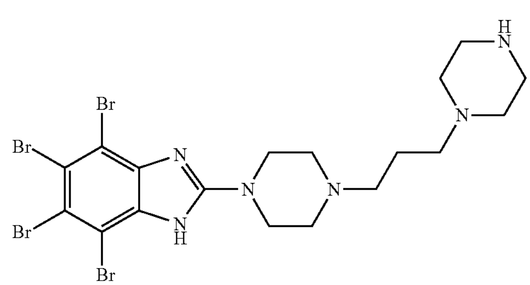 [SMILES: Brc1c(Br)c(Br)c2[nH]c(N3CCN(CCCN4CCNCC4)CC3)nc2c1Br] |

TABLE 2

Example list II (Formula B)

| Compound number | Name | Structure |
|---|---|---|
| 11 | N-(3-aminopropyl)-4,5,6,7-tetrabromo-1H-benzo[d]imidazol-2-amine; $C_{10}H_{10}Br_4N_4$ (MW 505.83) General procedure A; m/z 506.4 [M + H]$^+$; RT = 4.6 min | 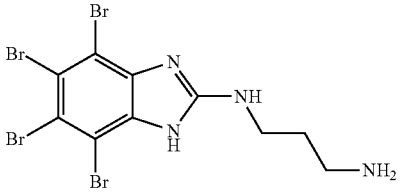 [SMILES: NCCCNc1nc2c(Br)c(Br)c(Br)c(Br)c2[nH]1] |
| 13 | 4,5,6,7-tetrabromo-N-(2-(piperidin-1-yl)ethyl)-1H-benzo[d]imidazol-2-amine; $C_{14}H_{16}Br_4N_4$ (MW 559.92) General procedure A; m/z 560.7 [M + H]$^+$; RT = 4.7 min | 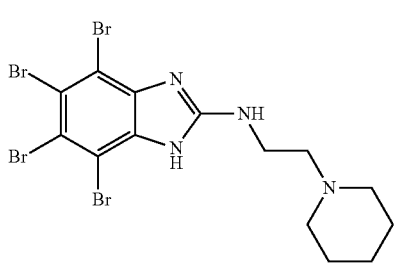 [SMILES: Brc1c(Br)c(Br)c2[nH]c(NCCN3CCCCC3)nc2c1Br] |
| 14 | 4,5,6,7-tetrabromo-N-(2-(pyrrolidin-1-yl)ethyl)-1H-benzo[d]imidazol-2-amine; $C_{13}H_{14}Br_4N_4$ (MW 545.89) General procedure A; m/z 546.8 [M + H]$^+$; RT = 3.8 min | 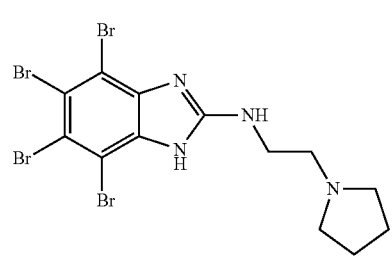 [SMILES: Brc1c(Br)c(Br)c2[nH]c(NCCN3CCCC3)nc2c1Br] |
| 16 | 4,5,6,7-tetrabromo-N-(2-morpholinoethyl)-1H-benzo[d]imidazol-2-amine; $C_{13}H_{14}Br_4N_4O$ (MW 561.89) General procedure A; m/z 562.8 [M + H]$^+$; RT = 3.6 min | 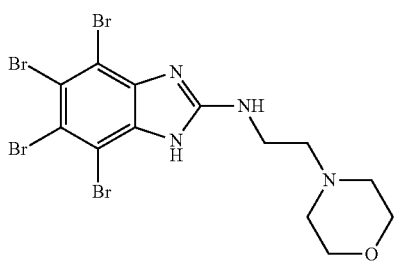 [SMILES: Brc1c(Br)c(Br)c2[nH]c(NCCN3CCOCC3)nc2c1Br] |
| 28 | 4,5,6,7-tetrabromo-N-(pyridin-4-yl)-1H-benzo[d]imidazol-2-amine; $C_{12}H_6Br_4N_4$ (MW 525.82) General procedure A; m/z 526.8 [M + H]$^+$; RT = 4.4 min | 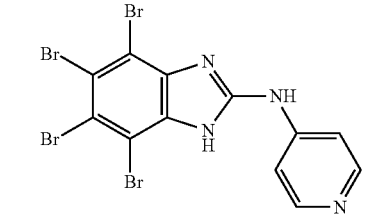 [SMILES: Brc1c(Br)c(Br)c2[nH]c(Nc3ccncc3)nc2c1Br] |
| 57 | 1-(3-(4,5,6,7-tetrabromo-1H-benzo[d]imidazol-2-ylamino)propyl)pyrrolidine-2,5-dione; $C_{14}H_{12}Br_4N_4O_2$ (MW 587.89) General procedure A; m/z 588.6 [M + H]$^+$; RT = 12.3 min | 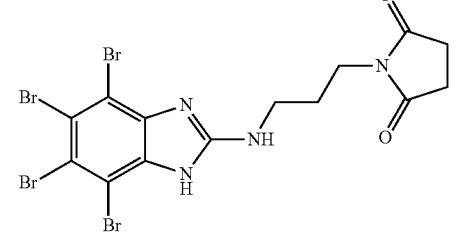 |

TABLE 2-continued

Example list II (Formula B)

| Compound number | Name | Structure |
|---|---|---|
| 58 | 4,5,6,7-tetrabromo-N-(3-(pyrrolidin-1-yl)propyl-1H-benzo[d]imidazol-2-amine; $C_{14}H_{16}Br_4N_4$ (MW 559.92) General procedure A; m/z 560.7 [M + H]$^+$; 6.2 min | 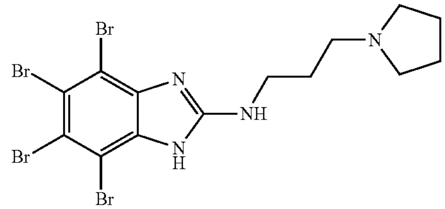 [SMILES: Brc1c(Br)c(Br)c2[nH]c(NCCCN3CCCC3)nc2c1Br] |
| 59 | 4,5,6,7-tetrabromo-N-(3-(piperidin-1-yl)propyl)-1H-benzo[d]imidazol-2-amine; $C_{15}H_{18}Br_4N_4$ (MW 573.95) General procedure A; m/z 574.7 [M + H]$^+$; RT = 3.6 min | 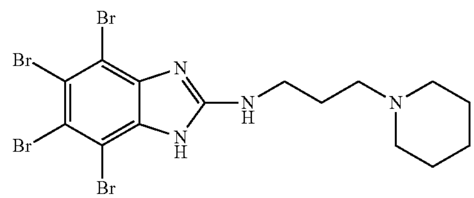 [SMILES: Brc1c(Br)c(Br)c2[nH]c(NCCCN3CCCCC3)nc2c1Br] |
| 61 | N-(4-aminobutyl)-4,5,6,7-tetrabromo-1H-benzo[d]imidazol-2-amine; $C_{11}H_{12}Br_4N_4$ (MW 519.86) General procedure A; m/z 520.8 [M + H]$^+$; RT = 2.9 min | 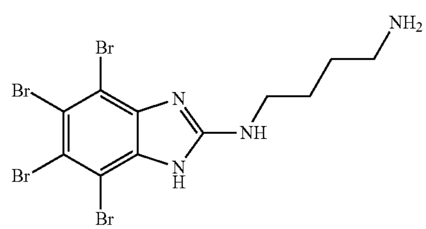 [SMILES: NCCCCNc1nc2c(Br)c(Br)c(Br)c(Br)c2[nH]1] |
| 65 | N-(3-(1H-imidazol-1-yl)propyl)-4,5,6,7-tetrabromo-1H-benzo[d]imidazol-2-amine; $C_{13}H_{11}Br_4N_5$ (MW 556.88) General procedure A; m/z 557.7 [M + H]$^+$; RT = 3.2 min | 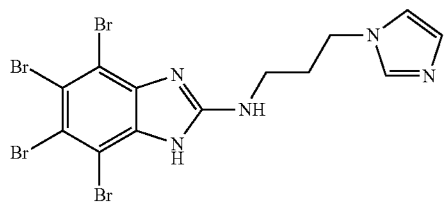 [SMILES: Brc1c(Br)c(Br)c2[nH]c(NCCCn3ccnc3)nc2c1Br] |
| 67 | 4,5,6,7-tetrabromo-N-((piperidin-4-yl)methyl)-1H-benzo[d]imidazol-2-amine; $C_{13}H_{14}Br_4N_4$ (MW 545.89) General procedure A; m/z 546.8 [M + H]$^+$; 3.3 min | 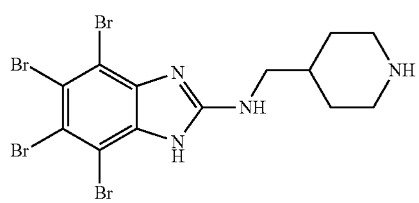 [SMILES: Brc1c(Br)c(Br)c2[nH]c(NCC3CCNCC3)nc2c1Br] |
| 79 | 4,5,6,7-tetrabromo-N-phenyl-1H-benzo[d]imidazol-2-amine; $C_{13}H_7Br_4N_3$ (MW 524.83) General procedure A; m/z 525.7 [M + H]$^+$; 9.8 min | 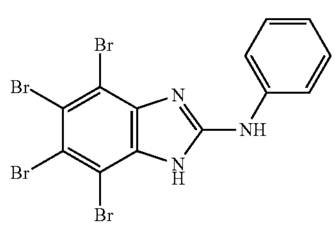 [SMILES: Brc1c(Br)c(Br)c2[nH]c(Nc3ccccc3)nc2c1Br] |
| 82 | N-benzyl-4,5,6,7-tetrabromo-1H-benzo[d]imidazol-2-amine; $C_{14}H_9Br_4N_3$ (MW 538.86) General procedure A; m/z 539.7 [M + H]$^+$; 18.9 min | 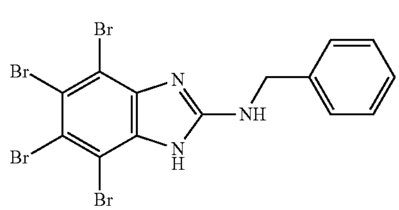 [SMILES: Brc1c(Br)c(Br)c2[nH]c(NCc3ccccc3)nc2c1Br] |

TABLE 2-continued

Example list II (Formula B)

| Compound number | Name | Structure |
|---|---|---|
| 85 | N-benzyl-4,5,6,7-tetrabromo-N-(3-(dimethylamino)propyl)-1H-benzo[d]imidazol-2-amine; $C_{19}H_{20}Br_4N_4$ (MW 624.0) General procedure A; m/z 624.7 $[M + H]^+$; 8.8 min | 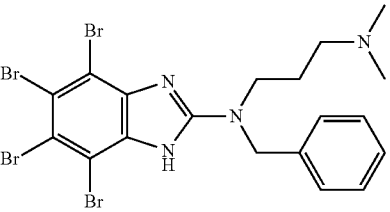 [SMILES: CN(C)CCCN(Cc1ccccc1)c1nc2c(Br)c(Br)c(Br)c(Br)c2[nH]1] |
| 86 | N1-(4,5,6,7-tetrabromo-1H-benzo[d]imidazol-2-yl)benzene-1,4-diamine; $C_{13}H_8Br_4N_4$ (MW 539.84) General procedure A; m/z 540.6 $[M + H]^+$; RT = 2.3 min | 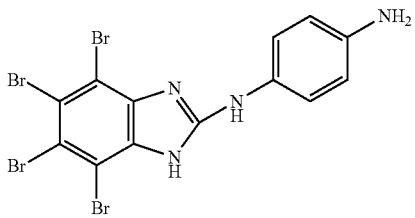 [SMILES: Nc1ccc(Nc2nc3c(Br)c(Br)c(Br)c(Br)c3[nH]2)cc1] |
| 87 | N1-(4,5,6,7-tetrabromo-1H-benzo[d]imidazol-2-yl)cyclohexane-1,4-diamine; $C_{13}H_{14}Br_4N_4$ (MW 545.89) General procedure A; m/z 546.8 $[M + H]^+$; RT = 1.6 min | 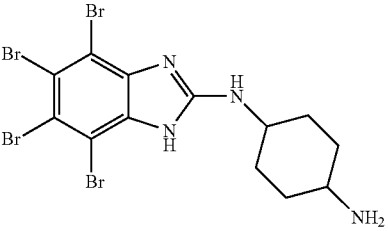 [SMILES: NC1CCC(Nc2nc3c(Br)c(Br)c(Br)c(Br)c3[nH]2)CC1] |
| 90 | 1-(4,5,6,7-tetrabromo-1H-benzo[d]imidazol-2-ylamino)-3-aminopropan-2-ol; $C_{10}H_{10}Br_4N_4O$ (MW 521.83) General procedure A; m/z 522.6 $[M + H]^+$; RT = 2.9 min | 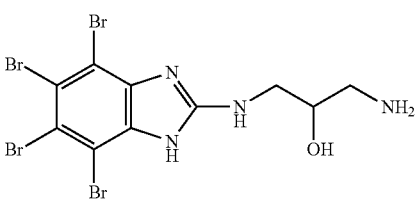 [SMILES: NCC(O)CNc1nc2c(Br)c(Br)c(Br)c(Br)c2[nH]1] |
| 95 | N,1-dibenzyl-4,5,6,7-tetrabromo-N-(2-(dimethylamino)ethyl)-1H-benzo[d]imidazol-2-amine; $C_{25}H_{24}Br_4N_4$ (MW 700.1) General procedure A; m/z 700.9 $[M + H]^+$; RT = 4.1 min | 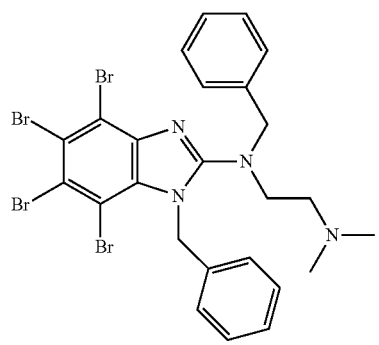 [SMILES: CN(C)CCN(Cc1ccccc1)c1nc2c(Br)c(Br)c(Br)c(Br)c2n1Cc1ccccc1] |

TABLE 2-continued

Example list II (Formula B)

| Compound number | Name | Structure |
|---|---|---|
| 96 | N-(2-(N-benzyl-N,N-dimethylammonium)ethyl)-N,1-dibenzyl-4,5,6,7-tetrabromo-1H-benzo[d]imidazol-2-amine bromide; $C_{32}H_{31}Br_4N_4$ (MW 791.23) General procedure A; m/z 790.9 [M]$^+$; RT = 9.6 min | 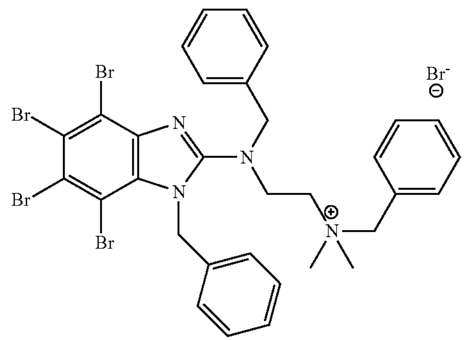 |
| 104 | (3-(4,5,6,7-tetrabromo-1H-benzo[d]imidazol-2-ylamino)propyl)guanidine; $C_{11}H_{12}Br_4N_6$ (MW 547.87) General procedure B; m/z 548.7 [M + H]$^+$; RT = 5.3min | 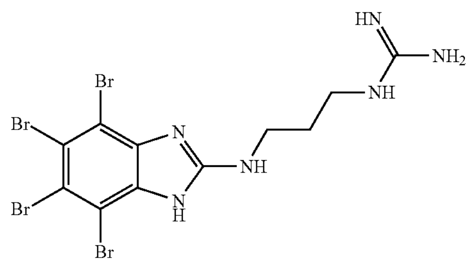 [SMILES: N=C(N)NCCCNc1nc2c(Br)c(Br)c(Br)c(Br)c2[nH]1] |
| 105 | N-(3-(1H-1,2,4-triazol-1-yl)propyl)-4,5,6,7-tetrabromo-1H-benzo[d]imidazol-2-amine; $C_{12}H_{10}Br_4N_6$ (MW 557.86) General procedure A; m/z 558.7 [M + H]$^+$; RT = 9.7 min | 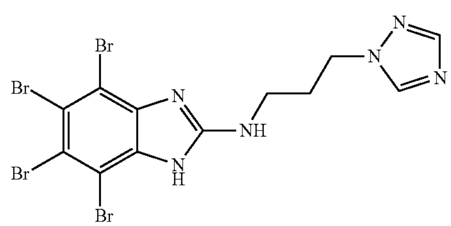 [SMILES: Brc1c(Br)c(Br)c2[nH]c(NCCCn3cncn3)nc2c1Br] |
| 114 | 4,5,6,7-tetrabromo-N-(2,3-dihydro-1H-inden-2-yl)-1H-benzo[d]imidazol-2-amine; $C_{16}H_{11}Br_4N_3$ (MW 564.9) General procedure A; m/z 565.8 [M + H]$^+$; RT = 19.8 min | 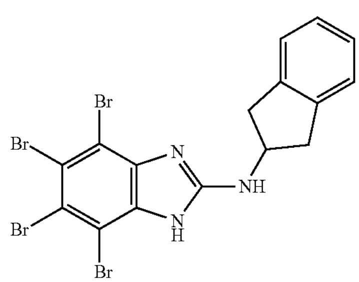 [SMILES: Brc1c(Br)c(Br)c2[nH]c(NC3Cc4ccccc4C3)nc2c1Br] |
| 117 | N-benzyl-4,5,6,7-tetrabromo-N-methyl-1H-benzo[d]imidazol-2-amine; $C_{15}H_{11}Br_4N_3$ (MW 552.88) General procedure A; m/z 553.8 [M + H]$^+$; RT = 20.5 min | 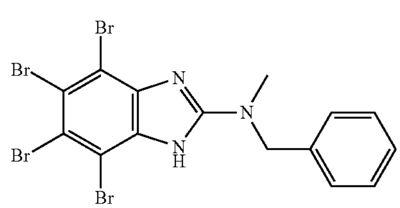 [SMILES: CN(Cc1ccccc1)c1nc2c(Br)c(Br)c(Br)c(Br)c2[nH]1] |

TABLE 2-continued

Example list II (Formula B)

| Compound number | Name | Structure |
|---|---|---|
| 128 | 4,5,6,7-tetrabromo-N-(2-(pyridin-2-yl)ethyl)-1H-benzo[d]imidazol-2-amine; $C_{14}H_{10}Br_4N_4$ (MW 553.87) General procedure A; m/z 554.6 [M + H]$^+$; RT = 6.5 min | 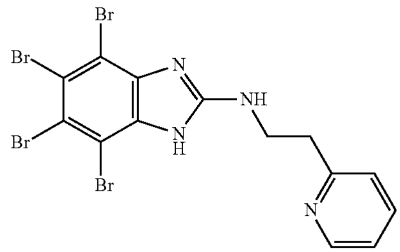 [SMILES: Brc1c(Br)c(Br)c2[nH]c(NCCc3ccccn3)nc2c1Br] |
| 158 | N-benzyl-4,5,6,7-tetrabromo-N-(2-(dimethylamino)ethyl)-1H-benzo[d]imidazol-2-amine; $C_{18}H_{18}Br_4N_4$ (MW 609.98) General procedure A; m/z 610.8 [M + H]$^+$; RT = 8.4 min | 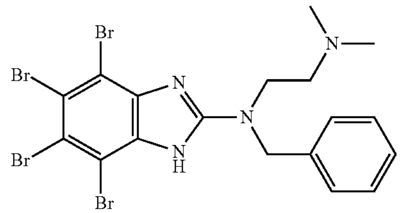 [SMILES: CN(C)CCN(Cc1ccccc1)c1nc2c(Br)c(Br)c(Br)c(Br)c2[nH]1] |
| 164 | N-(3-(4-(3-aminopropyl)piperazin-1-yl)propyl)-4,5,6,7-tetrabromo-1H-benzo[d]imidazol-2-amine; $C_{17}H_{24}Br_4N_6$ (MW 632.03) General procedure A; m/z 632.8 [M + H]$^+$; RT = 2.6 min | 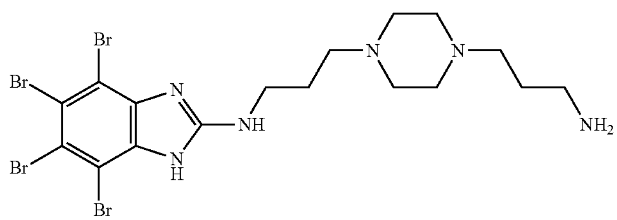 [SMILES: NCCCN1CCN(CCCNc2nc3c(Br)c(Br)c(Br)c(Br)c3[nH]2)CC1] |
| 165 | N-(2-(1H-imidazol-1-yl)benzyl)-4,5,6,7-tetrabromo-1H-benzo[d]imidazol-2-amine; $C_{17}H_{11}Br_4N_5$ (MW 604.92) General procedure A; m/z 605.7 [M + H]$^+$; RT = 7.1 min | 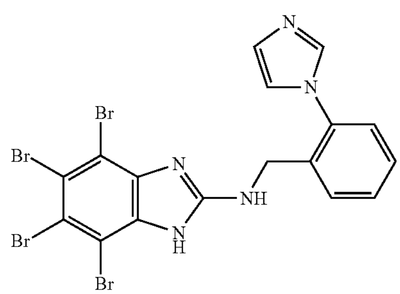 [SMILES: Brc1c(Br)c(Br)c2[nH]c(NCc3ccccc3-n3ccnc3)nc2c1Br] |
| 166 | 4,5,6,7-tetrabromo-N-((1-(2-(dimethylamino)ethyl)pyrrolidin-3-yl)methyl)-1H-benzo[d]imidazol-2-amine; $C_{16}H_{21}Br_4N_5$ (MW 602.99) General procedure A; m/z 603.8 [M + H]$^+$; RT = 3.3 min | 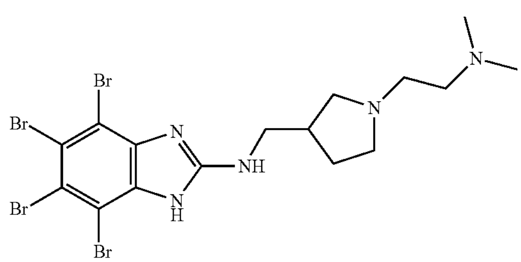 [SMILES: CN(C)CCN1CCC(CNc2nc3c(Br)c(Br)c(Br)c(Br)c3[nH]2)C1] |
| 192 | 4,5,6,7-tetrabromo-N-(3-morpholinopropyl)-1H-benzo[d]imidazol-2-amine; $C_{14}H_{16}Br_4N_4O$ (MW 575.92) General procedure A; m/z 576.7 [M + H]$^+$; RT = 5.2 min | 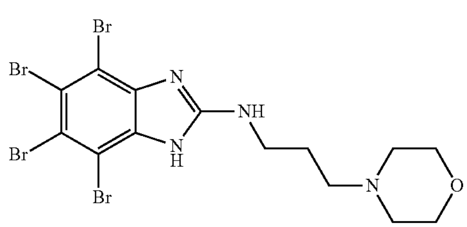 [SMILES: Brc1c(Br)c(Br)c2[nH]c(NCCCN3CCOCC3)nc2c1Br] |

TABLE 2-continued

Example list II (Formula B)

| Compound number | Name | Structure |
|---|---|---|
| 193 | 4,5,6,7-tetrabromo-N-(3-(4-methylpiperazin-1-yl)propyl)-1H-benzo[d]imidazol-2-amine; $C_{15}H_{19}Br_4N_5$ (MW 588.96) General procedure A; m/z 589.8 [M + H]$^+$; RT = 3.8 min | 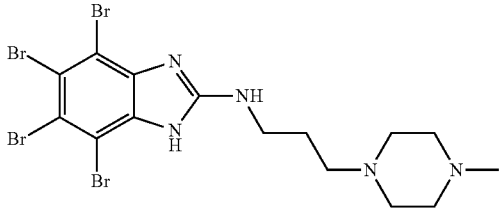 [SMILES: CN1CCN(CCCNc2nc3c(Br)c(Br)c(Br)c(Br)c3[nH]2)CC1] |
| 236 | 4,5,6,7-tetrabromo-N-(3-bromophenyl)-1H-benzo[d]imidazol-2-amine; $C_{13}H_6Br_5N_3$ (MW 603.73) General procedure A; m/z 605.6 [M + H]$^+$; RT = 22.7 min | 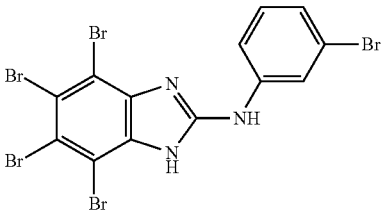 [SMILES: Brc1cccc(Nc2nc3c(Br)c(Br)c(Br)c(Br)c3[nH]2)c1] |
| 243 | 4-(2-(4,5,6,7-tetrabromo-1H-benzo[d]imidazol-2-ylamino)ethyl)phenol; $C_{15}H_{11}Br_4N_3O$ (MW 568.88) General procedure A; m/z 569.7 [M + H]$^+$; RT = 13.4 min | 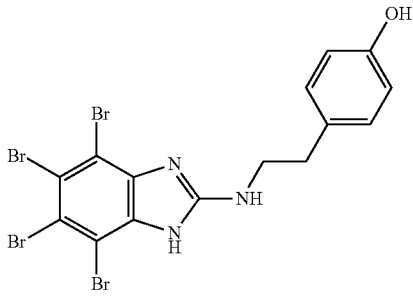 [SMILES: Oc1ccc(CCNc2nc3c(Br)c(Br)c(Br)c(Br)c3[nH]2)cc1] |
| 247 | 4,5,6,7-tetrabromo-N-(2-(4-(pyrimidin-2-yl)piperazin-1-yl)ethyl)-1H-benzo[d]imidazol-2-amine; $C_{17}H_{17}Br_4N_7$ (MW 638.98) General procedure A; m/z 639.8 [M + H]$^+$; RT = 7.4 min | 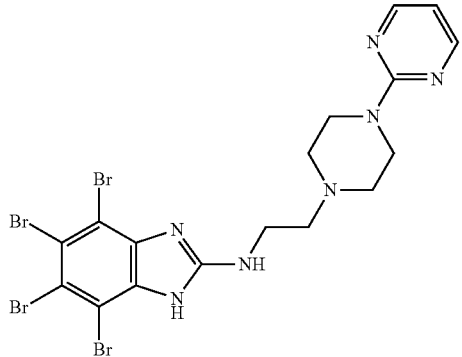 [SMILES: Brc1c(Br)c(Br)c2[nH]c(NCCN3CCN(c4ncccn4)CC3)nc2c1Br] |
| 248 | 4,5,6,7-tetrabromo-N-(2-methyl-3-(4-methyl-4H-1,2,4-triazol-3-yl)phenyl)-1H-benzo[d]imidazol-2-amine; $C_{17}H_{12}Br_4N_6$ (MW 619.93) General procedure A; m/z 620.8 [M + H]$^+$; RT = 13.5 min | 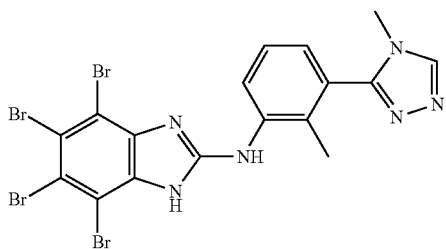 [SMILES: Cc1c(Nc2nc3c(Br)c(Br)c(Br)c(Br)c3[nH]2)cccc1-c1nncn1C] |

TABLE 2-continued

Example list II (Formula B)

| Compound number | Name | Structure |
|---|---|---|
| 249 | (5-(4,5,6,7-tetrabromo-1H-benzo[d]imidazol-2-ylamino)-2H-1,2,4-triazol-3-yl)(piperidin-1-yl)methanone; $C_{15}H_{13}Br_4N_7O$ (MW 626.93) General procedure A; m/z 627.8 [M + H]+; 16.2 min | 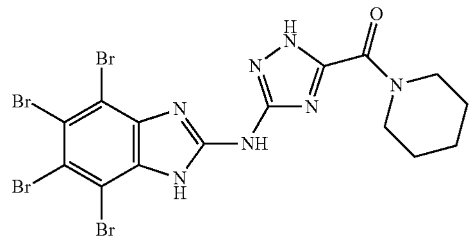 [SMILES: O=C(c1nc(Nc2nc3c(Br)c(Br)c(Br)c(Br)c3[nH]2)n[nH]1)N1CCCCC1] |
| 259 | 4,5,6,7-tetrabromo-N-(naphthalen-3-yl)-1H-benzo[d]imidazol-2-amine; $C_{17}H_9Br_4N_3$ (MW 574.89) General procedure A; m/z 575.8 [M + H]+; RT = 23.1 min | 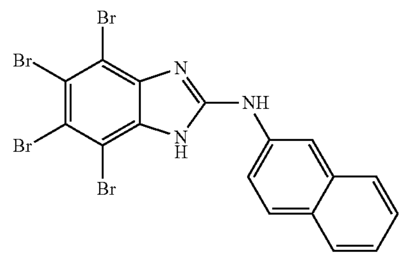 [SMILES: Brc1c(Br)c(Br)c2[nH]c(Nc3ccc4ccccc4c3)nc2c1Br] |
| 261 | 4,5,6,7-tetrabromo-N-cyclooctyl-1H-benzo[d]imidazol-2-amine; $C_{15}H_{17}Br_4N_3$ (MW 558.93) General procedure (° C.; rt = h); m/z 559.8 [M + H]+; RT = 21.1 min | 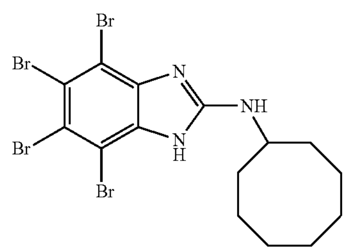 [SMILES: Brc1c(Br)c(Br)c2[nH]c(NC3CCCCCCC3)nc2c1Br] |
| 263 | N-(4,5,6,7-tetrabromo-1H-benzo[d]imidazol-2-yl)-N'-methyl-N'-(1-methylpiperidin-4-yl)-1-phenylethane-1,2-diamine; $C_{22}H_{25}Br_4N_5$ (MW 679.08) General procedure (° C.; rt = h); m/z 679.9 [M + H]+; RT = 5.4 min | 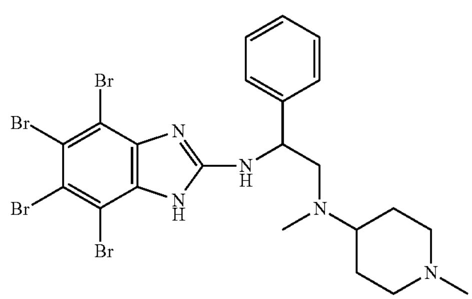 [SMILES: CN1CCC(N(C)CC(Nc2nc3c(Br)c(Br)c(Br)c(Br)c3[nH]2)c2ccccc2)CC1] |
| 265a | 4,5,6,7-tetrabromo-N-((1-ethylpyrrolidin-2-yl)methyl)-1H-benzo[d]imidazol-2-amine; $C_{14}H_{16}Br_4N_4$ (MW 559.92) General procedure A: m/z 560.8 [M + H]+; RT = 7.3 min | 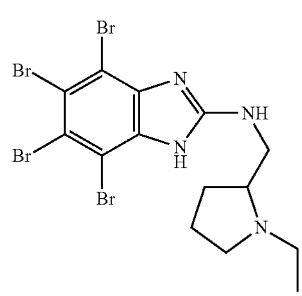 [SMILES: CCN1CCCC1CNc1nc2c(Br)c(Br)c(Br)c(Br)c2[nH]1] |

TABLE 2-continued

Example list II (Formula B)

| Compound number | Name | Structure |
|---|---|---|
| 271 | N-(5-(1H-imidazol-2-yl)-4-phenylthiazol-2-yl)-4,5,6,7-tetrabromo-1H-benzo[d]imidazol-2-amine; C$_{19}$H$_{10}$Br$_4$N$_6$S (MW 674.0) General procedure A; m/z 674.7 [M + H]$^+$; RT = 10.8 min | 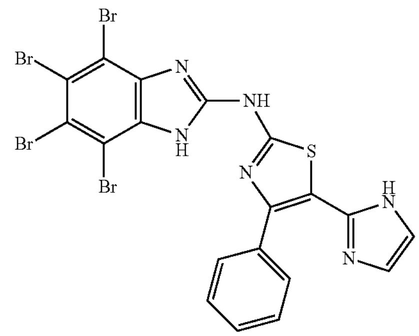 [SMILES: Brc1c(Br)c(Br)c2[nH]c(Nc3nc(-c4ccccc4)c(-c4ncc[nH]4)s3)nc2c1Br] |
| 272 | 2-((4,5,6,7-tetrabromo-1H-benzo[d]imidazol-2-ylamino)methyl)-3-(dimethylamino)-1-phenylpropan-1-ol; C$_{19}$H$_{20}$Br$_4$N$_4$O (MW 640.0) General procedure A; m/z 640.8 [M + H]$^+$; RT = 7.8 min | 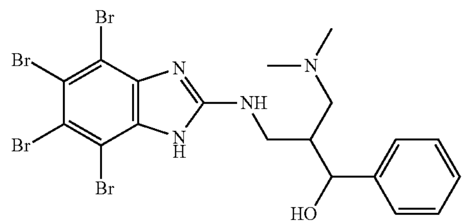 [SMILES: CN(C)CC(CNc1nc2c(Br)c(Br)c(Br)c(Br)c2[nH]1)C(O)c1ccccc1] |
| 296 | N-(3,4-difluorobenzyl)-4,5,6,7-tetrabromo-1H-benzo[d]imidazol-2-amine; C$_{14}$H$_7$Br$_4$F$_2$N$_3$ (MW 574.84) General procedure A; m/z 575.7 [M + H]$^+$; RT = 18.7 min | 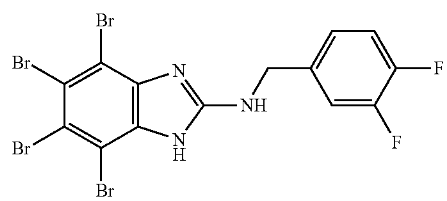 [SMILES: Fc1ccc(CNc2nc3c(Br)c(Br)c(Br)c(Br)c3[nH]2)cc1F] |
| 303 | 5-(4,5,6,7-tetrabromo-1H-benzo[d]imidazol-2-ylamino)pyrimidine-2,4-diol; C$_{11}$H$_5$Br$_4$N$_5$O$_2$ (MW 558.81) General procedure A; m/z 559.7 [M + H]$^+$; RT = 11.4 min | 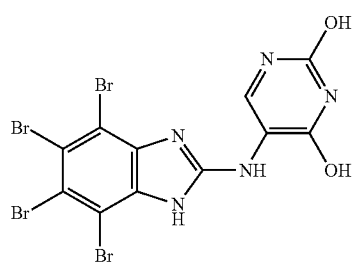 [SMILES: Oc1ncc(Nc2nc3c(Br)c(Br)c(Br)c(Br)c3[nH]2)c(O)n1] |
| 304cis | cis N1-(4,5,6,7-tetrabromo-1H-benzo[d]imidazol-2-yl)cyclohexane-1,2-diamine; C$_{13}$H$_{14}$Br$_4$N$_4$ (MW 545.89) General procedure A; m/z 546.8 [M + H]$^+$; RT = 6.3 min | 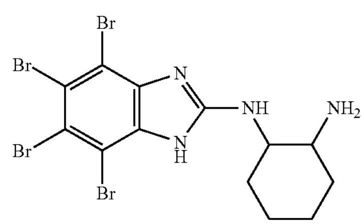 [SMILES: NC1CCCCC1Nc1nc2c(Br)c(Br)c(Br)c(Br)c2[nH]1] |
| 304RR | (1R,2R)-N1-(4,5,6,7-tetrabromo-1H-benzo[d]imidazol-2-yl)cyclohexane-1,2-diamine; C$_{13}$H$_{14}$Br$_4$N$_4$ (MW 545.89) General procedure A; m/z 546.8 [M + H]$^+$; RT = 6.3 min | 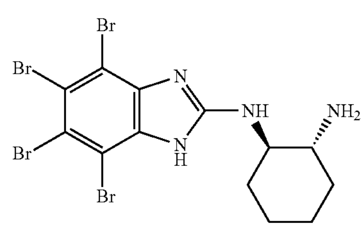 [SMILES: N[C@@H]1CCCC[C@H]1Nc1nc2c(Br)c(Br)c(Br)c(Br)c2[nH]1] |

TABLE 2-continued

Example list II (Formula B)

| Compound number | Name | Structure |
|---|---|---|
| 304SS | (1S,2S)-N1-(4,5,6,7-tetrabromo-1H-benzo[d]imidazol-2-yl)cyclohexane-1,2-diamine; $C_{13}H_{14}Br_4N_4$ (MW 545.89) General procedure A; m/z 546.7 $[M + H]^+$; R = 6.6 min | 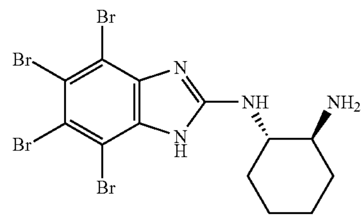 [SMILES: N[C@H]1CCCC[C@@H]1Nc1nc2c(Br)c(Br)c(Br)c(Br)c2[nH]1] |
| 304trans | Trans N1-(4,5,6,7-tetrabromo-1H-benzo[d]imidazol-2-yl)cyclohexane-1,2-diamine; $C_{13}H_{14}Br_4N_4$ (MW 545.89) General procedure A; m/z 546.7 $[M + H]^+$; RT = 6.4 min | 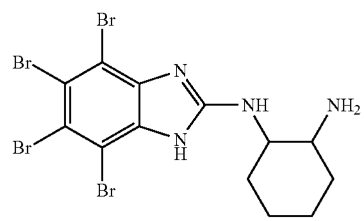 [SMILES: NC1CCCCC1Nc1nc2c(Br)c(Br)c(Br)c(Br)c2[nH]1] |
| 307 | 4,5,6,7-tetrabromo-N-(3,4-dimethoxyphenyl)-1H-benzo[d]imidazol-2-amine; $C_{15}H_{11}Br_4N_3O_2$ (MW 584.88) General procedure A; m/z 585.8 $[M + H]^+$; RT = 18.2 min | 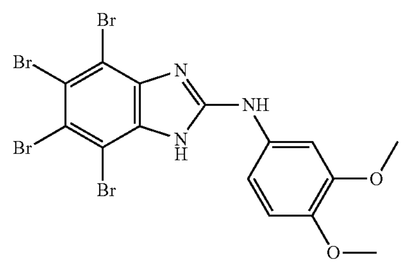 [SMILES: COc1ccc(Nc2nc3c(Br)c(Br)c(Br)c(Br)c3[nH]2)cc1OC] |
| 309 | 4-(4,5,6,7-tetrabromo-1H-benzo[d]imidazol-2-ylamino)cyclohexanol; $C_{13}H_{13}Br_4N_3O$ (MW 546.88) General procedure A; m/z 547.8 $[M + H]^+$; RT = 9.9 min | 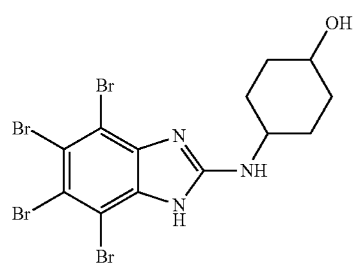 [SMILES: OC1CCC(Nc2nc3c(Br)c(Br)c(Br)c(Br)c3[nH]2)CC1] |
| 317 | 4,5-dibromo-N1-(4,5,6,7-tetrabromo-1H-benzo[d]imidazol-2-yl)benzene-1,2-diamine; $C_{13}H_6Br_6N_4$ (MW 697.64) General procedure A; m/z 698.5 $[M + H]^+$; RT = 20.8 min | 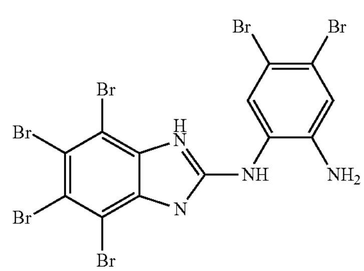 |
| 328 | N1-(4,5,6,7-tetrabromo-1H-benzo[d]imidazol-2-yl)-4,5-dimethylbenzene-1,2-diamine; $C_{15}H_{12}Br_4N_4$ (MW 567.90) General procedure A; m/z 566.9 $[M - H]^-$; | 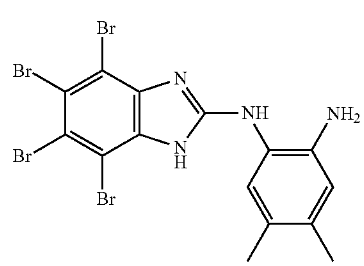 [SMILES: Cc1cc(N)c(Nc2nc3c(Br)c(Br)c(Br)c(Br)c3[nH]2)cc1C] |

TABLE 2-continued

Example list II (Formula B)

| Compound number | Name | Structure |
|---|---|---|
| 329 | 4,5,6,7-tetrabromo-N-(pyridin-2-yl)-1H-benzo[d]imidazol-2-amine; C₁₂H₆Br₄N₄ (MW 525.82) General procedure A; m/z 526.7 [M + H]⁺; RT = 15.2 min | 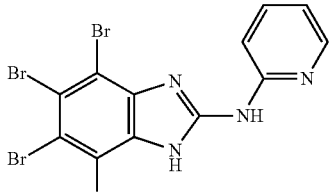 |
| 331 | Trans N1-(4,5,6,7-tetrabromo-1H-benzo[d]imidazol-2-yl)cyclohex-4-ene-1,2-diamine; C₁₃H₁₂Br₄N₄ (MW 543.88) General procedure A; m/z 544.7 [M + H]⁺; RT = 6.4 min | 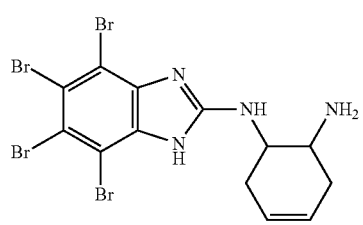 [SMILES: NC1CC=CCC1Nc1nc2c(Br)c(Br)c(Br)c(Br)c2[nH]1] |
| 332 | N1-(4,5,6,7-tetrabromo-1H-benzo[d]imidazol-2-yl)benzene-1,2-diamine; C₁₃H₈Br₄N₄ (MW 539.84) General procedure A; m/z 540.8 [M + H]⁺; RT = 14.0 min | 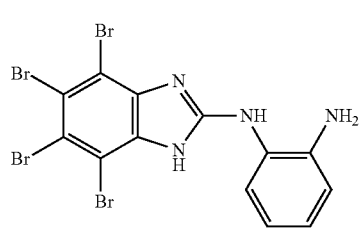 [SMILES: Nc1ccccc1Nc1nc2c(Br)c(Br)c(Br)c(Br)c2[nH]1] |
| 333 | N1-(4,5,6,7-tetrabromo-1H-benzo[d]imidazol-2-yl)-4,5-difluorobenzene-1,2-diamine; C₁₃H₆Br₄F₂N₄ (MW 575.83) General procedure A; m/z 576.8 [M + H]⁺; RT = 17.9 min | 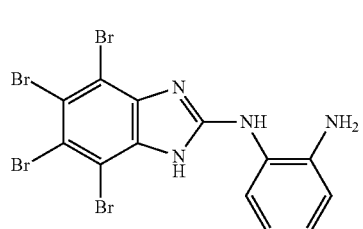 |
| 334 | 2-(4,5,6,7-tetrabromo-1H-benzo[d]imidazol-2-ylamino)cyclohexanol; C₁₃H₁₃Br₄N₃O (MW 546.88) General procedure A; m/z 547.7 [M + H]⁺; RT = 13.5 min | 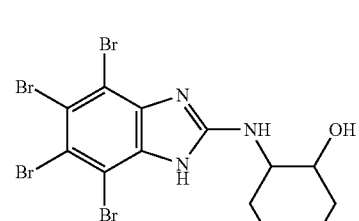 |
| 336 | N1-(4,5,6,7-tetrabromo-1H-benzo[d]imidazol-2-yl)cyclohexane-1,3-diamine; C₁₃H₁₄Br₄N₄ (MW 545.89) General procedure A; m/z 546.7 [M + H]⁺; RT = 5.8 min | 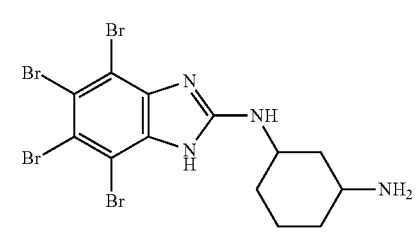 [SMILES: NC1CCCC(Nc2nc3c(Br)c(Br)c(Br)c(Br)c3[nH]2)C1] |

TABLE 2-continued

Example list II (Formula B)

| Compound number | Name | Structure |
|---|---|---|
| 337 | 4,5,6,7-tetrabromo-N-((3R,4R)-tetrahydro-4-(pyrrolidin-1-yl)furan-3-yl)-1H-benzo[d]imidazol-2-amine; $C_{15}H_{16}Br_4N_4O$ (MW 587.93) General procedure A; m/z 588.9 [M + H]$^+$; RT = 6.7 min | 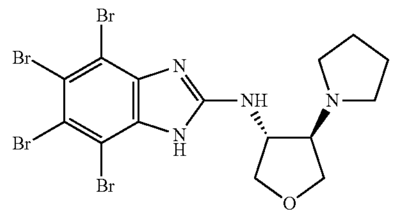 [SMILES: Brc1c(Br)c(Br)c2[nH]c(N[C@H]3COC[C@@H]3N3CCCC3)nc2c1Br] |
| 338 | 4,5,6,7-tetrabromo-N-((3R,4R)-tetrahydro-4-(piperidin-1-yl)furan-3-yl)-1H-benzo[d]imidazol-2-amine; $C_{16}H_{18}Br_4N_4O$ (MW 601.96) General procedure A; m/z 602.8 [M + H]$^+$; RT = 7.2 min | 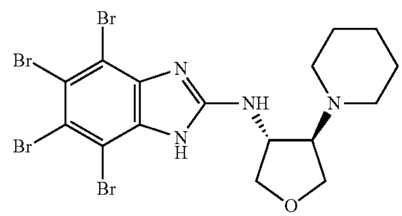 [SMILES: Brc1c(Br)c(Br)c2[nH]c(N[C@H]3COC[C@@H]3N3CCCCC3)nc2c1Br] |
| 340 | N11-(4,5,6,7-tetrabromo-1H-benzo[d]imidazol-2-yl)-9,10-dihydro-9,10-ethanoanthracene-11,12-diamine; $C_{23}H_{16}Br_4N_4$ (MW 668.02) General procedure A; m/z 668.6 [M + H]$^+$; RT = 8.5 min | 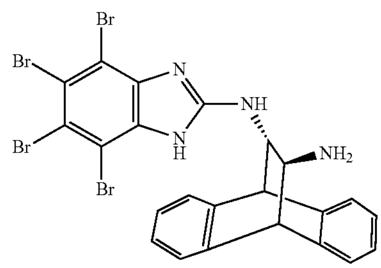 [SMILES: N[C@H]1C2c3ccccc3C(c3ccccc32)[C@@H]1Nc1nc2c(Br)c(Br)c(Br)c(Br)c2[nH]1] |
| 342 | 4,5,6,7-tetrabromo-N-methyl-N-phenyl-1H-benzo[d]imidazol-2-amine; $C_{14}H_9Br_4N_3$ (MW 538.86) General procedure A; m/z 539.8 [M + H]$^+$; RT = 19.9 min | 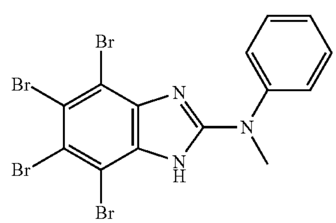 [SMILES: CN(c1ccccc1)c1nc2c(Br)c(Br)c(Br)c(Br)c2[nH]1] |
| 349 | N-(2-(aminomethyl)benzyl)-4,5,6,7-tetrabromo-1H-benzo[d]imidazol-2-amine; $C_{15}H_{12}Br_4N_4$ (MW 567.90) General procedure A; m/z 568.7 [M + H]$^+$; RT = 6.2 min | 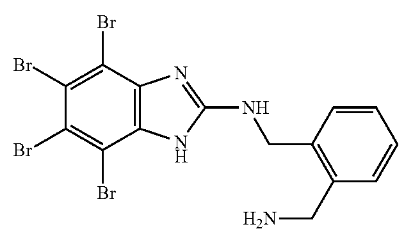 [SMILES: NCc1ccccc1CNc1nc2c(Br)c(Br)c(Br)c(Br)c2[nH]1] |
| 354 | N-(3-(aminomethyl)benzyl)-4,5,6,7-tetrabromo-1H-benzo[d]imidazol-2-amine; $C_{15}H_{12}Br_4N_4$ (MW 567.9) General procedure A; m/z 568.6 [M + H]$^+$; RT = 6.2 min | 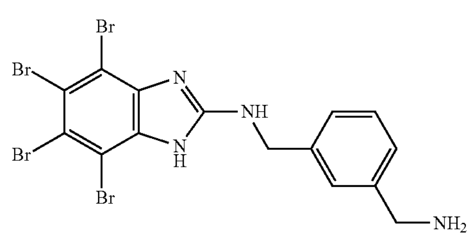 [SMILES: NCc1cccc(CNc2nc3c(Br)c(Br)c(Br)c(Br)c3[nH]2)c1] |

TABLE 2-continued

Example list II (Formula B)

| Compound number | Name | Structure |
|---|---|---|
| 358 | 4,5,6,7-tetrabromo-N-(1-methylazepan-4-yl)-1H-benzo[d]imidazol-2-amine; $C_{14}H_{16}Br_4N_4$ (MW 559.92) General procedure A; m/z 560.7 $[M + H]^+$; RT = 5.6 min | 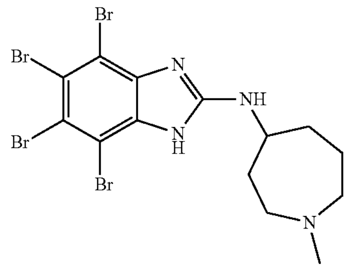 [SMILES: CN1CCCC(Nc2nc3c(Br)c(Br)c(Br)c(Br)c3[nH]2)CC1] |
| 366 | N-(azepan-4-yl)-4,5,6,7-tetrabromo-1H-benzo[d]imidazol-2-amine; $C_{13}H_{14}Br_4N_4$ (MW 545.89) General procedure A; m/z 546.7 $[M + H]^+$; RT = 5.3 min | 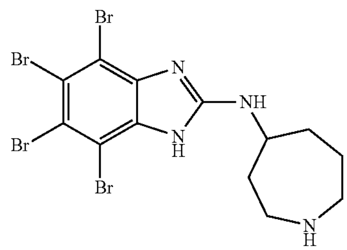 [SMILES: Brc1c(Br)c(Br)c2[nH]c(NC3CCCNCC3)nc2c1Br] |
| 369 | N1-(4,5,6,7-tetrabromo-1H-benzo[d]imidazol-2-yl)-N2-isopropylcyclohexane-1,2-diamine; $C_{16}H_{20}Br_4N_4$ (MW 587.97) General procedure A; m/z 588.7 $[M + H]^+$; RT = 7.4 min | 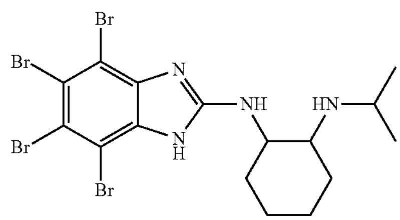 [SMILES: CC(C)NC1CCCCC1Nc1nc2c(Br)c(Br)c(Br)c(Br)c2[nH]1] |
| 372 | N-benzyl-4,5,6,7-tetrabromo-N-(3-(methylamino)propyl)-1H-benzo[d]imidazol-2-amine; $C_{18}H_{18}Br_4N_4$ (MW 609.98) General procedure A; m/z 610.7 $[M + H]^+$; RT = 8.1 min | 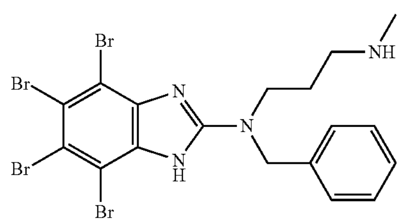 [SMILES: CNCCCN(Cc1ccccc1)c1nc2c(Br)c(Br)c(Br)c(Br)c2[nH]1] |
| 380 | N1-(4,5,6,7-tetrabromo-1H-benzo[d]imidazol-2-yl)-N2-methylcyclohexane-1,2-diamine; $C_{15}H_{18}Br_4N_4$ (MW 573.94) General procedure D; m/z 574.7 $[M + H]^+$; RT = 7.0 min | 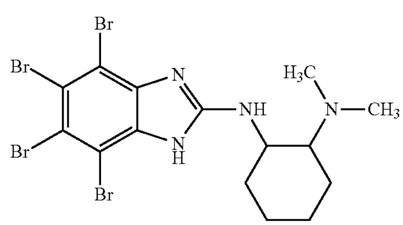 [SMILES: CN(C)C1CCCCC1Nc1nc2c(Br)c(Br)c(Br)c(Br)c2[nH]1] |
| 381 | N-(2-(4,5,6,7-tetrabromo-1H-benzo[d]imidazol-2-ylamino)cyclohexyl)acetamide; $C_{15}H_{16}Br_4N_4O$ (MW 587.93) General procedure D; m/z 588.7 $[M + H]^+$; RT = 13.6 min | 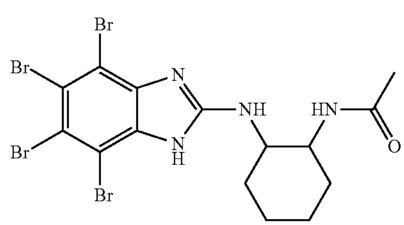 [SMILES: CC(=O)NC1CCCCC1Nc1nc2c(Br)c(Br)c(Br)c(Br)c2[nH]1] |

TABLE 2-continued

Example list II (Formula B)

| Compound number | Name | Structure |
|---|---|---|
| 413 | N1-(4,5,6,7-tetrabromo-1H-benzo[d]imidazol-2-yl)-N2-pentylcyclohexane-1,2-diamine; $C_{18}H_{24}Br_4N_4$ (MW 616.03) General procedure D; m/z 616.8 $[M + H]^+$; RT = 9.3 min | 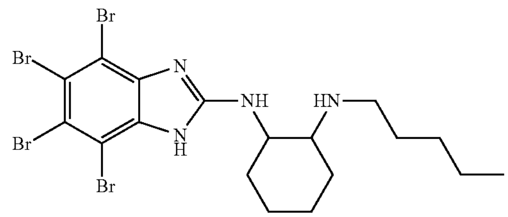 [SMILES: CCCCCNC1CCCCC1Nc1nc2c(Br)c(Br)c(Br)c(Br)c2[nH]1] |
| 435 | 4,5,6,7-tetrabromo-N-(piperidin-4-yl)-1H-benzo[d]imidazol-2-amine; $C_{12}H_{12}Br_4N_4$ (MW 531.87) General procedure A; m/z 532.8 $[M + H]^+$; RT = 5.7 min | 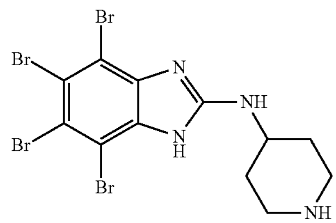 [SMILES: Brc1c(Br)c(Br)c2[nH]c(NC3CCNCC3)nc2c1Br] |

Preferably, a pharmaceutically acceptable salt is selected from the group consisting of hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate and the like.

A "pharmaceutically-acceptable salt" is a cationic salt formed at any acidic (e.g. carboxylic acid) group, or an anionic salt formed at any basic (e.g. amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like.

The next subject of invention is a pharmaceutical composition, comprising a therapeutically effective amount of at least one compound selected from the group consisting of compounds as described above and optionally comprising a therapeutic agent selected from a chemotherapeutic or antiproliferative agent, an immunomodulatory or immunosuppressive agent, or an anti-inflammatory agent.

The term "composition" is intended to encompass a product comprising the specified ingredients in the specified amounts, as well as any product which results, directly or indirectly, from combinations of the specified ingredients in the specified amounts. The active agents of the invention are used, alone or in combination with one or more additional active ingredients, to formulate pharmaceutical compositions of the invention. A pharmaceutical composition of the invention comprises an effective amount of at least one active agent in accordance with the invention. As known in pharmaceutical technology, at least one pharmaceutically acceptable carrier may be comprised in embodiments of pharmaceutical compositions according to this invention. A carrier may also be denoted as excipient in the following.

Preferably, the said composition optionally comprises a therapeutic agent selected from a chemotherapeutic or antiproliferative agent, an immunomodulatory or immunosuppressive agent, or an anti-inflammatory agent.

Preferably, the therapeutically effective amount provided in the treatment is administered in an amount of about 0.01 to 1,000 mg/kg at least once a day for the duration of the treatment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of a disease or disorder. When referring to modulating the target receptor, a "therapeutically effective amount" means an amount sufficient to at least affect the activity of such receptor. Measuring the activity of the target kinase may be performed by routine analytical methods. Target kinase modulation is useful in a variety of settings, including assays. In addition, effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

The amount varies according to the size, age and response pattern of the patient, the severity of the disorders, the judgment of the attending physician and the like.

Preferably, the said composition is administered parenterally, vaginally, rectally, transdermally, orally or through the otolaryngogal sphere.

Preferably, it further comprises a pharmaceutically acceptable carrier selected from the group consisting of flavoring agents, sweetener, lubricants, solubilizers, suspending agents, fillers, glidants, compression aides, binders, tablet-disintegrating agents, effervescing agent, wetting agent encapsulating materials, dyestuff, and mixtures thereof wherein carrier is chosen from solid or liquid carriers, whether sterile or not.

Preferably, the said composition optionally further comprises of one or more additional pharmaceutically acceptable carriers selected from the group consisting of a flavoring agents, sweeteners, binders, diluents, solubilizer, lubricants, suspending agents, fillers, glidants, compression aides, disintegrating agents, effervescing agents, dyestuffs, wetting agents or encapsulating materials and mixtures thereof wherein carrier is chosen from solid or liquid carriers, whether sterile or not. In powders, the carrier and compound is a finely divided solid. In tablets, said compound is mixed with a carrier having the necessary compression properties in suitable proportions and compacted in the shape and size desired. Said powders and tablets contain from 0.1 to 99% by weight of the compound. Solid carriers suitable for use in the composition of the invention include but are not limited to calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs can be employed in the composition of the invention. Is that case, the compound is dissolved or suspended in a pharmaceutically acceptable liquid carrier such as water, an organic solvent, or pharmaceutically acceptable oil or fat, or a mixture thereof. Said liquid composition contain additionally or not other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like.

Examples of liquid carriers suitable for oral and parenteral administration include water, particularly containing additives as above but not limited to cellulose derivatives, preferably sodium carboxymethyl cellulose solution, alcohols, including monohydric alcohols and polyhydric alcohols, such as glycols or their derivatives, or oils such as fractionated coconut oil, cottonseed oil and arachid oil. For parenteral administration the carrier may also be an oily ester such as ethyl oleate or isopropyl myristate.

Preferably, the said composition is a sterile solution or suspension suitable for parenteral administration, including but not limited to intramuscular, intraperitoneal, intravenous, intrathecal or subcutaneous injection or perfusion.

Preferably the pharmaceutical composition is suitable for oral administration either liquid or solid composition form, including pills, tablets, capsules, sachets, dragees, powders, granules, lozenges, powders for reconstitution, orally disintegrating tablet, films, osmotic controlled release capsule, elixir, emulsion, syrup, suspension, tincture, solutions or powder for inhalation and nebulization, or sublingual administration.

Preferably, the said composition is a formulation for transdermal, rectal, vaginal administration, including ointments, creams, lotions, liniments, gels, paste, films, suppositories, enemas and pessaries.

Preferably, the said composition is a formulation for administration through the eyes, ears and nose.

Preferably, the composition is an immediate, extended or slow-release formulation.

Preferably, the therapeutically effective amount is provided in the treatment of a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis. Thus, the terms "cancer", "neoplasm" or "neoplastic," as provided herein, refer to a cell afflicted by any one of the above-identified conditions but are not limited thereto.

Preferably, it is for the prevention or treatment of neoplastic conditions, especially related with the modulation or regulation of serine/threonine or tyrosine kinases, preferably selected from the group of PIM, HIPK, DYRK, CLK, CDK, FLT, PKG, Haspin, MER, TAO, MNK and TRK kinases.

Serine/threonine and tyrosine kinases inhibitors disclosed in this application may also be used for treating immune disorders such as but not limited to bone marrow transplant rejection, rheumatoid arthritis, psoriasis, type I diabetes mellitus, multiple sclerosis. Inhibition of serine/threonine and tyrosine kinases can be also used for treatment of infectious diseases exemplified by but not limited to infections with herpesiviruses.

The next subject of invention is a use of the compound of Formula A and B for the preparation of a pharmaceutical composition comprising a therapeutically effective amount of at least one compound selected from the group consisting of compounds as described above and optionally comprising a therapeutic agent selected from a chemotherapeutic or anti-proliferative agent, an immunomodulatory or immunosuppressive agent, or an anti-inflammatory agent.

Preferably, it is used for the prevention or treatment of neoplastic or immune conditions, especially related to the modulation or regulation of serine/threonine and tyrosine kinases, preferably selected from the group of PIM, HIPK, DYRK, CLK, CDK, FLT, PKG, Haspin, MER, TAO, MNK and TRK kinases.

Preferably, for preventing or treating neoplastic conditions selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma; leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

The next subject of invention is a method for modulating or regulating serine/threonine or tyrosine kinases, preferably selected from the group of PIM, HIPK, DYRK, CLK, CDK, FLT, PKG, Haspin, MER, TAO, MNK and TRK kinases, wherein serine/threonine or tyrosine kinases are exposed to an effective amount of at least one compound of Formula A or B, an enantiomer thereof or a mixture of its enantiomers or pharmaceutically acceptable salts of compounds of Formula A and B or pharmaceutically acceptable prodrugs of compounds of Formula A and B, or pharmaceutically active metabolites of compounds of Formula A and B as described above.

Preferably, serine/threonine or tyrosine kinases, preferably kinases selected from the group of PIM, HIPK, DYRK, CLK, CDK, FLT, PKG, Haspin, MER, TAO, MNK and TRK kinases is in a subject with a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

The next subject of invention is a serine/threonine or tyrosine kinases modulating agent as described above, characterized in that kinases are preferably selected from the group of PIM, HIPK, DYRK, CLK, CDK, FLT, PKG, Haspin, MER, TAO, MNK and TRK kinases wherein kinases are exposed to an effective amount of at least one compound of Formula A and B, an enantiomer thereof or a mixture of its enantiomers or pharmaceutically acceptable salts of compounds of Formula A and B or pharmaceutically acceptable prodrugs of compounds of Formula A and B, or pharmaceutically active metabolites of compounds of Formula A and B as described above.

Preferably, serine/threonine or tyrosine kinases are preferably kinases selected from the group of PIM, HIPK, DYRK, CLK, CDK, FLT, PKG, Haspin, MER, TAO, MNK and TRK kinases and their isoforms is in a subject with a disease, disorders or medical condition that is selected from the group consisting of myeloid leukemia both acute and chronic, acute lymphoblastic leukemia, chronic lymphocytic leukemia, hairy cell leukemia, myeloproliferative diseases, multiple myeloma, myelodysplastic syndrome, Hodgkin's disease, non-Hodgkin's lymphoma (malignant lymphoma); adenocarcinoma, lymphoma, leukemia of the kidney, Wilm's tumor, renal cell carcinoma, renal pelvis carcinoma, nephroma, teratoma, sarcoma of the kidney, squamous cell carcinoma, transitional cell carcinoma, adenocarcinoma of bladder and urethra, adenocarcinoma, sarcoma of the prostate, seminoma, teratoma, embryonal carcinoma, teratocarcinoma, choriocarcinoma, sarcoma, interstitial cell carcinoma, fibroma, fibroadenoma, adenomatoid tumors, lipoma of the testis; angiosarcoma, fibrosarcoma, rhabdomyosarcoma, liposarcoma, myxoma, rhabdomyoma, fibroma, lipoma and teratoma of the heart; astrocytoma, medulloblastoma, glioma, ependymoma, germinoma (pinealoma), glioblastoma multiform, oligodendroglioma, schwannoma, retinoblastoma, congenital tumors of the brain, neurofibroma, meningioma, glioma, sarcoma of the spinal cord, osteoma, hemangioma, granuloma, xanthoma, osteitis deformans of the skull, meningioma, meningiosarcoma, gliomatosis of the meninges; squamous cell, undifferentiated small cell, undifferentiated large cell, adenocarcinoma, alveolar carcinoma, bronchial adenoma, sarcoma, lymphoma, chondromatous hanlartoma, mesothelioma of the bronchus; adenocarcinoma, lymphoma, carcinoid tumors, Karposi's sarcoma, leiomyoma, hemangioma, lipoma, neurofibroma, fibroma of the small bowel, adenocarcinoma, tubular adenoma, villous adenoma, hamartoma, leiomyoma of the large bowel; squamous cell carcinoma, adenocarcinoma, leiomyosarcoma, lymphoma of the esophagus, carcinoma, lymphoma, leiomyosarcoma of the stomach, ductal adenocarcinoma, insulinoma, glucagonoma, gastrinoma, carcinoid tumors, vipoma of the pancreas; hepatocellular carcinoma, cholangiocarcinoma, hepatoblastoma, angiosarcoma, hepatocellular adenoma, hemangioma of the liver; osteogenic sarcoma, fibrosarcoma, malignant fibrous histiocytoma, chondrosarcoma, Ewing's sarcoma, malignant lymphoma such as reticulum cell sarcoma, multiple myeloma, malignant giant cell tumor chordoma, osteochronfroma such as osteocartilaginous exostoses, benign chondroma, chondroblastoma, chondromyxofibroma, osteoid osteoma and giant cell tumors; endometrial carcinoma, cervical carcinoma, pre-tumor cervical dysplasia, ovarian carcinoma such as serous cystadenocarcinoma, mucinous cystadenocarcinoma, unclassified carcinoma, granulosa-thecal cell tumors, Sertol/Leydig cell tumors, dysgerminoma, malignant teratoma of the ovary, squamous cell carcinoma, intraepithelial carcinoma, adenocarcinoma, fibrosarcoma, melanoma of the vulva, clear cell carcinoma, squamous cell carcinoma, botryoid sarcoma such as embryonal rhabdomyosarcoma of the vagina, fallopian tubes carcinoma), breast; and malignant melanoma, basal cell carcinoma, squamous cell carcinoma, Karposi's sarcoma, moles dysplastic nevi, lipoma, angioma, dermatofibroma, keloids, bone marrow transplant rejection, rheumatoid arthritis, psoriasis, type I diabetes mellitus and multiple sclerosis.

The next subject of invention is a process for the preparation compound according to the above characterized in that the process comprise: reacting of a corresponding, unsubstituted or substituted 2,4,5,6,7-pentabromo-benzimidazole with a suitable amine at elevated temperature, wherein the reactive substituents are optionally protected with suitable protecting groups and wherein the resulting product is subjected to purification by crystallization or chromatography according to the reaction as shown in Reaction scheme 1 below.

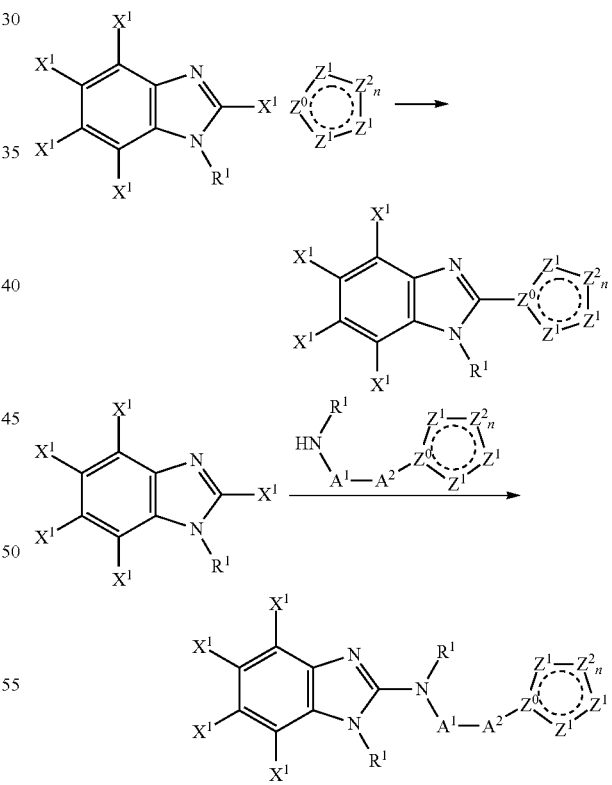

Reaction Scheme 1

Reaction Scheme 1:
synthetic route of production of a compound by reacting an unsubstituted or substituted 2,4,5,6,7-pentahalogenated-benzimidazole with a suitable amine. While particular embodiments of the present disclosure have been illustrated as examples it is obvious to those skilled in the art that various additional changes can be introduced without departing from the spirit and scope of the disclosure. It is therefore intended to cover in the appended claims all such changes and modifications that are within spirit and scope of the disclosure.

Below, there are example embodiments of the present invention defined above.

EXAMPLES

The following specific Examples are set forth to illustrate the invention and to aid in the understanding of the invention, and are not intended and should not be construed to limit in any way the invention set forth in the claims which follow thereafter.

The invention relates to compounds comprised by Formula A and B, with examples presented in Table 1 and 2 and their pharmaceutically acceptable salts, and pharmaceutically acceptable prodrugs.

General Synthetic Procedure A 1 equivalent of appropriate derivative of 2,4,5,6,7-pentabromobenzimidazole suspended in ethanol was heated at 120° C. together with 5 equivalents of appropriate amine in a sealed tube for 5 to 20 hours. Alternatively, the reaction can be carried in butanol reflux. Product was isolated using crystallization or flash chromatography.

General Synthetic Procedure B 1 equivalent of 4,5,6,7-tetrabromo-2-(piperazin-1-yl)-1H-benzo[d]imidazole or N-(3-aminopropyl)-4,5,6,7-tetrabromo-1H-benzo[d]imidazol-2-amine was suspended in DMF with 2 equivalents of DIPEA. Suspension was cooled to 0° C. and then 2 equivalents of 1H-pyrazole-1-carboximidamide were added. The reaction mixture (RM) was stirred for 4 hours and then NaOH was added. Solid product was filtered and washed with distilled water.

General Synthetic Procedure C 1 equivalent of 4,5,6,7-tetrabromo-2-(piperazin-1-yl)-1H-benzo[d]imidazole was suspended in EtOH with 2 equivalents of appropriate halogeno derivative and 2 eq of $K_2CO_3$. RM was refluxed for 2-16 hours. Product was isolated using crystallization or flash chromatography.

General Synthetic Procedure D 1 equivalent of N1-(4,5,6,7-tetrabromo-1H-benzo[d]imidazol-2-yl)cyclohexane-1,2-diamine and 1 eq of appropriate ketone or aldehyde derivative were suspended in DCE and then 2 eq of $NaBH(OAc)_3$ and 1 eq of AcOH were added. Solution was stirred at room temperature for 24 hours. Product was isolated using crystallization or flash chromatography.

Example 1

Growth Inhibition Test on Human Chronic Myelocytic Leukemia K562 Cells—Results Summarized in Table 4

Ten thousand cells of human chronic myelocytic leukemia K562 were inoculated into each well of a 96-well microplate (manufactured by Corning Corp.) using Iscove's MDM medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 µl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 2

Growth Inhibition Test on Human Prostate Adenocarcinoma PC3 Cells—Results Summarized in Table 4

Two thousand cells of human prostate adenocarcinoma PC3 were inoculated into each well of a 96-well microplate (manufactured by Corning Corp.), and using F12K (Ham's F12:RPMI 8226 1:1) medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 µl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 3

Growth Inhibition Test on Human Prostate Carcinoma DU145 Cells—Results Summarized in Table 4

Two thousand cells of human prostate carcinoma DU145 were inoculated into each well of a 96-well microplate (manufactured by Corning Corp.), and using DMEM medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 µl MTS (3-(4,5-Dimethyl- 2-thiazolyl)-5-(carboxymethoxyphenyl)-2-(4-sulfophenyl)-2H-tetrazolium, innersalt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 4

Growth Inhibition Test on Human Breast Adenocarcinoma MCF7 Cells—Results Summarized in Table 4

Two thousand cells of human breast adenocarcinoma MCF7 were inoculated into each well of a 96-well microplate (manufactured by Corning Corp.), and using DMEM medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 µl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 5

Growth Inhibition Test on Human Colorectal Adenocarcinoma SW480 Cells—Results Summarized in Table 4

Two thousand cells of human colorectal adenocarcinoma SW480 were inoculated into each well of a 96-well microplate (manufactured by Corning Corp.), and using DMEM/Ham's F121:1 medium (culture medium) containing 5% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 µl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 6

Growth Inhibition Test on Human Myelomonocytic, Biphenotypic Leukemia MV4-11 Cells—Results Summarized in Table 4

Ten thousand cells of human myelomonocytic, biphenotypic leukemia MV4-11 were inoculated into each well of a 96-well microplate (manufactured by Corning Corp.) using Iscove's MDM medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 µl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 7

Growth Inhibition Test on Human Acute Lymphocytic Leukemia E6.1 Jurkat Cells—Results Summarized in Table 4

Twenty thousand cells of human acute lumphocytic leukemia E6.1 Jurkat were inoculated into each well of a 96-well microplate (manufactured by Corning Corp.) using RPMI 8226 medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 µl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 8

Growth Inhibition Test on Human Hepatoma HepG2 Cells—Results Summarized in Table 4

Two thousand cells of human hepatoma HepG2 were inoculated into each well of a 96-well microplate (manufactured by Corning Corp.) using DMEM medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 μl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 9

Growth Inhibition Test on Human Erytroblast Leukemia HEL-92.1.7 cells—Results Summarized in Table 4

Ten thousand cells of human erytroblast leukemia HEL-92.1.7 were inoculated into each well of a 96-well microplate (manufactured by Corning Corp.) using RPMI 1640 medium (culture medium) containing 10% fetal calf serum (FCS). Next day, a dimethyl sulfoxide (DMSO) solution of each test compound prepared in a concentration of 10 mmol/L was further diluted with culture medium to the desired concentrations (0.1, 0.5, 1, 2.5, 5 and 10 micromol/L), and the diluted solution was added to each well. The individual wells were further cultured in 5% carbon dioxide at 37° C. for 72 hours. After completion of the culture, 10 μl MTS (3-(4,5-Dimethyl-2-thiazolyl)-5-(carboxymethoxyphenyl)-2-(4-sulfophenyl)-2H-tetrazolium, inner salt assay (CellTiter96® AQueous One Solution Cell Proliferation Assay, Promega) was added to each well, and culturing was performed in 5% carbon dioxide at 37° C. for 2 hours. Using a microplate spectrophotometer (Synergy 2 multi-mode microplate reader (BioTek)), the absorbance of each well was measured at 490 nm. The value for cells not incorporated with a test compound was designated as 100%. By comparing these values with the absorbance difference obtained at the well in which each test compound was added, the cell viability (% viability) after treatment with the test compound was calculated.

Example 10

Luminometric Kinase Assay for PIM1 Kinase—Results Summarized in Table 4

Kinase assay was performed using luminescent Kinase-Glo® (Promega) system. The Kinase-Glo® Luminescent Kinase Assay Platform provides a homogeneous, high-throughput screening method for measuring kinase activity by quantifying the amount of ATP remaining in solution following a kinase reaction. The luminescent signal is correlated with the amount of ATP present and is inversely correlated with the kinase activity. Appropriate amounts of both kinase and substrate were mixed in 96-well, white wall plate in the reaction buffer (8 mM MOPS/NaOH, pH7.0, 0.2 mM EDTA, 2 mM $MgCl_2$). Tested compounds were diluted in DMSO and serial dilutions starting with 1 μM were added to the palates. Reaction was initiated by adding 1 μM of ATP solution and conducted for 25 min. at RT. Luminescent signal was detected by adding Kinase-Glo® reagent and measured using a microplate spectrophotometer (Synergy 2 multi-mode microplate reader (BioTek)). IC50 values were obtained by fitting sigmoidal dose-response curve (variable slope) using GraphPad Prism software.

Reaction conditions are presented in Table 3.

TABLE 3

Reaction conditions for luminometric kinase assay.

| Kinase | Kinase concentration | Peptide substrate sequence | Peptide concentration | ATP concentration |
|---|---|---|---|---|
| PIM-1 | 6 ng | KKRNRTLTK | 100 μM | 1 μM |

TABLE 4

Figure 2:
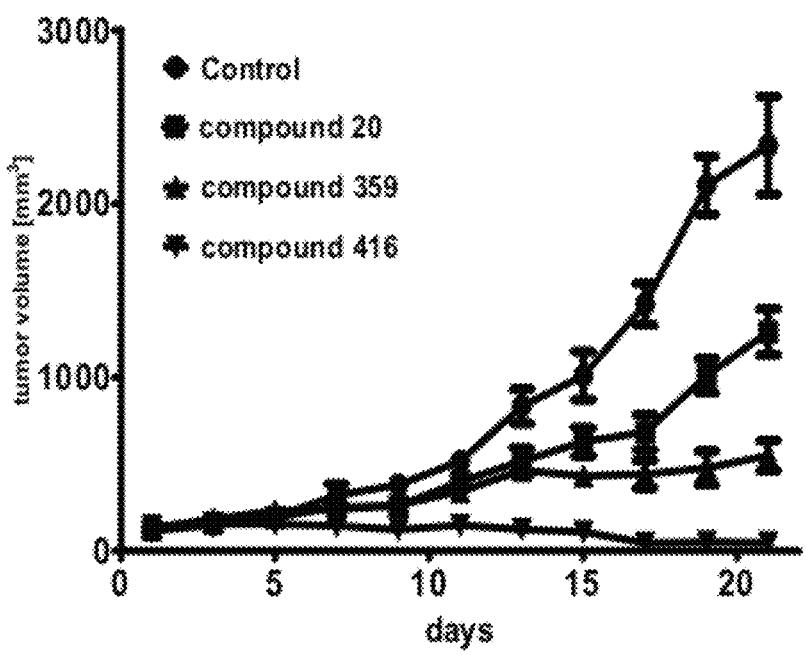
FIG. 2 shows the MV411 tumor growth progression after treatment with compounds 20, 359, and 416. Details of the experiment are described in example 13.

In vitro activity of compounds of Formula A and B.
As reference compounds previously described halogenated derivatives of benzotriazole, benzimidazole and benzopyrazole were used (Pagano et al., Biochem. J. 2008 415, 353-365), Structures of used reference compounds DMAT, TBB, TBI, K66 and K64 are depicted on FIG. 2 of the above publication.

| Compound number | PIM-1 IC50 [nM] | MV-4-11 ED50 [μM] | Jurkat ED50 [μM] | K562 ED50 [μM] | HEL92 ED50 [μM] |
|---|---|---|---|---|---|
| DMAT | 31.02 | 3.15 | 8.18 | >10 | |
| TBB | >1000 | >10 | >10 | >10 | |
| TBI | 101.85 | >10 | >10 | >10 | |
| K66 | >1000 | >10 | >10 | >10 | |
| K64 | >1000 | >10 | >10 | >10 | |
| 18 | 13.32 | 7.68 | | | |
| 19 | 29.4 | 6.83 | 4.63 | | |
| 20 | 16.95 | 0.48 | 2.19 | 6.46 | 6.04 |
| 21 | 41.9 | 3.78 | 2.63 | 7.99 | |
| 75 | 278.8 | 3.33 | 7.79 | | |

TABLE 4-continued

In vitro activity of compounds of Formula A and B.
As reference compounds previously described halogenated derivatives of
benzotriazole, benzimidazole and benzopyrazole were used (Pagano et al.,
Biochem. J. 2008 415, 353-365), Structures of used reference compounds
DMAT, TBB, TBI, K66 and K64 are depicted on FIG. 2 of the above publication.

| | | | | |
|---|---|---|---|---|
| 76 | 117.2 | 5.27 | 3.06 | |
| 256 | | 2.6 | 4.86 | |
| 260 | 29.92 | 1.45 | 5.35 | |
| 262 | 61.36 | | | |
| 266 | 293.9 | 2.55 | | |
| 343 | 36.79 | | | |
| 350 | 32.73 | 5.52 | | |
| 353 | 70.80 | 7.53 | | ~10 |
| 359 | 6.84 | 0.6 | 3.05 | 3.85 |
| 364 | 10.25 | 1.97 | 5.21 | 5.57 |
| 367 | 39.48 | 3.77 | | |
| 374 | 107.03 | 1.3 | 2.94 | 3 |
| 376 | | 5.17 | | 7.93 |
| 377 | | 5.92 | | 9.73 |
| 378 | 39.13 | 6.15 | | 9.04 |
| 383 | 94.40 | 3.43 | | |
| 385 | 45.29 | 4.57 | | 2.21 |
| 386 | 57.96 | 3.31 | 2.86 | 6.12 |
| 387 | | 2.13 | | |
| 392 | 6.72 | 7.55 | | |
| 414 | | 3.03 | | 7.1 |
| 416 | 6.55 | 0.55 | 3.65 | 2.72 |
| 417 | 9.36 | 0.56 | 4.96 | 3.28 |
| 441 | 65 | 0.7 | 1.65 | 0.6 |
| 450 | 125 | 0.6 | 2.9 | 0.8 |

| Compound number | MCF-7 ED50 [μM] | SW480 ED50 [μM] | PC-3 ED50 [μM] | HepG2 ED50 [μM] |
|---|---|---|---|---|
| DMAT | >10 | >10 | >10 | >10 |
| TBB | | >10 | >10 | >10 |
| TBI | | 7.21 | >10 | >10 |
| K66 | | >10 | >10 | >10 |
| K64 | | 9.13 | >10 | >10 |
| 18 | | | | |
| 19 | | | | |
| 20 | 2.47 | 3.45 | 5.14 | 2.86 |
| 21 | | 5.98 | | 6.32 |
| 75 | | | | 5.85 |
| 76 | | | | 4.54 |
| 256 | 5.11 | | 5.18 | 3.39 |
| 260 | 5.65 | | 5.59 | 7.04 |
| 262 | | | | |
| 266 | | | | 2.48 |
| 343 | | | | |
| 350 | 6.55 | | 8.48 | 5.55 |
| 353 | | | | 8.01 |
| 359 | 1.6 | 1.6 | 2.95 | 1.85 |
| 364 | 1.6 | 1.27 | 4.58 | 2.33 |
| 367 | | | | |
| 374 | 1.5 | 1.44 | 2.5 | 1.33 |
| 376 | | | 6.61 | 9.4 |
| 377 | | | 5.99 | 9.72 |
| 378 | 6.19 | 5 | 6.66 | 4.2 |
| 383 | 8.32 | 3.72 | 8.3 | 7.12 |
| 385 | 5.8 | | 6.88 | 3.76 |
| 386 | 2.47 | 1.77 | 2.77 | |
| 387 | 9.25 | 3.27 | 5.49 | |
| 392 | | 1.85 | 4.48 | |
| 414 | 8.23 | 4.32 | 8.94 | |
| 416 | 1.26 | 1.25 | 2.1 | 1.31 |
| 417 | 2.54 | 2.56 | 2.57 | 1.85 |
| 441 | 1.3 | 0.7 | 1.6 | 0.7 |
| 450 | 2 | 1 | 3.6 | 1.5 |

| Compound number | PIM-1 IC50 [nM] | MV-4-11 ED50 [μM] | Jurkat ED50 [μM] | K562 ED50 [μM] | HEL92 ED50 [μM] |
|---|---|---|---|---|---|
| DMAT | 31.02 | 3.15 | 8.18 | >10 | |
| TBB | >1000 | >10 | >10 | >10 | |
| TBI | 101.85 | >10 | >10 | >10 | |
| K66 | >1000 | >10 | >10 | >10 | |
| K64 | >1000 | >10 | >10 | >10 | |
| 11 | 5.89 | 1.03 | 3.46 | 7.47 | 5.7 |

TABLE 4-continued

In vitro activity of compounds of Formula A and B.
As reference compounds previously described halogenated derivatives of
benzotriazole, benzimidazole and benzopyrazole were used (Pagano et al.,
Biochem. J. 2008 415, 353-365), Structures of used reference compounds
DMAT, TBB, TBI, K66 and K64 are depicted on FIG. 2 of the above publication.

| | | | | | |
|---|---|---|---|---|---|
| 13 | 319.25 | 3.16 | 1.34 | 3.72 | |
| 14 | 57.76 | 1.29 | 2.65 | 3.59 | |
| 16 | 106.8 | 2.17 | 2.46 | | |
| 28 | 36.95 | | | | |
| 58 | 25.67 | 1.54 | 3.37 | | |
| 59 | 50.79 | 2.81 | 4.41 | | |
| 61 | 8.85 | 4.43 | 7.92 | | |
| 65 | 22.70 | 3.46 | | | 8.37 |
| 67 | 65.24 | | | | |
| 79 | 68.17 | 4.4 | 9.06 | | |
| 82 | 200.1 | | | | |
| 85 | 65.32 | 2.66 | | | |
| 86 | 66.05 | 5.81 | 8.27 | | |
| 87 | 15.07 | 4.2 | 5.81 | 5.59 | 9.07 |
| 90 | 13.05 | 2.12 | 5.78 | | |
| 95 | 75.66 | 7.61 | | | |
| 117 | 85.6 | 9.4 | | | |
| 128 | 71.3 | 3.83 | | | |
| 158 | 62.74 | 4.86 | 8.42 | | |
| 166 | 51.01 | 1.19 | 4.92 | | |
| 192 | 45.35 | 5.13 | 7.67 | | |
| 236 | | 1.6 | 4.4 | | |
| 243 | | 6.84 | 6.12 | | |
| 247 | 109.0 | 5.96 | 7.84 | | |
| 248 | 48.89 | | | | |
| 259 | | 6.44 | 7.11 | | |
| 261 | 137.9 | 3.41 | 4.52 | | |
| 263 | 47.5 | 2.39 | 2.56 | | |
| 265a | 67.42 | 2.22 | 3.62 | | |
| 272 | 43.34 | 2.42 | 2.76 | | |
| 296 | 170 | 4.15 | 8.12 | | |
| 303 | 127.6 | | | | |
| 304cis | 6.9 | 0.33 | | | 1.82 |
| 304RR | 5.26 | 0.25 | 3.15 | | |
| 304SS | 11.58 | 0.98 | 5.07 | | |
| 307 | 287 | 6.03 | 8.97 | | |
| 309 | 15.91 | 5.54 | 8.18 | | |
| 317 | 598 | 3.95 | 7.05 | | |
| 329 | 46.98 | | 4.45 | | |
| 331 | 14.75 | 1.36 | | | |
| 332 | 16.24 | 3.27 | | | 3.15 |
| 333 | 48.53 | 3.86 | | | 3.25 |
| 334 | 14.12 | 5.34 | | | |
| 336 | 18.84 | 2.6 | | 6.88 | |
| 337 | 25.56 | 2.45 | | 3.02 | 4.5 |
| 338 | 21.71 | 3.3 | | 5.03 | 5.68 |
| 342 | 28.57 | | | | |
| 349 | 69.76 | 1.58 | | 6.51 | 6 |
| 354 | 107.9 | 4.47 | | | 6.93 |
| 358 | 5.82 | 1 | | 6.64 | 7.65 |
| 366 | 3.5 | 0.6 | | 5.04 | 5.1 |
| 369 | 41.07 | 1.3 | | 3.53 | 6.2 |
| 372 | 45.22 | 1.65 | | | 3.98 |
| 413 | 118.6 | 1.55 | | 2.73 | 3.29 |
| 435 | 6.68 | 0.68 | | 5.64 | 5.71 |

| Compound number | MCF-7 ED50 [µM] | SW480 ED50 [µM] | PC-3 ED50 [µM] | HepG2 ED50 [µM] |
|---|---|---|---|---|
| DMAT | >10 | >10 | >10 | >10 |
| TBB | | >10 | >10 | >10 |
| TBI | | 7.21 | >10 | >10 |
| K66 | | >10 | >10 | >10 |
| K64 | | 9.13 | >10 | >10 |
| 11 | 4.7 | 2.47 | 4.9 | 2.84 |
| 13 | 3.65 | 1.08 | 3.86 | 2.54 |
| 14 | 7.76 | 1.53 | 3.96 | 2.12 |
| 16 | | 9.68 | | 8.78 |
| 28 | | | | |
| 58 | | | | 2.93 |
| 59 | | | | 3.6 |
| 61 | | | 8.33 | 7.35 |
| 65 | 8.22 | 6.92 | 7.45 | |
| 67 | | | | |

TABLE 4-continued

In vitro activity of compounds of Formula A and B.
As reference compounds previously described halogenated derivatives of benzotriazole, benzimidazole and benzopyrazole were used (Pagano et al., Biochem. J. 2008 415, 353-365), Structures of used reference compounds DMAT, TBB, TBI, K66 and K64 are depicted on FIG. 2 of the above publication.

| | | | | |
|---|---|---|---|---|
| 79 | | | | 6.52 |
| 82 | | | | |
| 85 | 4.12 | | 5.84 | 2.84 |
| 86 | | | | |
| 87 | 5.62 | 2.03 | 5.65 | 3.8 |
| 90 | | | 6.52 | 3.98 |
| 95 | | | | |
| 117 | | | | |
| 128 | | | | |
| 158 | 8.31 | | 8.83 | 3.58 |
| 166 | 4.93 | | 3.15 | 2.62 |
| 192 | | | | 6.23 |
| 236 | 4.2 | | 2.5 | 2.2 |
| 243 | | | | 9 |
| 247 | 7.15 | | | 9.01 |
| 248 | | | | |
| 259 | 5.9 | | 3.51 | 5.49 |
| 261 | 4.94 | | 3.2 | 4.29 |
| 263 | 2.76 | | 2.64 | 2.66 |
| 265a | 3.09 | | 4.57 | 1.8 |
| 272 | 4.51 | | 4.87 | 2.26 |
| 296 | | | 4.21 | 5.91 |
| 303 | | | | |
| 304cis | 0.7 | | 1.47 | 1.34 |
| 304RR | 2.36 | | 3.16 | 2.64 |
| 304SS | 5.03 | | 5.17 | 3.21 |
| 307 | 9.43 | | 8.31 | 1.23 |
| 309 | | | | 4.87 |
| 317 | 6.63 | | | 4.33 |
| 329 | | | 4.69 | |
| 331 | | | | |
| 332 | | | 7.51 | 6.59 |
| 333 | 4.76 | | 2.49 | 4.52 |
| 334 | | | | |
| 336 | 6.2 | 4.15 | 8.4 | 4.87 |
| 337 | 1.78 | 1.61 | 3.83 | 2.4 |
| 338 | 2.5 | 1.95 | 4.76 | 2.76 |
| 342 | | | | |
| 349 | 2.75 | 1.61 | 4.7 | 2.51 |
| 354 | 3.09 | | 8.59 | 2.61 |
| 358 | 3.03 | 2.42 | 6.2 | 2.65 |
| 366 | 2.15 | 2.84 | 5.6 | 1.7 |
| 369 | 1.6 | 0.55 | 2.45 | 1.4 |
| 372 | 2.54 | | 2.4 | 1.32 |
| 413 | 1.3 | 0.58 | 1.45 | 1.36 |
| 435 | 3.49 | 1.27 | 5.79 | |

DMAT: 2-dimethylamino-4,5,6,7-tetrabromo-1H-benzimidazole
TBB: 4,5,6,7-tetrabromo-1Hbenzotriazole
TBI- or TBBz: 4,5,6,7-tetrabromo-1H-benzimidazole
K66: 1-carboxymethyl-2-dimethylamino-4,5,6,7-tetrabromo-benzimidazole
K64: 3,4,5,6,7-pentabromo-1H-indazole

Example 11

Kinase Panel Results

Kinase panel profiling was performed at Millipore using the Millipore's KinaseProfiler™ service, a high-throughput method for screening small molecule compounds against large numbers of different wild type and mutant kinases. This kinase panel is based on radiometric assay that quantitatively measures the ability of a compound to prevent phosphorylation of a peptide substrate. The radiometric based filtration binding assay is considered to be the "gold standard" to which other non-radiometric methods are compared. In this assay type, the kinase reaction is performed in the presence of radioactive ATP isotope followed by binding of the final radioisotope labeled products to filters. After the reaction was performed, unreacted phosphate is washed away and the levels of phosphorylated radioactive substrate are measured. Selectivity of kinase inhibition is one of the key parameters in therapeutic use of this class of compounds. Off-target inhibition could be one of the major safety and toxicity issues in drug development and use of the compounds for treatment of various disease conditions, but also can be one of the reasons of potency and anticancer effect displayed by the compound. Several examples of kinase inhibitors are described in the literature for which after a more detailed and broad analysis is was shown, that the activity is not related to primary target. Therefore representative compounds disclosed in the application were tested on a panel kinases to determine specificity in PIM kinase inhibition. Table 5 provides selectivity data for representative compound 4,5,6,7-tetrabromo-1-ethyl-2-(piperazin-1-yl)-1H-benzo[d]imidazole (compound 416). As indicated in the Table 5 when tested at 1 μM concentration 4,5,6,7-tetrabromo-1-ethyl-2-(piperazin-1-yl)-1H-benzo[d]

imidazole was revealed to be not only a potent inhibitor of PIM kinases, but also exerts activity on a set of other kinases.

TABLE 5

KinomeScan Max kinase binding inhibition panel results for 4,5,6,7-tetrabromo-1-ethyl-2-(piperazin-1-yl)-1H-benzo[d]imidazole tested at 1 μM in duplicate. Values represent % of remaining kinase activity

| Kinase | % remaining activity |
|---|---|
| HIPK3(h) | −1 |
| Flt3(h) | 0 |
| CDK5/p25(h) | 1 |
| Flt3(D835Y)(h) | 1 |
| HIPK2(h) | 1 |
| PIM-1(h) | 1 |
| CDK5/p35(h) | 2 |
| CLK2(h) | 2 |
| Haspin(h) | 2 |
| PKG1β(h) | 5 |
| CDK2/cyclinE(h) | 6 |
| CK1(y) | 6 |
| cKit(D816H)(h) | 6 |
| TAO1(h) | 6 |
| CDK1/cyclinB(h) | 7 |
| CDK2/cyclinA(h) | 7 |
| PKG1α(h) | 7 |
| HIPK1(h) | 8 |
| PIM-2(h) | 10 |
| EGFR(T790M, L858R)(h) | 11 |
| Mer(h) | 14 |
| TAO3(h) | 14 |
| CDK3/cyclinE(h) | 16 |
| MSK2(h) | 16 |
| Flt4(h) | 17 |
| Mnk2(h) | 17 |
| PDGFRα(D842V)(h) | 17 |
| Ret(V804M)(h) | 20 |
| EGFR(L858R)(h) | 22 |
| CDK7/cyclinH/MAT1(h) | 25 |
| PKCθ(h) | 26 |
| Ret (V804L)(h) | 26 |
| CDK9/cyclin T1(h) | 27 |
| EGFR(L861Q)(h) | 27 |
| Ret(h) | 27 |
| CaMKIIδ(h) | 28 |
| EGFR(T790M)(h) | 28 |
| KDR(h) | 28 |
| PASK(h) | 28 |
| PKCµ(h) | 30 |
| IRAK1(h) | 33 |
| PIM-3(h) | 34 |
| cKit(V560G)(h) | 35 |
| TRKA(h) | 35 |
| Axl(h) | 36 |
| cKit(V654A)(h) | 36 |
| TRKB(h) | 37 |
| PKBγ(h) | 39 |
| Flt1(h) | 40 |
| Src(T341M)(h) | 40 |
| CaMKIIγ(h) | 41 |
| Lck(h) | 43 |
| MKK6(h) | 43 |
| DYRK2(h) | 45 |
| Yes(h) | 48 |
| LOK(h) | 50 |
| SAPK4(h) | 51 |
| Fes(h) | 52 |
| IRAK4(h) | 52 |
| TAK1(h) | 52 |
| MSK1(h) | 54 |
| IKKα(h) | 56 |
| p70S6K(h) | 56 |
| PRK2(h) | 56 |
| Rsk1(h) | 56 |
| PKD2(h) | 58 |
| CK2(h) | 59 |
| PKBα(h) | 59 |

TABLE 5-continued

KinomeScan Max kinase binding inhibition panel results for 4,5,6,7-tetrabromo-1-ethyl-2-(piperazin-1-yl)-1H-benzo[d]imidazole tested at 1 μM in duplicate. Values represent % of remaining kinase activity

| Kinase | % remaining activity |
|---|---|
| GSK3α(h) | 60 |
| cKit(D816V)(h) | 61 |
| CK1δ(h) | 62 |
| Hck(h) activated | 63 |
| Lyn(h) | 65 |
| Src(1-530)(h) | 65 |
| GSK3β(h) | 66 |
| STK33(h) | 66 |
| AMPKα2(h) | 67 |
| CaMKIIβ(h) | 67 |
| Fgr(h) | 67 |
| PDGFRα(V561D)(h) | 68 |
| SAPK3(h) | 68 |
| FGFR1(V561M)(h) | 69 |
| Lck(h) activated | 69 |
| Met(M1268T)(h) | 70 |
| Met(Y1248H)(h) | 70 |
| PKA(h) | 70 |
| MST1(h) | 71 |
| ROCK-II(r) | 71 |
| Rsk3(h) | 71 |
| Fms(h) | 72 |
| Met(D1246H)(h) | 72 |
| CK2α2(h) | 73 |
| Fyn(h) | 73 |
| Lyn(m) | 73 |
| MEK1(h) | 73 |
| Met(Y1248C)(h) | 73 |
| NEK11(h) | 73 |
| JAK3(h) | 74 |
| Met(D1246N)(h) | 74 |
| PrKX(h) | 74 |
| EphA1(h) | 75 |
| GCK(h) | 75 |
| IGF-1R(h) | 75 |
| BRK(h) | 76 |
| CHK2(h) | 76 |
| CHK2(R145W)(h) | 76 |
| IKKβ(h) | 78 |
| cSRC(h) | 79 |
| Hck(h) | 79 |
| PAK4(h) | 79 |
| RIPK2(h) | 79 |
| Rsk1(r) | 79 |
| SGK2(h) | 79 |
| Aurora-B(h) | 80 |
| CHK2(I157T)(h) | 80 |
| MAPK2(h) | 81 |
| Met(h) | 81 |
| Met(Y1248D)(h) | 81 |
| ROCK-II(h) | 81 |
| Rsk2(h) | 81 |
| AMPKα1(h) | 82 |
| CLK3(h) | 82 |
| DRAK1(h) | 82 |
| MAPK2(m) | 82 |
| TAO2(h) | 82 |
| CK1γ1(h) | 83 |
| SIK(h) | 84 |
| ULK3(h) | 84 |
| CaMKIV(h) | 85 |
| CK1γ2(h) | 85 |
| c-RAF(h) | 85 |
| NEK3(h) | 85 |
| NLK(h) | 85 |
| PAK6(h) | 85 |
| PAR-1Bα(h) | 85 |
| LKB1(h) | 86 |
| MELK(h) | 86 |
| SAPK2a(T106M)(h) | 86 |
| EphB1(h) | 87 |
| IGF-1R(h), activated | 87 |

TABLE 5-continued

KinomeScan Max kinase binding inhibition panel results for 4,5,6,7-tetrabromo-1-ethyl-2-(piperazin-1-yl)-1H-benzo[d]imidazole tested at 1 μM in duplicate. Values represent % of remaining kinase activity

| Kinase | % remaining activity |
|---|---|
| JNK3(h) | 87 |
| MINK(h) | 87 |
| MLK1(h) | 87 |
| MSSK1(h) | 87 |
| TGFBR1(h) | 87 |
| MLCK(h) | 88 |
| PhKγ2(h) | 88 |
| ULK2(h) | 88 |
| CaMKI(h) | 89 |
| CK1γ3(h) | 89 |
| EGFR(h) | 89 |
| ErbB4(h) | 89 |
| PKCδ(h) | 89 |
| Rsk4(h) | 89 |
| Abl(m) | 90 |
| PKBβ(h) | 90 |
| ROCK-I(h) | 90 |
| SGK(h) | 90 |
| Snk(h) | 90 |
| BrSK2(h) | 91 |
| CDK6/cyclinD3(h) | 91 |
| CSK(h) | 91 |
| EphA7(h) | 91 |
| FGFR2(h) | 91 |
| GRK6(h) | 91 |
| IRR(h) | 91 |
| MARK1(h) | 91 |
| NEK2(h) | 91 |
| PRAK(h) | 91 |
| SAPK2b(h) | 91 |
| Tie2(Y897S)(h) | 91 |
| Abl(T315I)(h) | 92 |
| Abl(Y253F)(h) | 92 |
| DAPK2(h) | 92 |
| Fms(Y969C)(h) | 92 |
| PKCη(h) | 92 |
| SGK3(h) | 92 |
| Tie2 (h) | 92 |
| ARK5(h) | 93 |
| GRK7(h) | 93 |
| IR(h), activated | 93 |
| MST2(h) | 93 |
| MST3(h) | 93 |
| PAK5(h) | 93 |
| PKCγ(h) | 93 |
| Bmx(h) | 94 |
| CaMKIδ(h) | 94 |
| EphA3(h) | 94 |
| FAK(h) | 94 |
| FGFR4(h) | 94 |
| MAPK1(h) | 94 |
| WNK3(h) | 94 |
| Abl (M351T)(h) | 95 |
| MKK7β(h) | 95 |
| mTOR(h) | 95 |
| PAK2(h) | 95 |
| PKCα(h) | 95 |
| Syk(h) | 95 |
| TSSK2(h) | 95 |
| ZIPK(h) | 95 |
| Arg(m) | 96 |
| GRK5(h) | 96 |
| MRCKα(h) | 96 |
| TSSK1(h) | 96 |
| ACK1(h) | 97 |
| Blk(m) | 97 |
| DMPK(h) | 97 |
| JNK1α1(h) | 97 |
| NEK6(h) | 97 |
| Pyk2(h) | 97 |
| Abl (Q252H) (h) | 98 |
| LIMK1(h) | 98 |
| PDGFRα(h) | 98 |
| PKCβII(h) | 98 |
| EphA4(h) | 99 |
| EphA5(h) | 99 |
| FGFR1(h) | 99 |
| PTK5(h) | 99 |
| SAPK2a(h) | 99 |
| Txk(h) | 99 |
| ASK1(h) | 100 |
| DAPK1(h) | 100 |
| EphB4(h) | 100 |
| Fer(h) | 100 |
| JNK2α2(h) | 100 |
| MKK4(m) | 100 |
| PAK3(h) | 100 |
| DCAMKL2(h) | 101 |
| FGFR2(N549H)(h) | 101 |
| MAPKAP-K2(h) | 101 |
| Plk3(h) | 101 |
| Tie2(R849W)(h) | 101 |
| BTK(R28H)(h) | 102 |
| EphA8(h) | 102 |
| PDGFRβ(h) | 102 |
| PKCβI(h) | 102 |
| SRPK2(h) | 102 |
| WNK2(h) | 102 |
| BrSK1(h) | 103 |
| mTOR/FKBP12(h) | 103 |
| MuSK(h) | 103 |
| VRK2(h) | 103 |
| IR(h) | 104 |
| PKCε(h) | 104 |
| PKCι(h) | 104 |
| Ros(h) | 104 |
| TBK1(h) | 104 |
| TLK2(h) | 104 |
| DDR2(h) | 105 |
| FGFR3(h) | 105 |
| Itk(h) | 105 |
| Rse(h) | 105 |
| ALK(h) | 106 |
| EphA2(h) | 106 |
| EphB2(h) | 106 |
| MAPKAP-K3(h) | 106 |
| SRPK1(h) | 106 |
| Abl(h) | 107 |
| Abl (H396P) (h) | 107 |
| BTK(h) | 107 |
| eEF-2K(h) | 107 |
| PKCζ(h) | 107 |
| Tec(h) activated | 107 |
| Ron(h) | 108 |
| ZAP-70(h) | 108 |
| PDK1(h) | 109 |
| ALK4(h) | 112 |
| CHK1(h) | 113 |
| MRCKβ(h) | 113 |
| NEK7(h) | 115 |
| Plk1(h) | 117 |
| Arg(h) | 119 |
| cKit(h) | 121 |
| EphB3(h) | 121 |
| JAK2(h) | 121 |
| Aurora-A(h) | 125 |

Example 12

In Vitro Inhibition of Protein Phosphorylation

The inventors have investigated the efficacy of PIM-1 kinase inhibition by compound 20 on MV4-11 cells 4 h and 24 h after the treatment. The efficacy of PIM-1 inhibition was evaluated basing on the changes in the expression and phosphorylation levels of its downstream target proteins, using Western blot (FIG. 1). Sunitinib was used as a positive control. After densitometric quantification of the obtained results, cellular $IC_{50}$ was assessed (Table 6). The analysis revealed dose dependent inhibition of c-MYC after 4 h and 24 h being most efficient after 4 h. Similarly, another biomarker, p-4EBP1(Ser65), showed dose- and time-dependent inhibition. PIM-1 and tubulin protein levels were assessed as controls.

TABLE 6

Comparison of calculated cellular IC50 for biomarker inhibition in MV411 cells after 4 and 24 h treatment with compound 20. Values are given in μM concentration.

| | Compound 20 | |
|---|---|---|
| | 4 h | 24 h |
| c-MYC | 0.89 | 2.03 |
| p-4EBP1 (Ser65) | 3.13 | 1.12 |

Example 13

In Vivo Anticancer Activity

The anticancer activity of compounds 20, 359 and 416 was assessed on tumors derived from MV4-11 cells xenografted in nude mice. Mice were inoculated with $5*10^6$ cells and the tumor volume was measured until it reached 100 mm³. Then, compounds were administered per os (PO), every day (QD) for 21 days, at the doses as indicated in the Table 7. Throughout the whole study tumor volume has been measured (FIG. 2) and tumor growth inhibition (TGI) was calculated. After 21 days of treatment, compounds 20 (dose 150 mg/kg, administration QD), 359 and 416 showed the most pronounced tumor growth inhibition (Table 7).

TABLE 7

Comparison of xenograft results after treatment with compound 20, -359, and -416 compounds.

| Compound | Dose | TGI (%) |
|---|---|---|
| Control | — | 0 |
| Compound 20 | 150 mg/kg, QD | −57.8 |
| Compound 359 | 150 mg/kg, QD | −84.7 |
| Compound 416 | 150 mg/kg, QD | −102.8 |

TGI—tumor growth inhibition, QD—once a day.

Example 14

Solubility Comparison of the Compounds in pH 7.4—Results Summarized in Table 8

Compound stock solutions were prepared in DMSO to final concentrations of 1000 mM. For each compound studied, 12 solutions were prepared to cover concentrations from 0.001 to 1 mM. As a solvent 0.2 mM phosphate buffer (pH 7.4) was used. The final concentration of DMSO in the solutions was 1% (v/v). The solutions were left mixing for 24 hours at 37° C., 350 rpm and following incubation centrifuged for 5 minutes at 14500 rpm. The samples were then analyzed by RP HPLC using a C18 column and 0.2% solution of formic acid in water/acetonitrile mobile phase. For low concentration solutions the HPLC signal dependence on compound concentration is linear and reaches plateau for higher concentrations. The solubility was determined as the point as the point at which the concentration curve reaches plateau. Examples of the results for chosen compounds are shown in Table 8. In general, tetrahalogenated benzimidazoles are poorly soluble compounds, what renders their chances for successful therapeutic administration in commonly used routes of administration and standard conditions. In contrast to previously published tetrabromobenzimidazoles exemplified by DMAT, certain compounds provided in the application show a markedly increase in water solubility. As solubility is one of the key parameters that influences compound pharmacokinetics, permeability and therefore also activity in vitro and in vivo, improved solubility of the selected compounds is a surprising feature that can lead to improved efficacy in treating PIM kinase associated disease conditions.

TABLE 8

Solubility of the compounds in pH 7.4.

| Compound No. | Solubility [mM] in phosphate buffer pH 7.4 |
|---|---|
| DMAT | <0.01 |
| Compound 20 | 0.081 |

The invention claimed is:
1. A compound of formula (A):

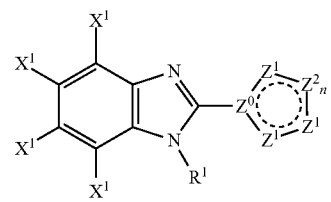

wherein:
$X^1$ is independently selected at each occurrence from F, Cl, or Br;
$Z^0$ is selected from C, CH, and N;
$Z^1$ is independently selected at each occurrence from $CR^2$, $CHR^3$, N, $NR^4$, and O;
$Z^2$ is independently selected at each occurrence from $CR^2$, $CHR^3$, N, $NR^4$, O, and S;
n is 1, 2, 3, or 4 to form a 5-, 6-, 7-, or 8-membered carbocycle or heterocycle, either of which is saturated or unsaturated, nonaromatic;
or $Z^1$ and $Z^2$ are optionally taken together independently to form a second and optionally a third fused ring to form at least one 4-, 5-, 6-, or 7-membered carbocycle or heterocycle, which is saturated or unsaturated or aromatic and which is optionally substituted with one or more substituents selected from H, halogen, amino, hydroxyl, aminoalkyl, alkoxy, carboxylic acid, carboxyester, carboxamide, carbamate, sulfonic acid, sulfonamide and trifluoromethyl, wherein said 4- to 7-membered heterocyclic groups contain one or more heteroatoms selected from N, O, and S;

$R^1$ is selected from the group consisting of H, methyl, carboxyester, carboxamide, sulfonamide, $-(C_{2-6}alkyl)R_A$, and 5- to 8-membered carbocyclic and heterocyclic groups, which are saturated, unsaturated, or aromatic, which are optionally substituted with one or more substitutents selected from H, halogen, amino, hydroxyl, aminoalkyl, alkoxy, carboxylic acid, carboxyester, carboxamide, carbamate, sulfonic acid, sulfonamide and trifluoromethyl, wherein said 5- to 8-membered heterocyclic groups contain one or more heteroatoms selected from N, O, and S, with point of attachment being carbon, wherein said $-(C_{2-6}alkyl)R_A$ is optionally branched and further substituted with one or more substituents selected from oxo, hydroxyl, and amino;

$R^2$ is independently selected at each occurrence from the group consisting of H, halogen, amino, hydroxyl, oxo, aminoalkyl, alkoxy, carboxylic acid, carboxyester, carboxamide, carbamate, sulfonic acid, sulfonamide, $-Y^1(C_{1-6}alkyl)R_A$, and $Y^1R_B$, wherein said $-Y^1(C_{1-6}alkyl)R_A$ is optionally branched and further substituted with one or more substituents selected from oxo, hydroxyl, and amino;

$R^3$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, $-Y^1(C_{1-6}alkyl)R_A$, and $Y^1R_B$, wherein said $-Y^1(C_{1-6}alkyl)R_A$ is optionally branched and further substituted with one or more substituents selected from oxo, hydroxyl, and amino;

$R^4$ is independently selected at each occurrence from the group consisting of H, carboxyester, carboxamide, carbamate, sulfonamide, amidine, $-Y^1(C_{1-6}alkyl)R_A$, and $R_B$ with the proviso that the point of attachment on $R_B$ is carbon, wherein said $-Y^1(C_{1-6}alkyl)R_A$ is optionally branched and further substituted with one or more substituent(s) substituents selected from oxo, hydroxyl, nitrile and amino;

$R_A$ is independently selected at each occurrence from the group consisting of H, amino, hydroxyl, aminoalkyl, alkoxy, carboxylic acid, carboxyester, carboxamide, carbamate, sulfonic acid, sulfonamide, trifluoromethyl, 5- to 9-membered mono- or bicyclic carbocyclic and heterocyclic groups, which are saturated, unsaturated, or aromatic, which are optionally substituted with one or more substituents selected from H, halogen, amino, hydroxyl, alkyl, aminoalkyl, alkoxy, carboxylic acid, carboxyester, carboxamide, carbamate, sulfonic acid, sulfonamide, trifluoromethyl, substituted or unsubstituted aryl and heteroaryl, wherein said 5- to 9-membered heterocyclic groups contain one or more heteroatoms selected from N, O, and S, with point of attachment being carbon or nitrogen;

$R_B$ is independently selected at each occurrence from the group consisting of 5- to 8-membered carbocyclic and heterocyclic groups, which are saturated, unsaturated, or aromatic, which are optionally substituted with one or more substitutents selected from H, halogen, amino, hydroxyl, alkyl, aminoalkyl, alkoxy, carboxylic acid, carboxyester, carboxamide, carbamate, sulfonic acid, sulfone, sulfonamide, trifluoromethyl, aryl and heteroaryl, wherein said 5- to 8-membered heterocyclic groups contain one or more heteroatoms selected from N, O, and S, with point of attachment being carbon or nitrogen;

$Y^1$ is absent, or independently selected at each occurrence from the group consisting of $-C(O)-$, $-C(O)NH-$, $-S(O)_2-$, $-S(O)_2NH-$, $-C(O)O-$, and $-C(NH)NH-$;

or an enantiomer thereof or a mixture of its enantiomers or its pharmaceutically acceptable salt.

2. The compound according to claim 1 of formula (A), wherein n is 2 and $Z^0$, $Z^1$ and $Z^2$ are selected such that a 6-membered heterocycle is formed.

3. The compound according to claim 1, wherein the pharmaceutically acceptable salt is selected from the group consisting of the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate.

4. A pharmaceutical composition comprising a therapeutically effective amount of at least one compound according to claim 1.

5. The pharmaceutical composition according to claim 4, wherein said therapeutically effective amount is about 0.01 to about 1000 mg/kg per day.

6. The pharmaceutical composition according to claim 4, wherein said composition additionally comprises at least one therapeutic agent selected from the group comprising a chemotherapeutic or anti-proliferative agent, an immunomodulatory or immunosuppressive agent, or an anti-inflammatory agent.

7. The pharmaceutical composition according to claim 4, wherein said composition comprises the at least one compound as the only pharmaceutically active agent.

8. The pharmaceutical composition according to claim 4, wherein said composition is administered parenterally, vaginally, rectally, transdermally, orally or through the otolaryngologal sphere.

9. The pharmaceutical composition according to claim 4, wherein said composition additionally comprises at least one pharmaceutically acceptable excipient selected from the group consisting of flavoring agents, sweetener, lubricants, solubilizers, suspending agents, fillers, glidants, compression aides, binders, tablet-disintegrating agents, effervescing agent, wetting agent encapsulating materials, dyestuff, and mixtures thereof.

10. The pharmaceutical composition according to claim 4, wherein said composition is a sterile solution or suspension suitable for parenteral administration by intramuscular, intraperitoneal, intravenous, intrathecal, or subcutaneous injection or perfusion.

11. The pharmaceutical composition according to claim 4, wherein said composition is an oral dosage form.

12. The pharmaceutical composition according to claim 4, wherein said composition is a transdermal, rectal or vaginal dosage form selected from the group consisting of ointments, creams, lotions, liniments, gels, paste, films, suppositories, enemas and pessaries.

13. The pharmaceutical composition according to claim 4, wherein said composition is a dosage form for administration through the eyes, ears and nose.

14. The pharmaceutical composition according to claim 4, wherein said composition is an immediate, extended or slow-release formulation.

15. A process for the preparation of a compound according to claim 1, wherein said process comprises: reacting of an unsubstituted or substituted 2,4,5,6,7-pentahalogenobenzimidazole with a suitable amine at elevated temperature, wherein the reactive substituents are optionally protected with suitable protecting groups and wherein the resulting product is preferably subjected to purification by crystallization or chromatography according to the reaction.

16. The compound according to claim 2, wherein the combination of $Z^0$, $Z^1$ and $Z^2_n$ forms a 6-membered heterocycle that is saturated.

17. The compound according to claim 16, wherein the 6-membered heterocycle comprises two N-heteroatoms.

18. The compound according to claim 17, wherein the 6-membered heterocycle is a substituted or unsubstituted piperazine.

19. The compound according to claim 18, wherein $Z^0$ is N, $Z^1$ is $CHR^3$, $Z^2(1)$ is $CHR^3$, and $Z^2(2)$ is $NR^4$.

20. The compound according to claim 19, wherein the compound is 4,5,6,7-tetrabromo-1-ethyl-2-(piperazin-1-yl)-1H-benzo[d]imidazole.

21. The pharmaceutical composition according to claim 11, wherein the oral dosage form is a liquid or solid dosage form selected from the group consisting of pills, tablets, capsules, sachets, dragees, powders, granules, lozenges, powders for reconstitution, orally disintegrating tablet, films, osmotic controlled release capsule, elixir, emulsion, syrup, suspension, tincture and solutions or powder for inhalation and nebulization, or sublingual administration.

22. A method of treating leukemia, adenocarcinoma, lymphoma, multiple myeloma and malignant melanoma, comprising administering to a patient in need of said treating a pharmaceutical composition comprising a compound according to claim 1.

23. The method according to claim 22, wherein said administering is to a patient having acute myeloid leukemia, chronic myeloid leukemia, multiple myeloma, or non-Hodgkin's lymphoma.

* * * * *